US010696737B2

(12) United States Patent
Sączyńska et al.

(10) Patent No.: US 10,696,737 B2
(45) Date of Patent: Jun. 30, 2020

(54) MONOCLONAL ANTIBODIES AGAINST HEMAGGLUTININ OF H5-SEROTYPE INFLUENZA VIRUSES AND THEIR USES, HYBRIDOMAS PRODUCING SAID ANTIBODIES, COMPOSITIONS AND DIAGNOSTIC KITS

(71) Applicants: SIEC BADAWCZA LUKASIEWICZ—INSTYTUT BIOTECHNOLOGII I ANTYBIOTYKOW, Warsaw (PL); UNIWERSYTET GDAŃSKI, Gdańsk (PL)

(72) Inventors: Violetta Sączyńska, Warsaw (PL); Violetta Cecuda-Adamczewska, Warsaw (PL); Anna Porębska, Warsaw (PL); Katarzyna Florys, Warsaw (PL); Anna Bierczyńska-Krzysik, Warsaw (PL); Piotr Baran, Warsaw (PL); Agnieszka Romanik-Chruścielewska, Jozefow (PL); Grażyna Płucienniczak, Warsaw (PL); Andrzej Płucienniczak, Warsaw (PL); Piotr Borowicz, Warsaw (PL); Krzysztof Kucharczyk, Warsaw (PL); Boguslaw Szewczyk, Gdansk (PL)

(73) Assignees: SIEC BADAWCZA LUKASIEWICZ—INSTYTUT BIOTECHNOLOGII I ANTYBIOTYKOW, Warsaw (PL); UNIWERSYTET GDANSKI, Gdansk (PL)

( * ) Notice: Subject to any disclaimer, the term of this patent is extended or adjusted under 35 U.S.C. 154(b) by 0 days.

(21) Appl. No.: 16/332,782

(22) PCT Filed: Sep. 11, 2017

(86) PCT No.: PCT/PL2017/000084
§ 371 (c)(1),
(2) Date: Mar. 12, 2019

(87) PCT Pub. No.: WO2018/048317
PCT Pub. Date: Mar. 15, 2018

(65) Prior Publication Data

US 2019/0352375 A1 Nov. 21, 2019

(30) Foreign Application Priority Data

Sep. 12, 2016 (PL) ........................................ 418 671

(51) Int. Cl.
*C07K 14/005* (2006.01)
*C07K 16/10* (2006.01)
*G01N 33/569* (2006.01)

(52) U.S. Cl.
CPC ........ *C07K 16/1018* (2013.01); *C07K 14/005* (2013.01); *G01N 33/56983* (2013.01); *C07K 2317/33* (2013.01); *C07K 2317/52* (2013.01); *C07K 2317/55* (2013.01); *C07K 2317/76* (2013.01); *C12N 2760/16122* (2013.01); *C12N 2760/16134* (2013.01); *G01N 2333/11* (2013.01)

(58) Field of Classification Search
None
See application file for complete search history.

(56) References Cited

U.S. PATENT DOCUMENTS

2015/0030607 A1 1/2015 Shibo et al.

FOREIGN PATENT DOCUMENTS

| | | | |
|---|---|---|---|
| WO | 2008110937 | A2 | 9/2008 |
| WO | 2009035420 | A1 | 3/2009 |
| WO | 2013105896 | A1 | 7/2013 |

OTHER PUBLICATIONS

Ren et al., Cross-protection of newly emerging HPAI H5 viruses by neutralizing human monoclonal antibodies: A viable alternative to oseltamivir, 2016, MABS, vol. 8, No. 6, pp. 1156-1166.*
Chen et al., "Broad Cross-Protection against H5N1 Avian Influenza Virus Infection by Means of Monoclonal Antibodies that Map to Conserved Viral Epitopes," The Journal of Infectious Diseases, 199(1):49-58 (2009).
Sun et al., "Generation, Characterizaton and Epitope Mapping of Two Neutralizing and Protective Human Recombinant Antibodies against Influenza A H5N1 Viruses," PLoS One, 4(5):e5476 (2009).
Oh et al., "Neutralizing monoclonal antibodies to different Glades of Influenza A H5N1 viruses," Journal of Virological Methods, 157(2):161-167 (2009).

* cited by examiner

*Primary Examiner* — Benjamin P Blumel
(74) *Attorney, Agent, or Firm* — Arrigo, Lee, Guttman & Mouta-Bellum LLP

(57) ABSTRACT

The object of the invention are monoclonal antibodies against hemagglutinin of H5-serotype influenza viruses selected from the group comprising G-1-31-22, G-2-14-10, G-5-32-5, G-6-42-42, G-7-24-17 and G-7-27-18, having a broad application in immunoprophylaxis and immunotherapy of infections evoked by H5-serotype influenza viruses in humans and animals. The invention also provides hybridomas producing said antibodies, as well as compositions and diagnostic kits containing said antibodies for the detection and typing of H5-serotype influenza viruses and antibodies against H5-serotype influenza viruses in biological samples.

16 Claims, 15 Drawing Sheets

Specification includes a Sequence Listing.

| | rHA* - A/H5N1/ Qinghai | rHA* - A/H5N1/ India | rHA* - A/H5N1/ Vietnam | rHA* - A/H5N1/ Guiyang | rHA* - A/H5N2/ California | rHA** - A/H5N1/ Poland | rHA1* - A/H5N1/ Vietnam | rHA1* - A/H5N1/ HK/156 | rHA1* - A/H5N1/ HK/483 |
|---|---|---|---|---|---|---|---|---|---|
| G-1-31-22 | 100 | 111 | 110 | 121 | 70 | 70 | 76 | 81 | 47 |
| G-2-14-10 | 100 | 113 | 111 | 119 | 85 | 78 | 84 | 81 | 48 |
| G-5-32-5 | 100 | 106 | 110 | 120 | 102 | 87 | 89 | 73 | 55 |
| G-6-42-42 | 100 | 96 | 100 | 96 | 58 | 49 | 64 | 48 | 32 |
| G-6-42-71 | 100 | 97 | 102 | 101 | 58 | 46 | 60 | 43 | 26 |
| G-7-24-17 | 100 | 107 | 108 | 116 | 70 | 75 | 77 | 72 | 39 |
| G-7-27-18 | 100 | 109 | 110 | 118 | 92 | 81 | 82 | 70 | 50 |

Relative reactivity of mAb clones with H5-serotype influenza viruses

| | IV - H5N3 | IV - H5N1 | IV - H5N9 | IV- H5N2 |
|---|---|---|---|---|
| G-1-31-22 | 100 | 80 | 38 | 35 |
| G-2-14-10 | 100 | 61 | 34 | 27 |
| G-5-32-5 | 100 | 45 | 35 | 31 |
| G-6-42-42 | 100 | 54 | 11 | 30 |
| G-6-42-71 | 100 | 53 | 10 | 29 |
| G-7-24-17 | 100 | 54 | 39 | 24 |
| G-7-27-18 | 100 | 67 | 31 | 26 |

MONOCLONAL ANTIBODIES AGAINST HEMAGGLUTININ OF H5-SEROTYPE INFLUENZA VIRUSES AND THEIR USES, HYBRIDOMAS PRODUCING SAID ANTIBODIES, COMPOSITIONS AND DIAGNOSTIC KITS

SEQUENCE LISTING

The instant application contains a Sequence Listing which has been filed electronically in ASCII format and is hereby incorporated by reference in its entirety. Said ASCII copy, created on Jul. 29, 2019, is named Listing_PZ3293_ST25.txt and is 3,961 bytes in size.

OBJECT OF THE INVENTION

The object of the invention are monoclonal antibodies against hemagglutinin of H5 serotype influenza viruses and their broad application in diagnostics and immunotherapy of infections evoked by H5 serotype influenza viruses in humans and animals. The invention also provides hybridomas producing said antibodies, as well as compositions and diagnostic kits containing said antibodies for the detection and typing of H5 serotype influenza viruses and antibodies against H5 serotype influenza viruses in various biological samples.

BACKGROUND OF THE INVENTION

H5 Serotype Influenza Viruses

Influenza viruses (IV) belong to the Orthomyxoviridae family, which currently contains six different genera (ICTV 2014). Among them, Influenzavirus A genus is of the highest eidemiological importance. Influenza virus type A is surrounded by a protein-lipid envelope and contains genome in the form of single-stranded ribonucleic acid (RNA) with negative polarity, which is divided into eight segments and codes for 10 proteins.

Type A IV strains are classified according to the serotype of surface glycoproteins: hemagglutinin (HA) and neuraminidase (NA). Up till now, 18 HA serotypes and 11 NA serotypes (Szewczyk B. et al., 2014) have been identified. HA and NA proteins play an important role in virus replication cycle. By binding to sialic acid residues on host cell receptors, HA enables IV internalisation by endocytosis and then it mediates the fusion of viral envelope with cell membrane, which leads to a release of virus's genetic material into the cytoplasm and initiates process of its replication (Skehel J. J. and Wiley D. C., 2000). NA catalyses cleavage of glycoside bonds with sialic acid, which conditions release of the virus from attacked cells and therefore its spreading (Lamb R. A. and Choppin P. W., 1983).

Surface glycoproteins of IVs undergo gradual changes as a result of RNA polymerase errors and selection pressure from host immunological system. This phenomenon, referred to as antigen drift, leads to the escape of the virus out of immunological system control and usually causes limited illnesses, rarely epidemics. Greater and more rapid changes of viral antigens, referred to as antigen shift, are a result of genetic reassortation and can lead to pandemia. Variation makes IVs a real challenge for influenza diagnostics, prevention and treatment.

In birds, there are influenza viruses (AIVs) being a combination of 16 HA serotypes and 9 NA serotypes. There are 2 main type A IV serotypes are circulating in human population: H1N1 and H3N2. Influenza viruses are host-specific, so that AIVs usually do not infect humans. Among numerous AI viruses, low-pathogenic (LP) strains are dominant, causing mild infections. H5 and H7 serotypes influenza viruses, usually non-pathogenic in their natural hosts, which are wild birds, especially water birds, may become highly-pathogenic (HP) after transfer to an infection-prone population of domestic birds and by their intermediary become a risk for the health and life of humans. That was the case for HPAIV H5N1 strain.

Since the disease outbreak in 1996 at the goose-farm and human infections in 1997 in China (Xu X. et al., 1999), spreading of HPAI H5N1 viruses has been observed (Verhagen J. H. et al. 2015). The disease outbreaks among birds, often reaching epizootic scale, cause high animal mortality and force stamping out domestic birds. Cases of fatal infection of humans with H5N1 viruses are still reported. The risk of reassortation of circulating H5N1 AIVs with mammal viruses, leading to new strains capable of direct transmission between humans, is remaining.

During circulation and spreading of H5N1 viruses, HA genes were differentiating to the large number of genetic lines, referred to as clades (Verhagen J. H. et al., 2015). From 2009 onward, the emergence of the reassortants of H5-subtype HPAIVs, such as H5N2, H5N5, H5N6 and H5N8, has been noted. After their identification in 2014, H5N8 HPAIs are observed to spread rapidly in domestic birds population. As a result of reassortation with HPAIV H5N8, novel H5N2 HPIV emerged and was identified at the disease outbreaks at the chicken and turkey farms in Canada at the end of 2014 (Ip H. S. et al., 2015). In 2015, in the USA, H5N2 HPAIV caused high poultry mortality (Hvistendahl M., 2015).

H5 Hemagglutinin—Target Antigen for Monoclonal Antibodies

HA is synthesized as a single polypeptide chain, referred to as a HA precursor—HA0, containing signal sequence, HA1 and HA2 subunits separated by proteolytic enzyme cleavage site. HA0 cleavage is necessary to HA activation conditioning IV infectiveness, and protein susceptibility to digestion by proteolytic enzymes is one of the factors determining viral pathogenicity (Steinhauer D. A., 1999). In H5 HA proteins, cleavage site contains multiple basic amino acids, which makes the protein susceptible to the digestion by proteases active in most tissues, and the infection with H5 serotype IV has systemic nature.

The studies of structure of HA proteins of various serotypes, including H5, showed that antigenically-different hemagglutinins are structurally similar and show the same sub-domain organization (Ha Y. et al., 2002, Wilson I. A. Et al., 1981). The protein is composed of globular domain formed by HA1 subunit and stem domain formed mainly by HA2 subunit and N- and C-terminal amino acid sequences of HA1 subunit. Globular domain of HA contains antigen binding domain (RBD, through which virus binds host cell, whereas stem domain mediates fusion of viral and endosomal membrane. HA2 subunit within stem domain is responsible for HA trimer formation and stabilization, as well as its anchoring within viral lipid envelope, where the protein forms characteristic structures.

HA is the most variable IV antigen. This applies, in particular, to the globular domain. Mutation-susceptible protein domain contains epitopes for neutralizing antibodies usually having limited range of specificities within the serotype. In case of H5N1 HPAIV, weak cross-reactivity of those antibodies against antigenically distant viruses from different clades is observed. Antibodies directed against globular domain neutralize infectiveness of the viruses mainly by interfering with their binding to host cell receptors. Activity of RBD-binding neutralizing antibodies is observed in vitro as an inhibition of IV hemagglutinin activity.

In contrary to the globular domain-forming HA1 subunit, HA2 subunit, which forms an essential part of stem region, is relatively well conserved and contains epitopes for neutralizing antibodies of broad specificity range against different viral serotypes. Antibodies directed against stem domain neutralize viral infectiveness by blocking fusion of the membranes.

Use of Monoclonal Antibodies in Immunoprophylaxis and Immunotherapy

Currently, infections evoked by HPAIVs are controlled by using antiviral drugs and active or passive immunization. Immunoprophylaxis and immunotherapy are preferred due to the observed increase of IVs drug-resistance and side effects of pharmacotherapy. Preventive actions comprise mainly preventive vaccinations. Traditional vaccine production methods are long-lasting and would not be able to generate sufficient number of doses in case of pandemic risk. Immunization with the use of those vaccines is often associated with undesirable side effects. Alternative for conventional vaccines are DNA vaccines and subunit vaccines based on recombinant HA proteins. H5 HA proteins are produced mainly in eukaryotic cells, but also in bacterial cells. The main challenge for work on the development of subunit vaccines against influenza is the production of antigen having characteristics of native HA. Particularly important for vaccine HA quality is correctness of structure of HA1 subunit, where conformational epitopes for neutralizing antibodies are localized and protein oligomerization.

Anti-HA monoclonal antibodies (mAbs) can be use during the development of influenza vaccines and at various stages of their production and implementation. The first indicator of usefulness of HA proteins for the vaccine production are the results of the antigenicity tests carried out with the use of well-characterized antibodies (Chiu F. F. et al., 2009). Particularly useful in this regard are mAbs recognizing conformational, neutralizing HA epitopes. mAbs can also be used in studies of the level of HA proteins oligomerization, beside erythrocytes agglutination and fetuin binding tests. Using mAbs in affinity chromatography or immunoprecipitation, one can also isolate and purify H5 HA proteins. Antigens isolated and purified in this way can be used as components of prototype vaccines against IVs of H5 serotype, intended for initial evaluation of vaccine ability to evoke protective immunological response in animals. mAbs can also be used in the control of H5 HA vaccine stability, storaged separately or in immunogenic compositions. The most important use of serotype-specific mAbs associated with active immunisation is their use in so-called DIVA tests (*Differentiation of Infected From Vaccinated Animals*). Providing possibility to differentiate infected and vaccinated animals is the principal requirement for carrying out vaccinations against avian influenza (Suarez D. L., 2005).

Another way of preventing IV infections, but mostly of influenza treatment, is the use of mAbs for passive immunization. Those are mainly humanized antibodies or, preferably, antibodies produced de novo, as human mAbs. Predictably, neutralizing antibodies directed against variable and mutation-prone HA1 subunit of H5 hemagglutinin may not be effective against heterologous viral strains or antigen-drifted strains. In this context, it is of great importance to obtain neutralizing mAbs against epitops of HA1 subunit of HA, which are conserved among H5N1 IVs (Cao Z. et al., 2012, Du L. et al., 2013, Oh H. L. Et al., 2010, Wu R. et al., 2014). In the recent years, there are increasing reports about generating mAbs recognizing conservative epitopes in HA2 subunit of HA stem region, which show heteroserotypic neutralizing activity (Corti D. et al., 2011, Ekiert D. C. Et al., 2009, Okuno Y. et al., 1993, Sui J. et al., 2009).

PRIOR ART

Disadvantages of so Far Used Diagnostic Methods with the Use of Antibodies

Research on evolution, spreading and occurrence of novel HPAI virus strains of H5 serotype require using specific and reliable methods for early detection, IVs typing and strains identification (Petric M. et al. 2006). There is also a need for tests for recognizing infections evoked by AIVs of H5 serotype in humans, which could be used also for monitoring of viral infection development and/or evaluation of effectiveness of treatment regimen used. Objective difficulty, and simultaneously a challenge, is variability of IVs. Virus susceptibility to mutations should be taken into account already at the stage of reagent preparation and diagnostic tests development.

In influenza diagnostics, various conventional methods and techniques are used. Commonly accepted is method is reverse transcription polymerase chain reaction (RT-PCR). PCR-based diagnostics requires RNA extraction, use of specialist equipment, can be carried out by qualified personnel only and is expensive. In recognition of IV infection serological tests are also used: agar gel immunodiffusion (AGID), hemagglutination inhibition (HI) test and microneutralization (MN) test.

AGID test is reference screening test for detection of antibodies against IV in sera of domestic and wild animals. The results of this test are not reliable in case of some animal groups, such as water birds, which do not produce precipitating antibodies. Moreover, the test is prone to misinterpretation because of subjectivity of results reading.

HI test, recommended as reference test in animal serodiagnostics, is so-called "gold standard" in serotyping antibodies against IVs. This test is substantially restricted, as it shows maximum sensitivity in case of using homologous IVs, whereas using antigenically distant viral strain may lead to false negative results. HI test requires using erythrocytes preparation, which is obtained each time from blood of SPF animals. Additionally, when using non-chicken erythrocytes, it is necessary to use reagents removing from serum inhibitors of non-specific hemagglutination inhibition. HI test is not optimal in case of analysis of large number of serum samples, as it cannot be automated, and therefore is time-consuming and labor-intensive. Hemagglutination inhibition is evaluated visually, therefore the test result is subjective.

MN test, recommended in case of infections with H5N1 HPAIVs in humans, cannot be used in routine diagnostics. In requires using live viruses, therefore it is carried out in appropriate safety level laboratories by qualified personnel. In conclusion, MN test and other conventional diagnostics methods have substantial limitations.

Early influenza diagnostics uses various methods and immunological techniques to detect influenza viruses. Among them, there are tests based on ELISA (enzyme-linked immunosorbent assay), immunochromatography and tests with immunosensors. Those testes are easy to carry out and enable testing a large number of samples in relatively short time.

Yang M. et al. (2009) developed test based on sandwich ELISA method with the use of 2 different antibody clones. One of them was binding antibody, and the other—recognising antibody. In comparison to test using mAbs and polyclonal antibodies (pAbs), tests using 2 mAb clones are usually more specific and easier for standardization. Antibodies generated by hybridoma method with the use of H5N1 IV as immunogen, recognised conformational epitopes of HA, conserved among H5 serotype viruses. Antibodies had no HI-activity. The test did not show cross-reactions with IVs of serotypes different than H5, however, one of the tested H5N2 IV strains was detected with significantly reduced sensitivity.

Miyagawa E. et al. (2011), using hybridoma method and H5N1 IV as an immunogen, obtained 3 antibody clones recognising different conformational epitopes in the region of HA1 subunit of HA, identified as less prone to mutations. Antibodies showed no neutralizing activity. Three variants of immunochromatographic test were developed with the use of all clones obtained. The test specifically detected H5N1 and H5N3 IV strains. No reactivity with IV type A of serotypes different than H5 nor IV type B was found. However, none of the test variants detected IV strain H5N2.

Electrochemical biosensors for IV detection are a subject of recently published review (Grabowska I. et al., 2014). Jarocka U. et al (2014) developed immunosensor for the detection of peptides from viral HA with the use of monoclonal antibody Fab' fragment. Immunosensor detected recombinant hemagglutinin proteins based on HA1 subunit and HA ectodomain with H5N1 HPAIV antigen sequences. However, differences in the interactions were observed, depending on the length and sequence of HA protein.

In addition to influenza diagnostics based on virus detection, immunological methods and techniques are used for the detection of specific antibodies. Those methods are of special importance for the assessment of potential contact between animals and humans with IV. Among the tests for antibody detection, intermediate ELISA (iELISA) and blocking (bELISA) or competitive (cELISA) ELISA tests are applicable.

iELISA test are designed for testing of humans or specific animal species. They require using highly pure antigen and species-specific secondary antibodies, which are not always available. The major disadvantage of iELISA tests is their low specificity against tested IV serotype, which is a result of cross-reactions of antibodies induced by infections with viruses of different serotypes. In case of adults, specificity of an exemplary iELISA test for detection of antibodies against H5N1 AIV was only 62%, with the sensitivity level of 80% (Rowe T. et al., 1999).

In bELISA/cELISA tests, the key reagents are mAbs or their functional equivalents. In contrary to iELISA tests, bELISA/cELISA can be used to detect antigen-specific antibodies in sera of various origin. In influenza diagnostics, commonly used are bELISA/cELISA tests based on the use of mAbs against nucleoprotein (NP), which is highly conserved among type A IVs. Tests for the detection of antibodies against NP, used as an alternative for AGID tests, have screening character. Unlike them, bELIA/cELISA tests using serotype-specific mAbs against HA enable identification of infective virus serotype and, consequently, differentiation between infections evoked by HPIV and LPIV.

Yang M. et al. (2009), using hybridoma method and H5N1 IV as an immunogen, obtained antibody clone recognising conformational epitope in the HA1 subunit of HA and having no HI activity. Using obtained mAbs, cELISA test was developed and its efficacy was evaluated in chicken sera analysis. No cross-reactions with antisera against IVs of serotypes different than H5 was found. The test detected antibodies against IVs of H5 serotype, but test evaluation was carried out with the use of narrow range of anti-H5 positive sera.

Prabakaran M. et al. (2009), using hybridoma method and recombinant HA protein from bacterial expression system, obtained clone of antibodies recognizing linear epitope in HA1 subunit of HA. Epitope sequence for obtained mAbs was identified. Epitop turn out to be strongly conserved among IV H5N1 isolates from humans (100%) and birds (96.9%), and weakly conservative in HA of H5 serotype viruses of NA serotype other than N1 (54.3%). Antibodies showed no neutralizing activity. Using obtained mAbs, bELISA test was developed and its efficacy was evaluated in chickens and humans sera analysis. No cross-reactions with antisera against IVs of serotypes different than H5 was found. The test detected antibodies against HA of H5N1 viruses of different origin, but it did not provide detection of H5 serotype IVs other than H5N1.

Dlugolenski D. et al. (2010), using hybridoma method and H5 HA protein from mammalian expression system as an immunogen, obtained clone of antibodies reactive with H5N1, H5N2 and H5N3 LPIV and showing no HI activity. Using obtained mAbs, cELISA test was developed and analyses of chicken, turkey and duck sera were carried out. No cross-reactions with antisera against IVs of serotypes different than H5 was found. Antibodies against H5 HA were detected in different animal species with various specificity and sensitivity. The levels of diagnostic specificity and sensitivity of the test, specified for chicken sera, were low and were 63% and 66%, respectively.

For the construction of bELISA test, Postel A. et al. (2011) used mAb (ClonDiag) recognising linear epitopes of HA2 subunit in H5HA stem region, strongly conserved among different IV strains, including HP and LP, of H5 serotype: H5N1, H5N2, H5N3, H5N6, H5N9. Research carried out with sera from different groups of birds showed high level of diagnostic specificity (91.5%) and sensitivity (98.1%) of the test and its capability to detect antibodies induced in chickens by H5N1 HPAIV variant with antigen drift. However, significant cross reactivity of antisera specific against H2 serotype and, to a less extent, antisera specific against H1 and H6 serotypes was observed in the test. Predictably, the test could possibly detect novel IV variants of H5 serotype, while not providing clear distinction between antisera against H5 HA and against HA of H2, H1 and H6 serotypes.

Lebarbenchon C. et al. (2013) evaluated usefulness of FLUAc H5 (IDVet) test for detection of antibodies against H5 HA in water birds. It was found, that following introduction of modifications into manufacturer's protocol, test could provide valuable data regarding contact of analysed group of birds with IVs of H5 serotype. Using FLUAc H5 (IDVet) test, Postel A. et al. (2011) analysed serum samples of chickens vaccinated with antigenically distant H5N1 HPAIV. Large number of false negative results (7/9 of analysed samples) was obtained. It indicates limited ability of the test to detect novel H5N1 HPAIV strains.

Stelzer-Braid S. et al. (2008) evaluated diagnostic value of ELISA H5-HA antibody kit (Dialab), for which the manufacturer declared 100% specificity and 98% sensitivity level. It was shown, that the test is reliable when patients sera contained high levels of antibodies against H5 HA. It was also shown, that antibodies against seasonal H3N2 and H1N1 IVs may cross-react with H5 HA antigen, providing false positive results in the test being evaluated.

THE AIM OF THE INVENTION

Taking into account the risk for health and live of animals and humans, HPAIVs of H5 serotype are subject of epidemiological surveillance and various prophylactic and therapeutic strategies are developed against infections evoked by those viruses. Preventive activities are concentrated around high virus pathogenicity-determining H5 HA, which, at the same time, is the main target of antibodies neutralizing viral infectiveness. Monoclonal antibodies and antigen-binding proteins originated from them play an important role in those activities as efficient diagnostic reagents and therapeutic factors. Antigen variation makes influenza viruses a real challenge for influenza diagnostics, prevention and treatment.

The above presented solutions in the art indicate, that independently from method and technique of immunological test, a fundamental condition of correct diagnosis is the use of mAbs or their functional equivalents, which are specific against HA of H5 serotype and do not cross-react with HA of other serotypes. Only broad range of antibody specificities against H5 HA can provide identification of serotypes of infectious strains of various origins. It is desirable for mAbs to recognize native forms of H5 HA antigens. Wang S. F. Et al. (2009) obtained clones of antibodies reacting with denatured H5HA protein only. Usefulness of such mAbs is limited to narrow range of immunological methods.

Epitopes for diagnostically valuable mAbs should be localized in HA1 subunit, which determines virus serotype. Diagnostic applications of mAbs against HA1 subunit of H5 hemagglutinin, which are active in HI or MN tests, become problematic when epitopes for those antibodies are not conserved. Such mAbs and tests using them can loose the ability to detect infections evoked by IVs of H5 serotype in case of mutation of epitopes for those antibodies under conditions of immunological pressure. This, in turn, will be the reason why the test will not detect novel, mutated virus strains. On the other hand, in tests using mAbs recognizing conserved epitopes in HA stem region, some level of reactivity between serotypes is inevitable (Postel A. et al., 2011). Therefore, for the diagnostic effect it will be optimal to use mAbs or their functional equivalents specific against epitopes of HA1 subunit of HA, which are conserved among viruses of H5 serotype. Equally important is the availability of different clones of mAbs with desirable properties, so detection of currently circulating and novel IVs of H5 serotype can be achieved.

Thus, the aim of the invention is to provide instruments for effective immunoprophylaxis and immunotherapy of infections evoked by influenza viruses meeting the above criteria. The aim of the invention is to provide a set of antibody clones, which will meet the above requirements for mAbs with high diagnostic value. Unexpectedly, this aim is realized in the present invention and a solution for problems existing in the art is obtained.

DISCLOSURE OF INVENTION

Mouse hybridoma cell lines G-1-31-22, G-2-14-10, G-5-32-5, G-6-42-42, G-7-24-17, and G-7-27-18 were deposited on May 26, 2016, at the DSMZ-German Collection of Microorganisms and Cell Cultures GmbH, Inhoffenstraße 7B 38124 Braunschweig GERMANY, under the following accession numbers:

(i) G-1-31-22 under the number DSM ACC3292,
(ii) G-2-14-10 under the number DSM ACC3293,
(iii) G-5-32-5 under the number DSM ACC3294,
(iv) G-6-42-42 under the number DSM ACC3295,
(v) G-7-24-17 under the number DSM ACC3296, and
(vi) G-7-27-18 under the number DSM ACC3297.

The object of the invention are monoclonal antibodies against hemagglutinin of H5 serotype influenza viruses, which bind epitopes of H5 antigens, as well as their fragments and functional variants, selected from the group comprising:

(i) G-1-31-22 produced by mouse hybridoma cell line G-1-31-22 deposited with the DSMZ under the number DSM ACC3292,
(ii) G-2-14-10 produced by mouse hybridoma cell line G-2-14-10 deposited with the DSMZ under the number DSM ACC3293,
(iii) G-5-32-5 produced by mouse hybridoma cell line G-5-32-5 deposited with the DSMZ under the number DSM ACC3294,
(iv) G-6-42-42 produced by mouse hybridoma cell line G-6-42-42 deposited with the DSMZ under the number DSM ACC3295,
(v) G-7-24-17 produced by mouse hybridoma cell line G-7-24-17 deposited with the DSMZ under the number DSM ACC3296,
(vi) G-7-27-18 produced by mouse hybridoma cell line G-7-27-18 deposited with the DSMZ under the number DSM ACC3297.

Preferably, fragments of monoclonal antibodies include Fab, Fab', F(ab')2, Fv, $V_H$, $V_L$, single-chain antibody molecules consisting of $V_L$ and $V_H$ domains bound to each other by peptide linker.

Preferably, hemagglutinin is from influenza virus of H5 serotype, including H5N1, H5N2, H5N3 and H5N9. Preferably, monoclonal antibody according to the invention is conjugated with analytically detectable label, prodrug, drug, therapeutic agent, peptide, protein, enzyme, virus, lipid, PEG.

Another object of the invention are mouse hybridoma cell lines selected from the group comprising:

(i) G-1-31-22 deposited with the DSMZ under the number DSM ACC3292,
(ii) G-2-14-10 deposited with the DSMZ under the number DSM ACC3293,
(iii) G-5-32-5 deposited with the DSMZ under the number DSM ACC3294,
(iv) G-6-42-42 deposited with the DSMZ under the number DSM ACC3295,
(v) G-7-24-17 deposited with the DSMZ under the number DSM ACC3296 and
(vi) G-7-27-18 deposited with the DSMZ under the number DSM ACC3297.

Another object of the invention is pharmaceutical of diagnostic composition containing antibodies of the invention and an appropriate carrier of label.

Another object of the invention is the use of the composition containing monoclonal antibody of the invention for manufacturing of preparation for diagnosis and/or treatment of infections evoked by influenza viruses of H5 serotype.

Another object of the invention is the method for in vitro diagnosis of infections with influenza viruses of H5 serotype, that comprises contacting a biological sample with monoclonal antibody as defined above and detection of binding of said antibody with H5 serotype influenza virus or H5 hemagglutinin protein.

Another object of the invention is a diagnostic kit for the detection of infections with H5 serotype viruses, containing monoclonal antibody as defined above or its fragments, variants and immunoconjugates and reagents for the detection of antibodies or their functional equivalents bound with H5 serotype influenza virus or H5 hemagglutinin protein.

Another object of the invention is a diagnostic kit for the detection, quantification or semi-quantification of H5 serotype influenza viruses in biological samples, comprising monoclonal antibody of the invention.

The next object of the present invention is a diagnostic kit for the detection, quantification or semi-quantification of antibodies against H5 serotype influenza viruses in biological samples, comprising monoclonal antibody of the invention.

Preferably, antibodies in the kit are in the non-isolated form or are isolated and purified.

Preferably, the diagnostic kit is used in tests selected from the group consisting of: immunoenzymatic test, preferably bELISA H5, immunofluorescent, immunochemiluminescent, radioimmunological, immunochromatographic, immunodiffusion, immunoprecipitation tests, test with the use of immunosensors that can be used as so-called DIVA tests for the differentiation between infected animals and vaccinated animals.

Preferably, the diagnostic kit is used for the differentiation between infected animals and vaccinated animals as a so-called DIVA test.

The invention provides new monoclonal antibodies against hemagglutinin of H5 serotype influenza viruses: G-1-31-22, G-2-14-10, G-5-32-5, G-6-42-42, G-7-24-17 and G-7-27-18. The antibodies are designated analogically to the mouse hybridoma cell lines producing them. According to that, antibodies: G-1-31-22, G-2-14-10, G-5-32-5, G-6-42-42, G-7-24-17 and G-7-27-18 are produced by mouse hybridoma cell lines: G-1-31-22, G-2-14-10, G-5-32-5, G-6-42-42, G-7-24-17 and G-7-27-18, respectively. All clones obtained are mouse antibodies of IgG1 isotype. However, it does not limit the isotype of antibodies being the object of the invention. The isotype of the antibodies can be changed with the use of genetic engineering techniques known in the art. G-1-31-22, G-2-14-10, G-5-32-5, G-6-42-42, G-7-24-17 and G-7-27-18 mAbs specifically bind to the IVs of H5 serotype and HA proteins of H5 serotype.

The specificity of mAbs was examined with the use of H5 HA antigens with different properties. Among them, there were HA ectodomain-based recombinant proteins (rHA) from mammalian, baculovirus and bacterial expression systems, proteins based on HA1 subunit of HA (rHA1), obtained in mammalian cells and AIVs of H5 serotype. Most of the H5 HA antigens (13/14) showed characteristics of native protein. Conformational antigens contained HA sequences from twelve AIV strains of H5 serotype, wherein some of them were isolated from infected humans. This amount includes H5N3 (1 strain), H5N9 (1 strain), H5N2 (2 strains) and H5N1 viruses (8 strains), classified into five clades: 0, 1, 2.2, 4 and EA-nonGsGD. 0, 1, 2.2, 4 and EA-nonGsGD.

Obtained clones of mAbs: G-1-31-22, G-2-14-10, G-5-32-5, G-6-42-42, G-7-24-17 and G-7-27-18 recognized all conformational, glycosylated H5 HA antigens: rHA (6/6) and rHA1 (3/3) proteins from eukaryotic expression system and AIVs of H5 serotype (4/4). Under the testing conditions, for some clones (4/7), significant reactivity towards non-glycosylated bacterial H5 HA protein was also shown. None of the obtained clones of mAbs bound to non-conformational rHA protein. Produced mAbs bound to H5 HA antigens both before and after purification from the culture medium.

Monoclonal Abs: G-1-31-22, G-2-14-10, G-5-32-5, G-6-42-42, G-7-24-17 and G-7-27-18 recognized and bound to conformational epitopes of HA1 subunit of H5 HA antigens with diverse amino acid sequence of the HA1 subunit. The homology measured by amino acids identity between HA1 subunit of conformational HA antigens and HA1 subunit of immunogen used in the procedure of mAbs production, was from 99% to 88%. The particularly broad range of specificity of obtained antibodies indicates, that the epitopes for the obtained antibody clones are highly conservative among H5 serotype viruses.

The analysis of immunoreactivity profiles and peptide maps of Fab fragments of antibodies showed in accordance, that mAbs: G-1-31-22, G-2-14-10, G-5-32-5, G-6-42-42, G-7-24-17 and G-7-27-18 are distinct clones. Obtained mAbs recognize different epitopes specific for H5 serotype of hemagglutinin, therefore they may bind to one molecule of H5 HA protein monomer.

Monoclonal Abs: G-1-31-22, G-2-14-10, G-5-32-5, G-6-42-42, G-7-24-17 and G-7-27-18 do not have the ability to inhibit hemagglutination activity of IVs of H5 serotype, especially AIVs: H5N2 and H5N3. Therefore, the epitopes for the antibodies of the invention are not essential for the binding of IV to the host cell receptors, and thereby they are not undergoing mutations upon HI-type antibodies, which are known to inhibit viral infection. Predictably, the ability of the obtained mAbs to recognize IVs of H5 serotype may be preserved even in case of HA antigen change under conditions of immunological pressure. The confirmation of invariability of epitopes recognized by antibodies of the invention is the broad range of their specificity against H5 HA antigens.

Using twenty-one AIV strains representing HA serotypes other than H5, negative selection of the obtained antibody clones was performed. None of the antibody clones from the group comprising mAbs: G-1-31-22, G-2-14-10, G-5-32-5, G-6-42-42, G-7-24-17 and G-7-27-18 bound to IV serotypes: H1-H4 and H6-H16.

In summary, among six obtained clones of mAbs: G-1-31-22, G-2-14-10, G-5-32-5, G-6-42-42, G-7-24-17 and G-7-27-18, each recognizes different conformational epitope of HA1 subunit of HA, shows broad range of specificity against H5 serotype of HA and at the same time, does not cross-react with HA of H1-H4 and H6-H16 serotypes. Preferably, epitopes for those antibodies are probably highly conserved among IVs of H5 serotype and are not subjected to changes under conditions of HI-type antibodies inhibiting viral infection.

H5 HA antigen-binding molecules may take various forms. Binding molecules of the invention are mAbs: G-1-31-22, G-2-14-10, G-5-32-5, G-6-42-42, G-7-24-17 and G-7-27-18, which are intact mouse immunoglobulin molecules of IgG1 isotype, which contain fragments of constant region capable of crystallization (Fc) and antigen-binding regions (Fab). Such complete forms of molecules binding to H5 HA are build of two identical light chains (L) and two identical heavy chains (H), each of which contains constant and variable domains ($V_L$,$V_H$). Localized within variable parts of heavy and light chain, complementarity-determining regions (CDRs) are involved in specific epitope recognition and antigen-antibody complex formation.

The object of the invention are also fragments, variants and immunoconjugates of G-1-31-22, G-2-14-10, G-5-32-5, G-6-42-42, G-7-24-17 and G-7-27-18 mAbs, which maintain the ability to recognize and bind antigen of original antibody clones. Functional adequacy of different forms of binding molecules is expressed in their competitiveness with intact immunoglobulins for H5 HA antigen binding site.

H5 HA-binding antibody fragments include, but are not limited to: Fab, Fab', F(ab')2, Fv, scFv, $V_H$, $V_L$. Antibody fragments of the invention may be also multivalent or multispecific structures formed by antibody fragments, e.g. above-mentioned. Preferably, H5 HA-binding fragments can be single-chain variable fragments—scFvs, consisting of $V_L$ and $V_H$ domains bound to each other by peptide linker. scFv molecules can be part of, inter alia, multimers or minibodies having desired level of valency and specificity range. Functional fragments of antibodies are preferable particularly when they can be produced with higher yield, especially with the use of genetic engineering methods and/or when their use in some applications is more preferable than intact antibody molecules.

Functional mAb variants of the invention and their parts can be obtained by modifications of starting binding molecules, i.e. by changing the sequence and/or by forming derivatives. Those kinds of changes, introduced intentionally, are intended to improve properties of H5 HA antigen-binding molecules, such as affinity or avidity.

Each form of H5 HA antigen-binding molecule may be a part of immunoconjugate, which comprises at least one label facilitating its purification or detection with the use of known measurement techniques. Immunoconjugates comprising analytically detectable label may be used in diagnostics tests.

Monoclonal antibodies: G-1-31-22, G-2-14-10, G-5-32-5, G-6-42-42, G-7-24-17 and G-7-27-18 were obtained with the use of of conventional hybridoma technology. Present invention is associated with mouse hybridoma cell lines producing mAbs of the invention, designated as G-1-31-22, G-2-14-10, G-5-32-5, G-6-42-42, G-7-24-17 and G-7-27-18. Hybridomas secreting antibodies can be grown on a large-scale in vitro with the use of suitable media or in vivo in mouse peritoneal cavity. mAbs secreted by hybridomas can be used without purification, but preferably after removing components of culture medium or exudate, which may interfere or prevent their use in some applications. If needed, mAbs can be purified with the use various chromatographic methods, such as HPLC or Protein A or G affinity chromatography. Methods for antibody purification, including mAbs, are well known in the art.

In one embodiment, clones of mAbs of the invention were grown in vitro with the use of RPMI-1640 (Sigma-Aldrich) medium with addition of FBS, glutamine, sodium pyruvate and antibiotics. Antibodies were purified from hybridoma culture supernatants by affinity chromatography with the use of HiTrap Protein G HP (GE Healthcare).

Antibody production is not the only application of hybridomas: G-1-31-22, G-2-14-10, G-5-32-5, G-6-42-42, G-6-42-71, G-7-24-17 and G-7-27-18. Hybridomas of the invention are also a source of mRNA for synthesis of cDNA molecules coding obtained antibodies or their fragments, which can be then cloned and used in the expression of H5 HA antigen-binding molecules in heterologous systems. For the preparation of antibody-coding DNA sequences, their sequence variants or fragments, standard molecular biology techniques can be used.

Production of recombinant proteins in host cells, such as bacteria (e.g. *E. coli*), yeasts, cells of higher plants and animals, can be carried out according to methods well known in the art. For expression of fragments, such as Fab, F(ab')2, and especially Fv and scFv, bacterial and other microbiological systems may be used. For the production of larger H5 HA-binding molecules, including whole antibody molecules, eukaryotic systems, e.g. mammalian, can be used. Procedure for production of binding molecules of the invention by recombinant DNA methods would generally include: culturing recombinant host cells under conditions providing high expression level, product isolation from cell extract or, preferably, from culture medium and its purification.

Functional antibody fragments can be also produced in vitro by proteolytic digestion of intact immunoglobulins in the absence or presence of reducing agent, according to protocols known in the art. In one embodiment, Fab fragments of antibodies: G-1-31-22, G-2-14-10, G-5-32-5, G-6-42-42, G-7-24-17 and G-7-27-18 were obtained by ficin digestion of immunoglobulins with the use of commercial "Pierce™ Mouse $IgG_1$ Fab and $F(ab')_2$ Micro Preparation Kit" (Pierce/Thermo Scientific).

Immunoconjugates can be produced by chemical conjugation of antigen-binding molecules with labels. Techniques for conjugation of labels with antigen-binding molecules are well known in the art. Alternatively, immunoconjugates can be produced as fusion proteins containing binding molecules of the invention and a suitable label.

H5 HA antigen-binding molecules have special application in methods of H5 serotype IVs infection detection in animals and humans, and therefore are useful for diagnostic tests. In patients with identified infection, diagnostic tests containing binding molecules of the invention may be used also for monitoring of virus infection development and/or evaluation of effectiveness of applied treatment regimen.

Diagnostics of IV infections based on immunological methods detects viral particles or antibodies against viral antigens. According to that, two types of immunological tests are used in influenza diagnostics. H5 HA antigen-binding molecules can be used in both types of diagnostic tests. Taking into account a broad range of specificities against H5 HA, using binding molecules of the invention in diagnostics may provide identification of the infective strain. Test for detection of antibodies against H5 HA with the use of binding molecules of the invention can be also used as so-called DIVA test intended to distinguish infected animals from vaccinated animals.

Binding molecules of the invention may be used in immunological methods carried out in vivo, in situ or in vitro, by H5 serotype IVs localisation and/or quantification or semiquantification in the organism, tissues or cells, or in suitable biological samples. In another embodiment of the invention, H5 HA antigen-binding molecules may be used in methods of detection, quantification or semiquantification of antibodies against IVs, especially H5 serotype, in biological samples, such as blood serum or plasma. In those methods, mAbs or their functional equivalents compete with antibodies present in the sample for binding site on the antigen.

H5 HA antigen-binding molecules of the invention can be used in immunological test in various ways. For example, they can be used in an unisolated form or following isolation and purification. To obtain desired diagnostic effect, H5 HA antigen-binding molecules recognising particular epitope of the antigen may be used separately or together with molecule or molecules recognising other epitopes of the antigen. H5 HA antigen-binding molecules can bind the antigen in solution or suspension. Alternatively, those molecules can also be immobilized on solid surfaces and react with the antigen contained in liquid phase.

H5 HA antigen-binding molecules of the invention may be used in immunological tests as non-labelled proteins and/or in form of conjugates containing analytically detectable label. Labelling H5 HA antigen-binding molecules of the invention may facilitate their use in diagnostics and extend range of applications. Various labels are described in the art, which can be detected with the use of available measuring apparatuses, similarly to the conjugation methods for antigen-binding molecules and those labels. Immunoconjugates of H5 HA-binding molecules will contain labels suitable for specific detection techniques, analysis and/or methods used or techniques of immunological tests, in which they will find use.

H5 HA antigen-binding molecules of the invention may be used in the most of well-known techniques and methods of immunological tests. Examples include the following tests: immunoenzymatic, e.g. ELISA, immunofluorescent, immunochemiluminescent, radioimmunological, immunochromatographic, immunodiffusion, immunoprecipitation, based on the use of immunosensors. H5 HA antigen-binding molecules may be also used for immunohistochemical staining or sorting of fluorescently stained cells with the use of flow cytometer. Nevertheless, the above examples are not limiting to technique or method of the test, in which H5 HA antigen-binding molecules can be used. Because binding molecules of the invention recognize conformational epitopes, they cannot be used in Western blot-type tests, where molecules recognizing linear epitopes of antigens are used.

Preferably, the test for detection or quantification, or semiquantification of IVs of H5 serotype with the use of H5 HA antigen-binding molecules of the invention is sandwich-type ELISA test. Preferably, the test for detection or quantification, or semiquantification of antibodies against IVs of H5 serotype with the use of binding molecules of the invention are ELISA test in blocking (bELISA) or competitive (cELISA) format. In case of early diagnostics, it is preferable to use binding molecules of the invention e.g. in immunochromatographic tests or immunosensors for rapid and technically simple detection of IVs of H5 serotype.

In order to show possibilities for using binding molecules of the invention in diagnostics, BELISA H5 (IBA) test was developed and optimized for the detection of antibodies against H5 HA influenza viruses in chicken sera. One of the clones of antibodies of the invention was used in BELISA H5 test, i.e. mAb G-7-27-18, as key detecting antibody of the diagnostic test. For coating microtiter plates, H4 HA protein produced in baculovirus expression system (OET) was used. Assays were carried out in the presence of control samples. The control of maximum binding of mAb 7-27-18 with H5 HA antigen (mAb control) was obtained by carrying out analysis in the absence of serum. As negative control, normal chicken serum (Abcam) was used, whereas as strong and weak positive control—antisera of chickens vaccinated with inactivated AIVs of H5 serotype (x-OvO). The level of mAb 7-27-18-antigen binding inhibition by sera, expressed as percent, was calculated according to the formula: % inhibition=100−[($A_{450}$ sample/$A_{450}$ control mAb)×100].

Initial evaluation of diagnostic value for BELISA H5 test was conducted using samples previously classified as anti-H5 positive or negative based on the results of HI test. In the procedures of validation of test for diagnostics of IV infections, HI test is treated as a gold standard. The "cut-off" value was defined based on the results of assays for anti-H5-negative serum samples (mean value % inhibition+2× SD).

Obtained results suggest, that BELISA H5 test allows to distinguish between chickens vaccinated with H5 HA antigens and anti-H5-negative chickens. Importantly, antisera against AIVs of H1-H4 and H6-H16 serotypes do not cause cross-reactions in the developed test. BELISA H5 test would probably allow also unambiguous diagnostics of animals infected with IVs of H5 serotype, such as H5N1 HPAIV. In case of vaccinations against HPAIV with the use of H5 HA proteins, BELISA H5 test together with the test for detection of antibodies against other AIV antigens e.g. neuraminidase, could be used as so-called DIVA test designated for distinguishing infected animals from vaccinated animals.

Characterisation of BELISA H5 test was expanded to include an initial identification of the key validation parameters of the diagnostic test. Obtained results showed, that BELISA H5 test is characterized by satisfying reproducibility (RSD: 7.1%-10.0%) and high analytical specificity factors (Asp: 100%), as well as diagnostic specificity and sensitivity (Dsp: 97.6%; Dse 1: 98.0%; Dse 2: 99.1%).

The invention also includes diagnostic kits for identification of virus infection in animals and humans, especially those caused by IVs of H5 serotype. Diagnostic kits of the invention allow detection of IVs and antibodies directed against IVs, while simultaneously identifying serotype of infection virus.

Diagnostic kits of the invention can be produced in many ways. Besides binding molecules of the invention, which are crucial and characteristic for the recognition of infections with IVs of H5 serotype, the kit may also contain commercially available components of any other immunological diagnostic test.

Diagnostic kit of the invention contains at least one type of binding molecules of the invention. Those molecules can be mAbs selected from the group comprising antibodies: G-1-31-22, G-2-14-10, G-5-32-5, G-6-42-42, G-7-24-17 and G-7-27-18, but also their fragments, variants or immunoconjugates.

Diagnostic kit for detection of H5 serotype IVs of the invention can contain two different clones of antibodies selected from the group comprising mAbs: G-1-31-22, G-2-14-10, G-5-32-5, G-6-42-42, G-7-24-17 and G-7-27-18, but also their fragments, variants or immunoconjugates. For example, the test can be carried out using sandwich ELISA method. One antibody clone is used to cover microtiter plates, whereas the other, enzyme-conjugated clone is used for the detection of antigen-antibody complex by the reaction between labelling enzyme and its substrate, resulting in a detectable product.

Diagnostic kit for detection of antibodies against H5 serotype IVs of the invention can contain one clone of antibodies selected from the group comprising mAbs: G-1-31-22, G-2-14-10, G-5-32-5, G-6-42-42, G-7-24-17 and G-7-27-18 or its fragments, variants or immunoconjugates. It is also possible to use any composition of H5 HA binding molecules of the invention. For example, the assay may be conducted by ELISA method in blocking (bELISA) or competitive (cELISA) format. In bELISA/cELISA tests, H5 HA antigen-binding molecule or molecules are labelled directly (immunoconjugates) or indirectly (e.g. with the use of labelled secondary antibodies), which provides detectability of antigen-antibody complex.

Diagnostic kits of the invention contain instruments and reagents commonly used in immunological tests. When H5

HA antigen-binding molecules are components of diagnostic kits based on ELISA method, such kits contain additionally:

- plates coated with mAbs of the invention (sandwich-type ELISA) or H5 HA antigen (bELISA, cELISA), in which non-specific binding sites are completely saturated with the use of an appropriate blocking substance,
- buffers for plate washing, dilution of samples and reagents,
- substrate for an enzyme, as well as solution for enzymatic reaction inhibition.

Each diagnostic kit using H5 HA antigen-binding molecules contains also control samples: positive (PC) and negative (NC) control, which contain viral particles or antibodies associated with H5 serotype IV infection (PC) or do not contain them (NC). Reagents for diagnostic kit are provided in separate, labelled containers. Diagnostic tests contain also an instruction for conducting the test.

In one embodiment, diagnostic test of the invention—BELISA H5 (IBA) for detecting antibodies against H5 HA of influenza viruses in chicken sera, contains:

- MediSorp plates (NUNC) coated with recombinant H5 HA protein (OET) and blocked with the use of "Protein-Free T20 (PBS) Blocking Buffer" (Pierce/Thermo Scientific),
- concentrated solution of antibodies of the invention (7-27-18 mAb) in "Antibody Stabilizer PBS" (Candor Bioscience),
- concentrated solution of anti-mouse IgG antibodies labelled with HRP, specific to γ chain (Sigma-Aldrich) in "HRP-Protector" (Candor Bioscience),
- positive control, PC (anti-H5 positive chicken serum),
- negative control, NC (normal chicken serum),
- incubation buffer (BSA/PBS+Proclin 300),
- buffers for preparing working dilutions of antibodies of the invention and secondary antibodies, accordingly: Antibody Stabilizer PBS and HRP-Protector (Candor Bioscience),
- concentrated plate washing buffer (PBST+Proclin 300),
- TMB (Sigma-Aldrich),
- 0.5 M $H_2SO_4$.

Other uses of H5 HA antigen-binding molecules of the invention include their use in epidemiological studies for IV early detection and typing, as well as mapping of H5-specific epitopes in HA antigens.

Binding molecules of the invention are directed against different conformational epitopes of HA1 subunit, which are probably conserved in H5 HA proteins. It justifies their use for IV early detection and typing, and for molecular identification and characterization of H5 HA antigens (epitope mapping). This kind of studies provides important epidemiological data on the evolution and spreading of IVs, particularly H5 serotype, and the occurrence of novel strains. In the above applications the following mAbs can be used: G-1-31-22, G-2-14-10, G-5-32-5, G-6-42-42, G-7-24-17 and G-7-27-18, but also their fragments, variants or immunoconjugates.

Other applications of H5 HA antigen-binding molecules of the invention also include their use for monitoring of the quality of H5 HA antigens.

Binding molecules of the invention may be used for monitoring of the quality of H5 HA antigens intended for use as vaccine antigens or reagents in diagnostic tests. In particular, binding molecules of the invention may be used to check, whether HA antigen contains epitopes specific for H5 serotype in the proper conformation. Moreover, binding molecules of the invention may be used in the studies of the degree of oligomerization of H5 HA proteins. For example, such study may be conducted using sandwich ELISA-type test, in which one particular antibody clone, its variant or fragment is used in two forms, i.e. as non-labelled protein and as immunoconjugate comprising analytically detectable label. In this type of the test, non-labelled binding molecule of the invention adsorbed on microtiter plate captures the antigen. Antigen-antibody complex formed is detected by an immunoconjugate providing that the antigen contains more than one epitope recognized by the binding molecule, i.e. when it is in a form of dimer, trimer or oligomer. The degree of oligomerization is an important element of the evaluation of properties of HA proteins, particularly those which are intended for the production of vaccines against influenza.

Quality monitoring of H5 HA proteins, which are vaccine antigens or reagents in diagnostic tests, can be carried out with the use of mAbs: G-1-31-22, G-2-14-10, G-5-32-5, G-6-42-42, G-7-24-17 and G-7-27-18, but also their fragments, variants or immunoconjugates.

The main challenge for works on subunit vaccines against influenza, based on the use of HA, produced using genetic engineering methods, is to obtain viral antigen-like protein. Particularly important for vaccine HA quality is the correctness of structure of HA1 subunit, where conformational epitopes for neutralizing antibodies are localized. The first indicator of usefulness of HA proteins for the vaccine production are the results of the antigenicity tests carried out with the use of well-characterized antibodies. Novel mAbs recognize only conformational epitopes of HA1 subunit, probably conserved in H5 HA proteins. Therefore, they can be successfully used in the studies of properties of antigens for the production of vaccines against H5 serotype IVs, independently of original sequence of vaccine antigens. It is also envisioned to use the obtained antibodies in the control of H5 HA vaccine stability, storaged separately or in immunogenic compositions.

Another possible application for the obtained mAbs is their use to monitor quality of H5 HA proteins intended for use or already used as reagents in diagnostic tests. Novel mAbs show a broad range of specificities against H5 HA, thus they can be used to verify quality of the reagents, especially in those diagnostic tests, which are intended for the identification of the serotype of an infective strain.

In one embodiment, H5 HA protein from bacterial expression system was analysed before and after denaturation in reducing conditions with the use of G-6-42-42 and G-7-27-18 mAb by ELISA method. Those analyses revealed, that HA protein looses its normal conformation under denaturing and reducing conditions. The obtained results confirm usefulness of the produced antibodies for studying properties of newly obtained H5 HA proteins and for the detection of changes of those proteins during their storage.

Still another application of H5 HA antigen-binding molecules of the invention includes their use for an isolation or purification of HA proteins.

Binding molecules of the invention can be used for H5 HA antigen isolation or purification. For this purpose, standard techniques can be used, such as affinity chromatography or immunoprecipitation. HA antigens isolated and purified that way can be used as reagents in diagnostic tests or as components of prototype vaccines against IVs of H5 serotype, intended for initial evaluation of vaccine ability to evoke protective immunological response in animals.

The invention discloses the method for producing mAbs against HA of influenza viruses, showing broad range of specificities for HA of one particular serotype and showing no cross-reactivity with HA of other serotypes. Preferably, epitopes for desired mAbs produced according to the procedure of the invention, are strongly conserved within the serotype. The substance of the procedure of the invention is the use of recombinant protein with characteristics of native HA as an immunogen, the use of diverse group of HA antigens for the selection of antibodies for serotype specificity and the use of unique methods for clones differentiation. One of those methods is based on immunoreactivity profiles, and the other on the peptide maps of Fab fragments of the selected mAbs.

According to the method of the invention, mAbs can be obtained by hybridoma method firstly described by Köhler and Milstein (1975). The method comprises: immunization of mice with HA protein, isolation of lymphocytes from spleens of immunised animals, fusion of splenocytes with mouse myeloma cells and culturing, cloning and selection of hybridomas. In most of the described procedures for the production of mAbs against HA, IVs were used for immunization. What distinguishes procedure of the invention is the use of recombinant protein retaining characteristics of viral HA as immunogen. Preferably, the first dose of the antigen is administered in the form of emulsion with CFA, prepared using two syringes connected by the needle for emulsification.

According to standard procedure, obtained antibodies are selected for desired function and/or specificity, with the use of methods known in the art. Selection for the ability of antibodies to protect against IV infection is carried out with the use of HI and/or MN test. Thus selected antibodies are directed against those HA epitopes, which are under strong selective pressure during natural process of virus replication. As a result, target epitopes may change, which in turn leads to the limitation of the range of obtained mAbs. Identification of antibodies of desired specificity is realized with the use of immunological tests, such as ELISA, in which influenza viruses are usually used as antigens. The number of viral strains used is often limited and therefore selection gives weight only to the narrow range of HA protein variation.

What distinguishes procedure of the invention is that different HA antigen forms are used in antibodies screening, preferably with different properties giving an expected influence to the way in which epitopes are presented for the desired mAbs. Preferably, HA proteins used in immunoreactivity studies should show properties of viral antigen. It is also justified to broaden the panel of the antigens with proteins, which do not have the features of native HA, as this will enable differentiation of antibodies recognising conformational and linear epitopes of the antigen. According to the procedure of the invention, panel of HA antigens of a particular serotype, intended for immunoreactivity analysis, is characterized by a greater diversity of the homology for the immunogen used in the procedure of mAb preparation. For serotype-specific selection of antibodies it is necessary to perform negative selection with the use of HA antigens of the remaining fifteen serotypes.

In summary, strategy applied for the selection of mAbs increases probability of identification of those hybridomas, which produce desired serotype-specific antibodies having broad range of specificity. Moreover, the use of the test detecting functional properties of the antibodies will allow establishing, whether epitopes for those antibodies can be under immunological pressure during virus propagation.

At the final stage of the procedure, it is important to determine, how much the obtained clones differ from each other. This information can by obtain by comparison of sequences coding complementarity-determining regions of particular antibody clones. To obtain such data is labour-intense and takes a lot of time, because it requires not only to sequence CDR-coding genes, but also to verify the sequences by cloning and expression. Another way to discriminate selected mAbs is based on the studies on how they compete for the binding site on the antigen. In such tests, lowering of the binding of one antibody clone by the other antibody clone is interpreted as suggesting, that antibodies bind to the same epitope or epitopes, which are overlapping or are located close to each other within the antigen molecule.

In the disclosed procedure for obtaining serotype-specific mAbs, the differentiation of clones is based on the immunoreactivity profiles and peptide maps of Fab fragments of the generated antibodies. Applied differentiation methods are not so labor-consuming as establishing sequences of variable parts of antibodies.

Thus, the invention provides six different clones of mAbs: G-1-31-22, G-2-14-10, G-5-32-5, G-6-42-42, G-7-24-17 and G-7-27-18, each of which recognizes different conformational epitope of HA1 subunit of HA, shows broad range of specificity against H5 serotype of HA and at the same time, does not cross-react with HA of H1-H4 and H6-H16 serotypes. Preferably, epitopes for those antibodies are probably highly conserved among IVs of H5 serotype and are not subjected to changes under HI-type antibodies.

Antibodies of the invention were obtained by hybridoma method with the use of recombinant H5 HA protein of native HA properties as immunogen. The first vaccination of mice was done with the use of emulsion of H5 HA protein and CFA, prepared using two syringes connected by the needle for emulsification. Screening of mAbs for serotype-specificity was performed with ELISA method using different forms of H5 HA antigens having varied homology with the immunogen (positive selection) and IVs of serotypes other than H5 (negative selection). As a result of the selection, for further studies the following mAbs were chosen: G-1-31-22, G-2-14-10, G-5-32-5, G-6-42-42, G-6-42-71, G-7-24-17 and G-7-27-18. HI tests were performed showing that selected antibodies do not have hemagglutination inhibition activity.

Based on the studies on reactivity with H5 HA antigens, immunoreactivity profiles of obtained mAbs were created. Fc and Fab fragments of immunoglobulins were obtained as a result of ficin digestion, and then, after trypsinolysis, peptide maps of Fab and Fc fragments of particular clones were obtained. Of major importance for the identification of the obtained antibody clones was comparative analysis of peptide maps of antibody variable fragments responsible for antigen-binding, i.e. Fab fragments. Both of the applied differentiation methods gave consistent results. It was shown, that mAbs: G-1-31-22, G-2-14-10, G-5-32-5, G-7-24-17 and G-7-27-18 are different clones, whereas G-6-42-42 and G-6-42-71 mAbs represent one antibody clone, different from the other five clones.

Figure 1:
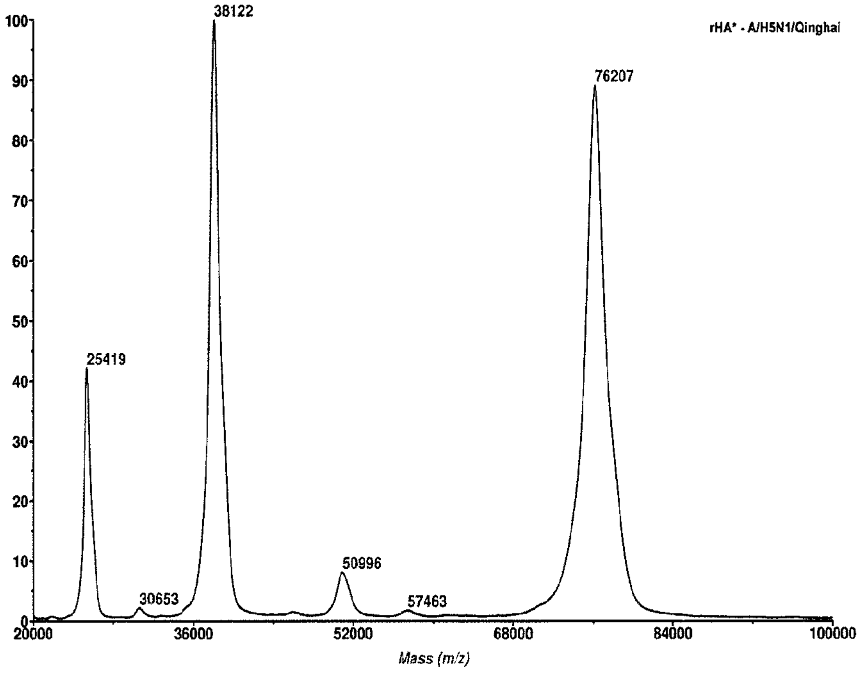
FIG. 1 shows mass spectrum of rHA-A/H5N1/Qinghai from (*) mammalian expression system. The protein (17-530 aa, ΔRRRKKR (SEQ ID NO: 13), 6×His (SEQ ID NO: 14)) was produced based on the sequence of HA of A/Bar-headed Goose/Qinghai/12/05 (H5N1) strain of AIV (ITC). Mass spectrum was obtained using MALDI TOF/TOF (4800 Plus, AB SCIEX) mass spectrometer.

The embodiment of the invention is presented below. The embodiments presented do not limit protection of the subject patent application.

Example 1

Procedure for Manufacturing of mAb Against Hemagglutinin of H5 Serotype Influenza Viruses.

Monoclonal antibodies were obtained using classic hybridoma method developed in mouse model by in vivo immunization. In this method, animals are vaccinated several times with the antigen. Splenocytes isolated from spleens of vaccinated animals are fused with myeloma cells in the presence of 50% PEG and 5% DMSO. Cell culturing in HAT differentiating medium causes splenocytes and non-fused myeloma cells to die, and only hybridomas cells survive. During cloning, individual hybridomas are isolated and supernatant from hybridoma cultures established from a single hybridoma is tested for the presence of antigen-specific antibodies of a given class (isotyping). Hybridoma clones can be cultured in vitro or in an exudative cancer.

In the first stage of the procedure for mAb manufacturing, mice immunisation was conducted. As the immunogen, purified H5 HA protein (17-530 aa, ΔRRRKKR (SEQ ID NO: 13), 6×His (SEQ ID NO: 14)) was used produced in mammalian expression system based on the HA sequence from A/Bar-headed Goose/Qinghai/12/05 (H5N1) strain of AIV by Immune Technology Corporation (ITC). rHA-A/H5N1/Qinghai was previously analysed using mass spectrometry, ELISA assays for antigenicity analysis and HA protein oligomerization, and hemagglutination test. Method for carrying out the tests and their results are shown in Example 2. In Example 2, properties of rHA-A/H5N1/Qinghai immunogen are also described that indicate its usefulness in the procedure of manufacturing mAb against H5 HA. According to the standard method, production of antigen-specific mAbs comprises: mice immunisation, fusion of splenocytes with mouse myeloma cells and hybridoma culture, cloning and selection.

Mice Immunization

Five, 6-weeks old female Balb/c mice were vaccinated subcutaneously with rHA (10 μg/mouse) at two sites in the neck with Complete Freund Adjuvant (CFA). Emulsion of antigen with CFA in a 1:1 ratio (v/v) was prepared using two 1-mL syringes connected with needle for emulsification (Popper & Sons). Immunologically preferable consequences of using 2 syringes method for the preparation of the vaccine in a form of emulsion and the advantage of this method over other emulsification techniques is described in the literature (Koh Y. T. et al., 2006). Vaccination was conducted under anaesthesia. Another two doses of antigen, 10 μg each, were given intraperitoneally in a form of PBS. The second vaccination was conducted 2 weeks after the I dose, and the third vaccination was performed 3 weeks after the II dose. The fourth vaccination was performed 17 days after the III dose by intravenous administration of rHA (10 μg/mouse) in PBS.

Control of Titer of Antibodies Against H5 HA in Serum

Eleven days after the administration of the III dose and nine days before the fusion, blood was collected from the retro-orbital sinus from each of the immunized mice using heparinized capillary tubes. Serum obtained after blood centrifugation was aliquoted and frozen at −20° C. In order to titrate antibodies against H5 HA, serum samples were analysed by ELISA using HA protein used for animal vaccination (rHA-A/H5N1/Qinghai). rHA-A/H5N1/Poland of HA sequence from A/swan/Poland/305-135V08/2006 (H5N1) strain of AIV, produced by Oxford Expression Technologies (OET) in baculovirus expression system, was also used in the tests. The protein characterized by high homology to immunogen was described in detail in Example 3. To develop the plates, anti-mouse IgG antibodies specific to γ were used. Using highly specific secondary antibodies in the tests enabled identification of H5-specific antibodies of IgG class-only, and thus an appropriate evaluation of animals' response to the vaccination.

ELISA tests were performed with the use of microtitration plates (NUNC). rHA-A/H5N1/Qinghai (ITC), diluted in PBS do 5 μg/mL, was applied to MaxiSorp plates, whereas rHA-A/H5N1/Poland (OET, series 1), diluted in PBS to 7 μg/mL, to MediSorp plates. Plates with the antigens were incubated overnight at 2-8° C. Non-specific binding sites on the plates were blocked with the use of 10% FBS/PBS. Serum samples from immunised mice were tested as series of 2-fold dilutions in PBS. Negative control was serum samples from non-immunized mice. Dilution buffer was the control for non-specific binding of secondary antibodies (BLK sample). Tested and control samples were incubated on the coated plates for 2 hours at room temperature. Plates were developed by 1-hour incubation at 37° C. with HRP-labelled anti-mouse IgG antibodies, specific for γ chain (Sigma-Aldrich). Secondary antibodies were diluted 1:1000 in 2% BSA/PBS. TMB (Sigma-Aldrich) was used as a substrate for horseradish peroxidase. Reaction was inhibited using 0.5 M solution of $H_2SO_4$. Absorption of samples was read at λ=450 nm. Titer of IgG-class antibodies against H5 HA was defined as serum dilution, at which absorption ($A_{450}$) reaches value ~1.0.

Hybridomas Preparation, Culture and Cloning

Immunized mice were sacrificed by cervical dislocation 3 days after intravenous administration of the last boosting dose. Spleens were collected in sterile manner and splenocytes were isolated. Following cells collection and centrifugation (10 min, 1000 rpm, 5° C.), the pellet was resuspended in complete RPMI-1640, the cells were counted and their viability was evaluated in Thoma camera in the presence on trypan blue. Cells of the mouse myeloma cell line SP2/0 (ATCC) were cultured in HT medium do logarithmic phase, centrifugated at 1000 rpm, resuspended in RPMI-1640 and live cells were counted.

For the fusion, splenocytes isolated from the spleen of mouse with the highest titer of IgG class of antibodies against H5 HA in serum were chosen. Spleen and myeloma cells in RPMI-1640 were mixed in 2:1 ratio. Following centrifugation and precise removing of the supernatant, about 1 mL of the following solution was added for 1 min: 50% PEG 1500, 5% DMSO in PBS without calcium and magnesium ions, at 37° C., with gentle stirring of the pellet. The fusion was stopped by adding heated RPMI-1640 medium with the addition of antibiotics (streptomycin—50 μg/mL, penicillin—50 U/mL)—first 4 mL slowly, dropwise, and the next 16 mL—rapidly. Cell suspension was centrifugated for 10 min at 1000 rpm, 5° C. The pellet was resuspended in HAT medium and transferred into eight 96 well plates containing a layer of mouse peritoneal macrophages. After a week of incubation at 37° C. in atmosphere of 5% $CO_2$, cell cultures were feed with HAT medium, and in the following week—with HT.

Cloning of hybridomas was performed by further dilutions. Cell suspensions were prepared containing 10 and 5 cells/mL, respectively. Each of the suspensions was aliquoted (100 μL/well) in 96 well plate with a layer of macrophages. Wells were observed and those with clones originating from 1 cell were marked.

After the fusion, hybridomas were cultured in RPMI-1640 medium supplemented with 20% FBS, containing 2 mM glutamine, 2 mM sodium pyruvate, antibiotics (streptomycin—50 μg/mL, penicillin—50 U/mL) and 100 μM hypoxanthine, 2.5 μM aminopterin and 16 μM thymidine (HAT differentiating medium) or 100 μM hypoxanthine and 16 μM thymidine (HT medium), as required. During cloning, RPMI-1640 medium with the addition of 20% FBS, containing 2 mM glutamine, 2 mM sodium pyruvate and antibiotics (streptomycin—50 μg/mL, penicillin—50 U/mL) was used. Further hybridoma culture was carried out in medium having the same composition as in cloning medium, with the exception of FBS concentration (10%). For freezing obtained clones in liquid nitrogen, complete RPMI-1640 medium containing 30% FBS and 10% DMSO was used. Cell number and viability were determined using trypan blue solution in saline. Hank's salt solution without calcium and magnesium was used for the isolation of peritoneal macrophages. All of the reagents used were company tested regarding to the lack of toxicity for cell cultures and were from Sigma-Aldrich or Gibco.

Hybridoma Selection

Hybridoma culture supernatant was analysed for the presence of H5 HA-specific antibodies. The analysis was performed by ELISA. Initial hybridoma selection was performed using rHA—A/H5N1/Qinghai (ITC) and rHA—A/H5N1/Poland (OET) with sequence very similar to the immunogen sequence. Further hybridoma selection was carried out by determining specificity of the generated antibodies against recombinant H5 HA proteins based on hemagglutinin ectodomain (rHA) or HA1 subunit (rHA1) with varied homology for the immunogen, which were produced in mammalian expression system (ITC). In ELISA carried out using supernatants from cultures of non-cloned hybridomas, protein with HA sequence of six H5-serotype AIV strains was used. After cloning, selection of mAbs was performed using rHA or rHA1 based on the HA sequence of nine H5-serotype AIV strains. For positive selection of cloned hybridomas H5N1, H5N2, H5N3 and H5N9 IVs (x-OvO) were also used. At each step of the procedure, antibody isotyping was performed.

Clones of mAbs with the highest diagnostic value chose as a result of selection were purified from hybridoma supernatants using affinity chromatography. Antibodies were characterized using mass spectrometry, ELISA with recombinant H5 HA proteins (rHA, rHA1) and IVs of H5 serotype. Tests using IVs of serotypes other than H5, i.e. H1-H4 and H6-H16 were also used. In order to evaluate the ability of generated mAbs to inhibit hemagglutination, HI testes were carried out.

Antigens and tests used for the selection of hybridomas generating antibodies against H5 HA, as well as the method for carrying out antibody isotyping are described in great detail in Example 3. Antigens and tests used for further selection of serotype-specific antibodies, as well as hybridomas generating those antibodies are described in Example 4. Results of mAbs selection at particular stages of the procedure are described in Example 5. Properties of selected mAbs are described in Examples 6-10.

Example 2

Immunogen Properties

Commercially available mAbs against H5 HA are usually obtained using hybridoma method with IVs for animal vaccination (ABR/Thermo Scientific, Acris Antibodies, USBiological). In the production of mAbs, recombinant HA proteins are also used (USBiological). In order to generate antibodies with high application value in prevention, therapy and diagnostics of IV infections, antigen having viral HA-like properties has to be used. In case of production of mAbs for use in influenza diagnostics, it is desirable for the antigen to contain primarily well preserved epitopes specific for the serotype. Therefore, in the procedure of production of mAbs specific for H5 HA serotype by hybridoma method, it was of key importance to use an immunogen fulfilling above requirement.

Before starting manufacturing procedure for mAbs against H5 HA, information on commercially available H5 HA antigens was collected. Products from Immune Technology Corporation were selected, wherein the company specialises in the production of viral antigens and anti-viral antibodies for diagnostics, monitoring and therapy of viral infectious diseases. At ITC, recombinant H5 HA proteins from several strains of H5N1 virus, as well as HA of serotypes other than H5, are available. Mammalian expression system is used for antigen production. Usefulness of purified, recombinant H5 HA proteins for selection of antibodies and hybridomas producing them, was tested using ELISA for antigenicity and oligomerization studies, which is described in Example 4. In the present Example, results of testing the properties of recombinant H5 HA protein used as an immunogen are shown.

For the production of mAbs against H5 HA with the use of hybridoma method, recombinant protein was selected with HA sequence of A/Bar-headed Goose/Qinghai/12/05 (H5N1) strain of AIVs (ITC). The protein, which was expressed in mammalian cells without signal sequence, transmembrane and cytoplasmic domain, as well as cleavage region (ΔRRRKKR (SEQ ID NO: 13)), was the fragment of HA (17-530 aa) containing HA1 subunit, part of HA2 subunit and histidine tail—6×His (SEQ ID NO: 14) at the C-terminus. Due to the eukaryotic origin, produced antigen was a glycoprotein, just as native HA. According to the specification, HA protein of molecular weight ~75 kDA (SDS-PAGE) and at least 95% purity, is present mainly in a form of trimers/oligomers. To evaluate its usefulness in the manufacturing procedure for mAbs against H5 HA, the protein, hereinafter described as rHA-A/H5N1/Qinghai, was subjected to analysis using mass spectrometry, ELISA (for studies of HA proteins antigenicity and oligomerization) and hemagglutination test.

Mass Spectrum of rHA-A/H5N1/Qinghai

The mass spectrum of rHA-A/H5N1/Qinghai was obtained using MALDI TOF/TOF (4800 Plus, AB SCIEX) mass spectrometer. Before performing mass spectrometry, the samples were purified using ZipTip®$_{C4}$ (Millipore) according to the procedures included in the manufacturer's instruction: "User Guide for Reversed-Phase ZipTip". The matrix was α-cyano-4-hydroxycinnamic acid (Fluka) in 5 mg/mL concentration dissolved in 0.1% trifluoroacetic acid containing 50% of acetonitrile. Mass spectra were measured in the linear mode (MS Linear Positive Ion), in the range of 20-100 kDa. External calibration was achieved with ProMix3 mixture (LaserBio Labs). Method for data acquisition was established in MALDI TOF/TOF—4000 Series Explorer software. Mass spectra of rHA-A/H5N1/Qinghai were processed using Gaussian filter and the procedure for signal detection with the use of Data Explorer Software (V4.9).

FIG. 1 shows mass spectrum of rHA-A/H5N1/Qinghai. Molecular weight signals of 76 kDa and 38 kDa represent tested HA protein and correspond to singly- and doubly-ionized samples, respectively. Molecular weight of rHA-A/H5N1/Qinghai, calculated with the use of MALDI TOF/TOF mass spectrometer (MS), is 76 kDa and due to the glycosylation, it is ~18 kDa higher than the weight calculated based on the amino acid composition using GPMAW 8.2 software (Lighthouse).

Antigenicity of rHA-A/H5N1/Qinghai rHA-A/H5N1/Qinghai antigenicity studies were conducted using commercially available mAbs and pAbs against H5 HA of influenza virus. Based on the specifications, a list of used antibodies was prepared and is presented below.

List A The list of monoclonal and polyclonal antibodies used in the studies of HA protein antigenicity.

| | Name | Origin Cat. no. | Immunogen | Type Isotype | Application |
|---|---|---|---|---|---|
| Monoclonal antibodies (mAbs) against H5 HA<br>Recognise H5 HA in HI test, react with H5N1, H5N2 and H5N9 influenza viruses, do not cross-react with IVs of other HA serotypes (H1, H2, H3, H4, H6, H7, H8, H9, H10, H11, H12, H13, H14 and H15). | | | | | |
| mAb 1 | Influenza A Hemagglutinin H5 (Avian H5N1) | USBiological, 17649-41B | Purified avian influenza virus type A (H5N1) | mAb IgG2a* | HI, iELISA DB |

-continued

List A The list of monoclonal and polyclonal antibodies used in the studies of HA protein antigenicity.

| | Name | Origin Cat. no. | Immunogen | Type Isotype | Application |
|---|---|---|---|---|---|
| Specific for H5 HA protein of influenza A virus [A/Vietnam/1203/04 (H5N1) strain], do not cross-react with IVs of other HA serotypes, react with H5N1 influenza viruses, representatives of different clades and subclades. | | | | | |
| mAb 2 | Influenza A, Avian, H5N1A/Vietnam/1203/04 Hemagglutinin (Bird Flu) | USBiological, 17649-42C | HA of influenza virus A/Vietnam/1203/04(H5N1) | mAb IgG2a* | HI, VN, ELISA, IP, IHC, WB |
| Recognize H5 HA in HI test. | | | | | |
| mAb 3 | Influenza A Hemagglutinin H5 (Avian H5N1) | USBiological 17649-42D | Purified avian influenza virus type A (H5N1) | mAb IgG2a* | HI ELISA |
| Detect influenza A H5 antigen in viral samples. | | | | | |
| mAb 4 | Anti-Influenza A H5 Antigen Monoclonal Antibody | ABR/Thermo Scientific MA1-81927 | Purified avian influenza virus type A (H5N1) | mAb IgG2a* | ELISA |
| React with H5 HA in HI test, react with H5N1, H5N2 and H5N9 influenza viruses, do not cross-react with IVs of other HA serotypes (H1, H2, H3, H4, H6, H7, H8, H9, H10, H11, H12, H13, H14 and H15). | | | | | |
| mAb 5 | Monoclonal Antibody to Influenza A (Hemagglutinin H5) H5N1 - Purified | Acris Antibodies AM00942PU-N | Purified avian influenza virus type A (H5N1) | mAb IgG2a* | HI, iELISA, DB |
| mAb 6 | Monoclonal Antibody to Influenza A (Hemagglutinin H5) H5N1 - Purified | Acris Antibodies AM00944PU-N | Purified avian influenza virus type A (H5N1) | mAb IgG2a* | HI, iELISA, DB |
| mAb 7 | Monoclonal Antibody to Influenza A (Hemagglutinin H5) H5N1 - Purified | Acris Antibodies AM00945PU-N | Purified avian influenza virus type A (H5N1) | mAb IgG2a* | HI, iELISA, DB |
| mAb 8 | Monoclonal Antibody to Influenza A (Hemagglutinin H5) H5N1 - Purified | Acris Antibodies AM00941PU-N | Purified avian influenza virus type A (H5N1) | mAb IgG2a* | HI, iELISA, DB |
| Policlonal antibodies (pAbs) against H5 HA React with H5 HA of human and avian H5N1 influenza viruses. Cross-reactivity to other HA not tested. | | | | | |
| pAb 1 | Anti-HA (H5N1) (Bar headed goose/Qinghai/ 1A/05) | ITC IT-003-005G | Hemagglutinin of influenza A virus (H5N1) (1-345 aa) (A/Bar-headed Goose/Qinghai/ 12/05(H5N1)) | pAb rabbit IgG* | WB itd. |
| React with HA and HA2 subunit (H5N1). Cross-reactivity against other serotypes not tested. | | | | | |
| pAb 2 | Anti-HA2 (H5N1) | ITC IT-003-010 | HA2 protein (H5N1) (347-523 aa) (A/VietNam/1203/2004(H5N1)) | pAb rabbit IgG* | WB itd. |

*purified,
HI—hemagglutination inhibition test,
iELISA—indirect ELISA (enzyme-linked immunosorbent assay),
DB—dot blot,
VN—virus neutralization test,
IP—immunoprecipitation,
IHC—immunohistochemistry,
WB—Western blot,
ITC—Immune Technology Corporation Monoclonal antibodies were from USBiological (3 clones), ABR/Thermo Scientific (1 clone) and Acris Antibodies (4 clones). mAbs were obtained using purified H5N1 AIVs (7 clones) or recombinant protein with the HA sequence from A/Vietnam/1203/04 (H5N1) strain (1 clone) as immunogens. According to specifications, antibodies described as mAb 1 and mAb 5-8 recognize H5 HA in HI test, bind to H5N1, H5N2 and H5N9 IVs and do not cross-react with HA of H1-H4 and H6-H15 serotypes. Specificity of other mAb clones is described as the ability to recognize H5 HA in viral samples (mAb 4) or HI test (mAb 3). According to the manufacturer's information, antibodies designated as mAb 2, are specific against HA of A/Vietnam/1203/04 (H5N1) strain, react with H5N1 IVs from various clades and subclades and do not cross-react with HA of serotypes other than H5. Specifications for all mAbs used indicate, that antibodies recognize conformational epitopes.

In the immunoreactivity assays, polyclonal antibodies against HA1 and HA2 subunit of H5 hemagglutinin were also used. Antibodies, described hereafter as pAb 1 and pAb 2, were obtained using HA1 (1-345 aa) from A/Bar-headed Goose/Qinghai/12/05 (H5N1) strain and fragment of HA2 subunit (347-523 aa) of A/VietNam/1203/2004 (H5N1) strain (ITC) as immunogens, respectively. According to specifications, pAb 1 and pAb 2 may be used in Western blot-type assays. It can be expected, that pAbs against HA will recognize both conformational epitopes and linear proteins.

The assays for the reactivity of rHA-A/H5N1/Qinghai immunogen with commercial antibodies were carried out by ELISA using polystyrene PolySorp, MaxiSorp, MediSorp and MultiSorp (NUNC), as well as Ni-NTA plates (Qiagen). Polystyrene plates were coated with rHA in PBS at 5 μg/mL overnight at 2-8° C. Non-specific binding sites on the plates were blocked with the use of 10% FBS/PBS. HA protein diluted in 1% BSA/PBS to 1 μg/mL concentration was applied on Ni-NTA plate. In order to control the level of unspecific binding of antibodies, some wells were filled in with 1% BSA/PBS and incubated overnight at 2-8° C., in parallel to the antigen-containing wells. Because Ni-NTA plates from Qiagen are pre-blocked, those tests were carried out without blocking stage. Plate-bound antigen was tested using mAbs and pAbs against H5 HA, enumerated on the List A. Antibodies diluted to 1 μg/mL in 2% BSA/PBS, were incubated in coated plates overnight at 2-8° C. Whole-molecule specific HRP-labelled pAbs against mouse IgG (Sigma-Aldrich) were used for the detection of antigen-bound mAb. γ-chain specific, HRP-labelled mAbs against rabbit IgG (Sigma-Aldrich) were used for the detection of antigen-bound pAb. Secondary antibodies were diluted 1:1000 with 1% BSA/PBST and incubated with the plates for 30 min (polystyrene plates) or for 45 min (Ni-NTA plates) at room temperature. TMB (Sigma-Aldrich) was used as a substrate for HRP. Reaction was stopped using 0.5 M (polystyrene plates) or 1.25 M (Ni-NTA plates) solution of $H_2SO_4$. Absorption of samples was read at $\lambda$=450 nm.

Figure 2:
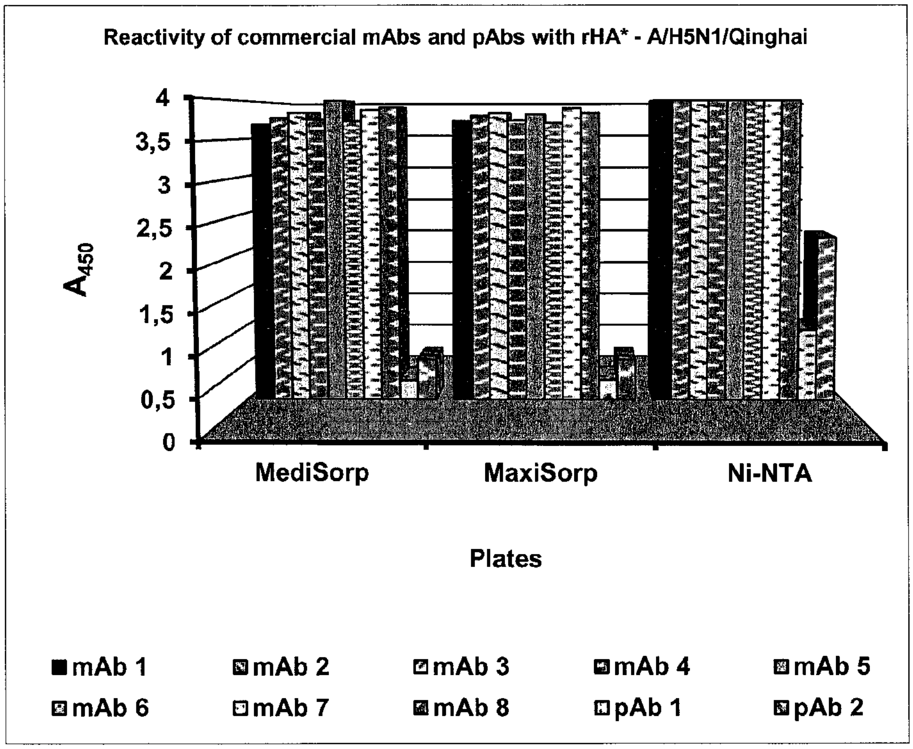
FIG. 2 shows the results of antigenicity analysis of rHA-A/H5N1/Qinghai from (*) mammalian expression system. The protein (17-530 aa, ΔRRRKKR (SEQ ID NO: 13), 6×His (SEQ ID NO: 14)) was produced based on the sequence of HA of A/Bar-headed Goose/Qinghai/12/05 (H5N1) strain of AIV (ITC). The tests were carried out using ELISA on MediSorp, MaxiSorp (NUNC) and Ni-NTA (Qiagen) plates. Commercially available mAb against H5 HA (USBiological, ABR/Thermo Scientific, Acris Antibodies) and pAbs against HA1 (pAb 1) and HA2 (pAb 2) subunit of the antigen (ITC) were used in the tests.

The results of rHA-A/H5N1/Qinghai antigenicity studies performed on MediSorp, MaxiSorp and Ni-NTA plates using commercial anti-H5 HA antibodies are shown in FIG. 2. HA was recognized by all antibodies used, what leads to the conclusion that the antigen comprises very well preserved conformational epitopes of HA1 subunit of H5 hemagglutinin and fragment of HA2 subunit. Moreover, these results suggest, that there are correctly formed epitopes recognized by HI antibodies in HA1 subunit of rHA-A/H5N1/Qinghai, what indicates the potential of the protein for the induction of hemagglutination-inhibiting antibodies.

rHA-A/H5N1/Qinghai Oligomerization

Presence of oligomeric forms in rHA-A/H5N1/Qinghai preparation was tested by sandwich ELISA method, using the same clone of mAb (B513M), designated as mAb 8 (Acris Antibodies), for coating and developing microtiter plates. Detecting antibodies were HRP-labelled by service company (Acris Antibodies).

To perform the test, MaxiSorp plates (NUNC) were coated with mAb 8 (Acris Antibodies, Cat. No. AM00941PU-N) in PBS (1 μg/mL), overnight, at 2-8° C. Non-specific binding sites on the plate were blocked with the use of 2% BSA/PBS. Next, different samples of rHA-A/H5N1/Qinghai protein, prepared as a series of 2-fold dilutions ranging from 10 μg/mL to 0.009 ng/mL in 2% BSA/PBS, and BLK sample (2% BSA/PBS), were loaded on the plate to control the level of unspecific binding. Plates were incubated overnight at 2-8° C. HRP-labelled mAb 8 (Acris Antibodies, Cat. No. AM00941HR-Cus) was used to detect oligomeric forms of HA protein. Antibodies were diluted 1:500 in 2% BSA/PBS and incubated on the plate for 1 h at 37° C. TMB (Sigma-Aldrich) was used as a substrate for HRP. Reaction was inhibited using 0.5 M solution of $H_2SO_4$. Absorption of samples was read at $\lambda$=450 nm.

Figure 3:
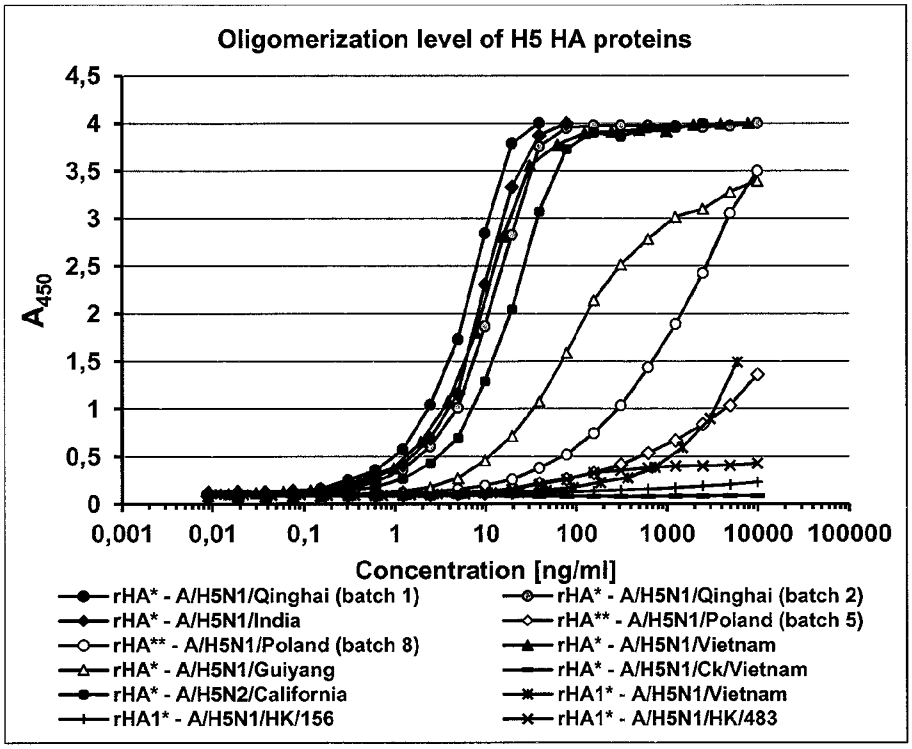
FIG. 3 shows the results of oligomerization status analysis for recombinant H5 HA proteins with sequences of various H5 serotype IV strains. Proteins based on ectodomain (rHA) or HA1 subunit (rHA1) of the antigen were produced in (*) mammalian (ITC) or (**) baculovirus (OET) expression system. The tests were carried out using sandwich ELISA with non-HRP-labelled and HRP-labelled commercial antibodies against H5 HA (Acris Antibodies).

FIG. 3 shows the results of rHA-A/H5N1/Qinghai testing for the presence of oligomers. The test showed, that there are oligomeric forms of the protein in the preparation, and it is according to specification.

Hemagglutination Activity of rHA-A/H5N1/Qinghai rHA-A/H5N1/Qinghai protein, for which oligomeric forms were found using ELISA, was subjected to an additional analysis for the presence of functional oligomers (using hemagglutination test). In this test, the ability of the viral protein to cause erythrocyte agglutination by binding with their surface receptors is used. Evaluation of erythrocyte agglutination ability is commonly used in the analyses of vaccine antigens quality.

Preparation of fresh erythrocytes collected from the blood of SPF chickens, obtained from sterile culture from Department of Poultry Diseases, National Veterinary Research Institute in Pulawy (Poland), was used in HA test. LPAIV A/turk/It/80 (H5N2) (x-OvO) certified by Istituto Zooprofilattico Sperimentale delle Venezie (IZSVe) in Legnaro (Italy) was used as a positive control. Erythrocytes control without viral antigen (internal control for the environment) was also included in the test. The test was performed using 96 well conical bottom (V) plates (CellStar/Greiner bio-one).

In order to evaluate hemagglutination activity of rHA-A/H5N1/Qinghai, 50 μl PBS-Dulbecco (Sigma-Aldrich), following by suitable amount of antigen and buffer (up to 100 μL of the final volume) were added into each well of the plate. Samples containing rHA in amounts from 0.1 μg to 10 μg were thus prepared. Positive control was performed by serial dilutions of the suspension containing 4 hemagglutination units (HAU) H5N2 LPAIV in PBS-Dulbecco. Buffer only (PBS-Dulbecco) was added into the wells intended for erythrocytes control. Next, 50 μL of 1% erythrocyte suspension in PBS-Dulbecco was added into each well and the contents of the wells were gently mixed by pipetting. The plate was incubated for 45 min at room temperature and then the results were read. According to the principle of the test, hemagglutination effect was evaluated visually by comparison of the samples with erythrocytes control. In contrary to the control erythrocytes, agglutinated erythrocytes do not sediment but form unitary suspension.

Hemagglutination test performed using chicken erythrocytes showed, that rHA-A/H5N1/Qinghai has the ability to evoke hemagglutination, similarly to H5N2 LPAIV. Hemagglutination effect was observed within whole tested range of antigen concentrations, including samples containing 0.1 μg of the protein. The results indicate, that rHA-A/H5N1/Qinghai forms functional oligomers, which is the desired feature of vaccine HA. It also applies to HA proteins used as immunogens in the mAbs manufacturing procedure with the use of hybridoma method.

Summary

The results of the tests indicate, that rHA-A/H5N1/Qinghai protein shares native antigen characteristics: it maintains conformational epitopes recognized by anti-H5 HA antibodies, including HI antibodies, forms oligomeric structures and has the ability to bind to cell surface receptors and agglutinate erythrocytes. This leads to the conclusion, that rHA-A/H5N1/Qinghai protein is valuable immunogen, thus rationalizing its use in the procedure of manufacturing anti-H5 HA mAbs by hybridoma method.

Example 3

Specificity and Isotype Assays

Besides using valuable immunogen, another condition for generating mAbs of high diagnostic value is the use of adequate procedure for selection of serotype-specific antibodies. For this purpose, tests using HA proteins maintaining conformation of native antigen were developed. Two antigens were chosen for an initial selection of hybridomas producing anti-H5 HA antibodies. One of them was rHA-A/H5N1/Qinghai protein for animal vaccination. Properties of rHA-A/H5N1/Qinghai, indicting its usefulness as an immunogen, but also as an antigen for the mAbs selection, were described in detail in Example 2. Another antigen was 17-530 aa (ΔRRRKKR (SEQ ID NO: 13), 6×His (SEQ ID NO: 14)) protein with the HA sequence of A/swan/Poland/305-135V08/2006 (H5N1) strain of AIV, produced in baculovirus expression system (OET). Similarly to rHA-A/H5N1/Qinghai, recombinant HA protein from baculovirus expression system, described hereinafter as rHA-A/H5N1/Poland, was glycosylated protein.

Amino acid sequence of rHA-A/H5N1/Poland was very similar to the immunogen sequence. Using BLAST software, it was shown, that homology between hemagglutinins of A/swan/Poland/305-135V08/2006 (H5N1) and A/Bar-headed Goose/Qinghai/12/05 (H5N1) strains, measured as a percentage of amino acid sequence identity, is 99%, wherein one conservative change of amino acids is found in the signal sequence, and the other three changes are semiconservative and are found in HA1 and HA2 subunit of the protein. Usefulness of rHA-A/H5N1/Poland for verification of specificity of antibodies against H5 HA was evaluated by performing protein antigenicity and oligomerization analysis and protein's ability for hemagglutination.

Figure 4:
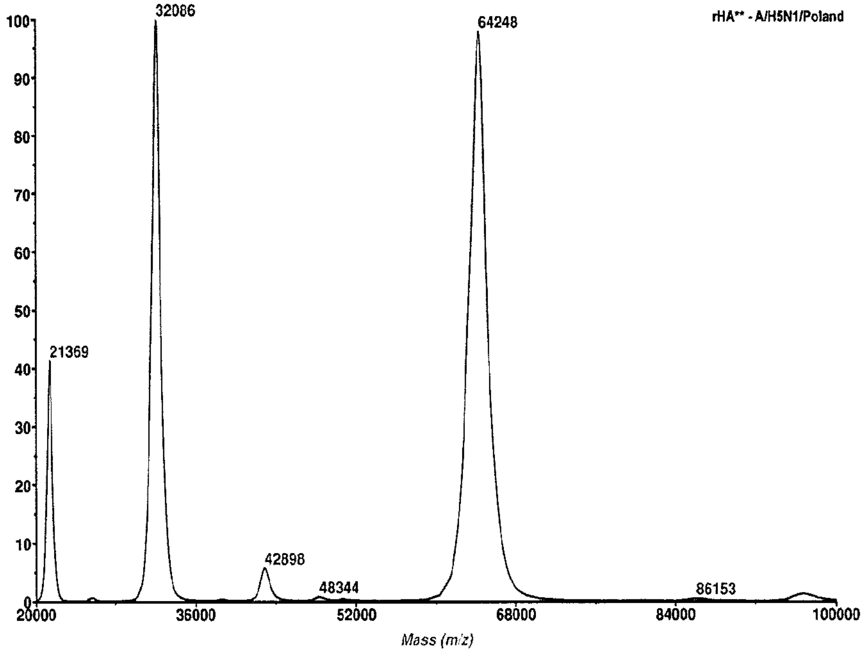
FIG. 4 shows mass spectrum of HA-A/H5N1/Poland from (**) baculovirus expression system. The protein (17-530 aa, ΔRRRKKR (SEQ ID NO: 13), 6×His (SEQ ID NO: 14)) was produced based on the sequence of HA of A/swan/Poland/305-135V08/2006 (H5N1) strain of AIV (OET, series 2). Mass spectrum was obtained using MALDI TOF/TOF (4800 Plus, AB SCIEX) mass spectrometer.

Properties of rHA-A/H5N1/Poland rHA-A/H5N1/Poland (OET) was analyzed using MALDI TOF/TOF (4800 Plus, AB SCIEX) mass spectrometer described in Example 2 for rHA-A/H5N1/Qinghai. Determined molecular weight of the antigen (OET, series 2-8) was 64 kDa (FIG. 4) and, due to the glycosylation, was ~6 kDa higher than the mass calculated based on the amino acid composition in GPMAW 8.2 software (Lighthouse). The difference between experimentally and theoretically determined rHA-A/H5N1/Poland molecular weight was lower than in case of rHA-A/H5N1/Qinghai (~6 kDA vs ~18 kDa), which indicates the differences in the level of glycosylation of rHA produced in baculovirus and mammalian expression system.

Figure 5:
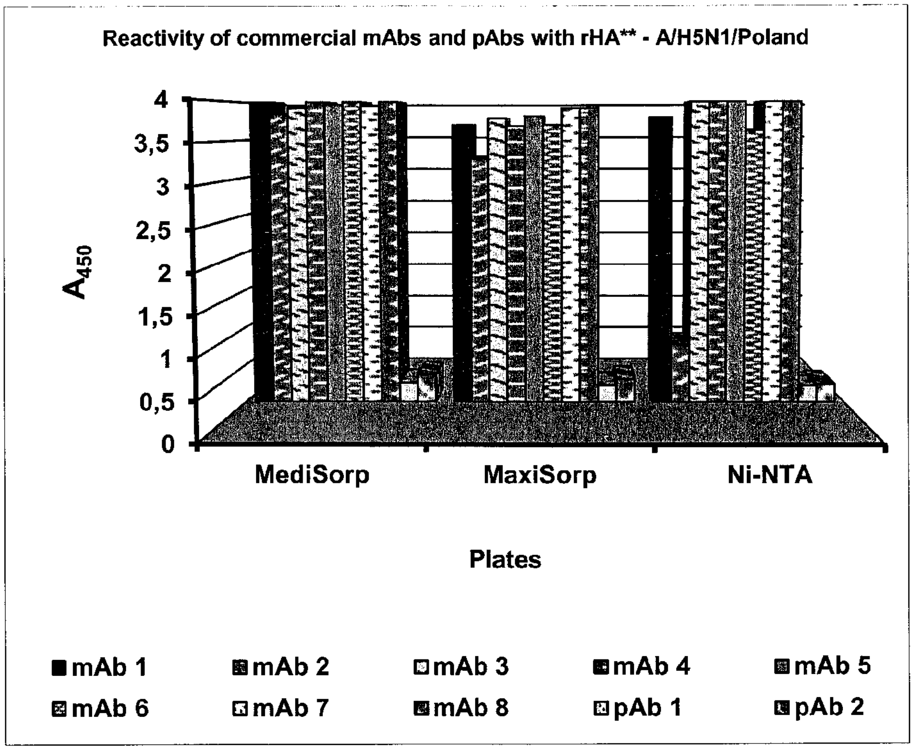
FIG. 5 shows the results of antigenicity analysis of rHA-A/H5N1/Poland from (**) baculovirus expression system. The protein (17-530 aa, ΔRRRKKR (SEQ ID NO: 13), 6×His (SEQ ID NO: 14)) was produced based on the sequence of HA of A/swan/Poland/305-135V08/2006 (H5N1) strain of AIV (OET, series 2). The tests were carried out using ELISA on MediSorp, MaxiSorp (NUNC) and Ni-NTA (Qiagen) plates. Commercially available mAb against H5 HA (USBiological, ABR/Thermo Scientific, Acris Antibodies) and pAbs against HA1 (pAb 1) and HA2 (pAb 2) subunit of the antigen (ITC) were used in the tests.

The panel of commercially available mAbs and pAbs against H5 HA (List A), described in Example 2, was used in rHA-A/H5N1/Poland antigenicity studies. Analysis was performed by ELISA method using polystyrene plates of various hydrophilicity (NUNC) and Ni-NTA plates (Qiagen), in the same way as antigenicity studies for rHA-A/H5N1/Qinghai (Example 2). FIG. 5 shows the results of rHA-A/H5N1/Poland antigenicity studies (OET, series 2) conducted using MediSorp, MaxiSorp and Ni-NTA plates. Reactivity of mAb 2, pAb 1 and pAb 2 with rHA-A/H5N1/Poland bound to Ni-NTA plate was significantly lower than with rHA-A/H5N1/Qinghai (FIG. 2), which was probably the result of the difference in binding and/or presentation of antigens on the plate. Taking into account the reactivity of mAb and pAb with HA antigen derived from baculovirus expression system and bound to different type of plates (FIG. 5) it can be concluded, that the protein contains well preserved conformational epitopes of HA1 subunit, including epitopes recognized by HI-type antibodies. Antibody reactivity studies were performed for each of the used antigen series. Each time the results showed normal conformation of HA1 subunit of rHA-A/H5N1/Poland antigen.

The oligomerization status for rHA-A/H5N1/Poland (OET, series: 5, 8) was examined using a sandwich ELISA with non-labeled and HRP-labelled commercial antibodies against H5 HA, described on the List A as mAb 8 (Acris Antibodies, Cat. No. AM00941PU-N, AM00941HR-Cus). Recombinant HA was tested as a series of 2-fold dilution in the range of 10 μg/mL-0.009 ng/mL. Test method is described in Example 2. The results shown in FIG. 3 indicate, that rHA-A/H5N1/Poland protein contains significantly less oligomeric forms than rHA-A/H5N1/Qinghai antigen. Moreover, the differences were observed in the oligomerization state of the protein derived from different series from baculovirus expression system.

rHA-A/H5N1/Poland (OET, series 5) was subjected to various tests in order to evaluate protein's ability for erythrocyte agglutination. HA protein produced in baculovirus expression system was tested simultaneously with rHA from mammalian expression system (rHA-A/H5N1/Qinghai). Hemagglutination test method is described in Example 2. The test was performed using chicken erythrocytes and showed, that rHA-A/H5N1/Poland has the ability to hemagglutinate. Full hemagglutination effect was observed in the samples containing from 10 μg to 2.5 μg of the antigen. Partial hemagglutination was observed in the samples containing 1 μg of the antigen. For erythrocytes agglutination significantly higher concentration of rHA-A/H5N1/Poland than rHA-A/H5N1/Qinghai was needed (Example 2), which is in line with the results of ELISA for testing the oligomerization state of HA proteins (FIG. 3). The results of hemagglutination test indicate, that rHA-A/H5N1/Poland is present partially in the form of oligomers responsible for erythrocytes agglutination. However, the content of functional oligomers in rHA-A/H5N1/Poland antigen is significantly lower than in rHA-A/H5N1/Qinghai antigen (Example 2).

In summary, rHA-A/H5N1/Poland from baculovirus expression system preserves conformational epitopes recognized by anti-H5 HA antibodies, including HI antibodies. In comparison to rHA-A/H5N1/Qinghai, this protein is characterized by the lower level of glycosylation and low degree of oligomerization, which is an important feature of viral HA. Normal conformation of HA1 subunit of the antigen derived from baculovirus expression system rationalizes its use for testing for the specificity of generated anti-H5 HA antibodies simultaneously with the mammalian expression system-derived antigen. Different way of presenting epitopes of HA1 subunit in rHA-A/H5N1/Poland than in rHA-A/H5N1/Qinghai was found preferable for the effectiveness of selection of anti-HA mAbs.

ELISA for Determining Specificity of the Obtained mAbs

ELISA was used to determine the specificity of the produced antibodies. For this purpose tests were developed using previously characterized proteins: rHA-A/H5N1/Qinghai and rHA-A/H5N1/Poland. Test optimization was performed mainly by the selection of plates for binding particular antigens. The primary criterion for test plate selection was the availability of important conformational epitopes in the plate-bound protein, assessed using commercially available anti-H5 HA mAbs and pAbs (List A). At the stage of test optimization, all types of protein immobilization surfaces offered by NUNC (PolySorp, MediSorp, MaxiSorp, MultiSorp), as well as Ni-NTA plates (Qiagen) were used. Antigens are adsorbed on the polystyrene plates by different fragments of the protein, mainly in a random manner, whereas antigen immobilization on Ni-NTA plates is directional. Tests for optimization of antibody specificity assays were performed in the same conditions as used in the studies of rHA-A/H5N1/Qinghai (Example 2) and rHA-A/H5N1/Poland (Example 3) antigenicity.

With the use of polystyrene plates of different hydrophilicity it was shown, that using MediSorp and MaxiSorp plates for antigen binding, particularly rHA-A/H5N1/Poland, provides better sensitivity of antibody assays than using other types of polystyrene plates (data not shown). It was also shown, that reactivity of commercial antibodies with rHA-A/H5N1/Qinghai is higher after binding to Ni-NTA plate (FIG. 2), while with rHA-A/H5N1/Poland after binding to MediSorp plate (FIG. 5). The differences in antigen presentations, which depend on the plate being used, were found using mainly pAb 1 and pAb 2 in case of rHA from mammalian expression system and mAb 2 in case of rHA from baculovirus expression system. Anti-mouse IgG, γ-chain specific antibodies were used in ELISA for the determination of antibody specificities. The use of highly specific secondary antibodies in the developed tests limited the selection of generated anti-H5 HA antibodies to H5-specific antibodies of IgG-class, which, in diagnostic tests, are the most useful among antibodies of various isotypes, due to their usually high affinity for the antigen.

Eventually, specificity of antibodies was determined by ELISA using Ni-NTA plates (Qiagen) for coating with rHA H5 derived from mammalian expression system and MediSorp plates (NUNC) for coating with rHA H5 derived from baculovirus expression system. rHA-A/H5N1/Qinghai protein diluted in 1% BSA/PBS to 1 μg/mL was applied on Ni-NTA plates. MediSorp plates were coated with rHA-A/H5N1/Poland in PBS in 6.2 μg/mL or 5 μg/mL concentration. In order to control the level of unspecific binding of antibodies, some wells were filled in with 1% BSA/PBS (Ni-NTA plates) or PBS (MediSorp plates) and incubated overnight at 2-8° C., in parallel to the antigen-containing wells. Because Ni-NTA strips from Qiagen are pre-blocked, testing was carried out without blocking stage. Non-specific binding sites on the MediSorp plates were blocked with the use of 10% FBS/PBS. Supernatant from non-cloned hybridomas was analysed in 1:20 dilution (Ni-NTA plates coated with rHA-A/H5N1/Qinghai) or 1:10 (MediSorp plates coated with rHA-A/H5N1/Poland). After cloning of hybridomas, culture supernatants were analysed without dilution. Commercial anti-H5 HA antibodies diluted to 0.01 μg/mL in PBS, were used as positive controls (mAb 8, List A). RPMI buffer was the control for non-specific binding of secondary antibodies (BLK sample). Plates with the tested and control samples were incubated overnight at 2-8° C. HRP-labelled anti-mouse IgG antibodies (γ-chain specific, Sigma-Aldrich) were used for the detection of antigen-bound mAbs. Secondary antibodies were diluted 1:1000 using 2% BSA/PBS and were incubated on the plates for 1 h at 37° C. TMB (Sigma-Aldrich) was used as a substrate for HRP. Reaction was stopped using 1.25 M (Ni-NTA strips) or 0.5 M (MediSorp plates) solution of $H_2SO_4$. Absorption of samples was read at λ=450 nm.

Isotyping of the Obtained Antibodies

Classes and subclasses of the obtained mAbs were determined using "Mouse Monoclonal Antibody Isotyping Reagents"—ISO-2 isotyping kit (Sigma-Aldrich). MaxiSorp plates (NUNC) were coated with antibodies against mouse antibodies of various classes and subclasses (IgG1, IgG2a, IgG2b, IgG3, IgA, IgM) in 1:1000 dilution in PBS, wherein the incubation was carried out for 1 h at 37° C. or overnight at 2-8° C. Non-diluted or diluted samples from hybridoma culture supernatants were incubated in the coated plates (1 h, 37° C.). Control sample was PBS or RPMI (BLK sample). Whole molecule-specific (1:1000) or Fab fragment-specific (1:50 000), diluted in 1% BSA/PBST, HRP-labelled antibodies against mouse IgG antibodies (Sigma-Aldrich), were used for the detection of antibodies bound by the isotype-specific antibodies. Plates with the diluted antibodies were incubated for 30 min at room temperature. TMB (Sigma-Aldrich) was used as a substrate for HRP. Reaction was inhibited using 0.5 M solution of $H_2SO_4$. Absorption of samples was read at λ=450 nm. Described procedure is a modified version on manufacturer's instruction for ISO-2 kit. Implemented changes were related to the conditions of sample incubation on the plate, as well as to the antibodies and substrate used to develop the plates.

Example 4 Analysis of Serotype Specificity

Development of immunological tests, which may be used to detect infection with IVs of H5 serotype (including H5N1 AIVs) in animals and humans, requires the use of mAbs having broad range of specificities against H5 HA. Therefore, antibodies specific against HA of amino acid sequence identical or very similar to the sequence of immunogen, were further selected for serotype specificity. For this purpose, tests were developed using different forms of H5 HA antigens (positive selection) and HA of serotypes other than H5 (negative selection). For positive selection, recombinant H5 HA proteins based on the ectodomain (rHA) or HA1 subunit (rHA1) of hemagglutinin, having varied homology to the immunogen and AIVs of H5 serotype (H5N1, H5N2, H5N3 and H5N9) were used. Negative selection was performed using AIVs of fifteen serotypes other than H5 (H1-H4 and H6-H16).

Recombinant H5 HA Proteins

Antigens used in the serotype specificity studies, described as ectodomain-based HA proteins, corresponded to H5 HA from which signal sequence, transmembrane domain and cytoplasmic domain were removed. Antigen fragments corresponding to HA1 subunit, which is characterized by the greater sequence variability than HA2 subunit and contains serotype-specific epitopes, were also present in the panel of HA proteins. The use of antigens described as HA1 subunit-based HA proteins, was increasing probability of finding clones specific against HA of H5 serotype among selected antibodies. Recombinant HA proteins based on the ectodomain (rHA) and HA1 subunit (rHA1) of the antigen, were produced in mammalian expression system (ITC). For the analysis of serotype specificity of produced antibodies, proteins were selected based on the variation of the homology to the immunogen (rHA-A/H5N1/Qinghai). Studies on the specificity of anti-H5 HA antibodies with varied homology were carried out simultaneously to studies on the specificity towards antigens having amino acid sequence identical or significantly similar to the sequence of the immunogen, which were generated using mammalian (rHA-A/H5N1/Qinghai) and baculovirus (rHA-A/H5N1/Poland) expression system. In total, in the analysis of serotype specificity, recombinant proteins with HA sequences from nine IVs of H5 serotype, including H5N1 (8 strains) and H5N2 (1 strain) were used. Information regarding antigens used in the analysis of specificity of generated antibodies, including serotype specificity, is shown below, on the List.

List B Recombinant hemagglutinin proteins used in the analysis of serotype specificity of generated antibodies.

| Antigen | Influenza virus strain of H5 serotype Hemagglutinin Genbank Accession No. (EpiFluDatabase Accession No.) | HA fragment expression system | Origin |
|---|---|---|---|
| Hemagglutinin ectodomain-based recombinant proteins (rHA) | | | |
| rHA - A/H5N1/Qinghai | A/Bar-headed Goose/Qinghai/12/05 (H5N1) ABE68927 | 17-530 aa, ΔRRRKKR (SEQ ID NO: 13), 6x His (SEQ ID NO: 14) mammalian | ITC |
| rHA - A/H5N1/India | A/chicken/India/NIV33487/2006(H5N1) ABQ45850 | 17-530 aa, ΔRRRKKR (SEQ ID NO: 13), 6x His (SEQ ID NO: 14) mammalian | ITC |
| rHA - A/H5N1/Vietnam | A/Vietnam/1203/2004(H5N1) AAW80717 | 18-530 aa, ΔRRRKKR (SEQ ID NO: 13), 6x His (SEQ ID NO: 14) mammalian | ITC |
| rHA - A/H5N1/Guiyang | A/goose/Guiyang/337/2006(H5N1) ABJ96698 | 17-530 aa, ΔRRRKKR (SEQ ID NO: 13), 6x His (SEQ ID NO: 14) mammalian | ITC |
| rHA - A/H5N1/Ck/Vietnam | A/chicken/Vietnam/NCVD-016/08(H5N1) ACO07033 | 18-534 aa, 6x His (SEQ ID NO: 14) mammalian | ITC |
| rHA - A/H5N2/California | A/American green-winged teal/ California/HKWF609/2007(H5N2) ACF47563 | 19-506 aa, 6x His mammalian | ITC |
| rHA - A/H5N1/Poland | A/swan/Poland/305-135V08/2006(H5N1) (EPI156789) | 17-530 aa, ΔRRRKKR (SEQ ID NO: 13), 6x His (SEQ ID NO: 14) baculovirus | OET |
| Hemagglutinin HA1 subunit-based recombinant proteins (rHA1) | | | |
| rHA1 - A/H5N1/Vietnam | A/Vietnam/1203/2004(H5N1) AAW80717 | 1-345 aa, 6x His (SEQ ID NO: 14) mammalian | ITC |
| rHA1 - A/H5N1/HK/156 | A/Hong Kong/156/97(H5N1) AAC32088 | 18-346 aa, 6x His (SEQ ID NO: 14) mammalian | ITC |
| rHA1 - A/H5N1/HK/483 | A/Hong Kong/483/97(H5N1) AAC32099 | 17-346 aa, 6x His(SEQ ID NO: 14) mammalian | ITC |

ITC—Immune Technology Corporation (USA)
OET—Oxford Expression Technologies (Great Britain)

Ectodomain-based HA proteins (rHA) from mammalian expression system were the fragments of antigen containing HA1 subunit and part of the HA2 subunit, expressed without signal sequence (17-530 aa, 18-530 aa, 18-534 aa, 19-506 aa). Cleavage regions (ΔRRRKKR (SEQ ID NO: 13)) were removed in four out of six HA antigens and, according to the specification, those proteins were mainly in the form of trimers/oligomers. HA1 subunit-based recombinant HA proteins (rHA1) were expressed in mammalian cells with (1-345 aa) or without (18-346 aa, 17-346 aa) signal sequence. Conformation of rHA1 proteins was not specified. All recombinant HA proteins contained 6×His (SEQ ID NO: 14) tag. Antigens were of at least 95% purity. On the electrophoregrams of purified antigens, rHA and rHA1 from mammalian expression system were present as single bands having molecular weight of −75 kDa and −50 kDa, respectively.

Usefulness of rHA and rHA1 antigens, as shown on List B, for testing serotype specificity of the obtained antibodies was evaluated by performing tests for antigenicity and oligomerization state. Method for testing antigenicity of rHA-A/H5N1/Qinghai and rHA-A/H5N1/Poland is shown in Examples 2 and 3, respectively. As in the case of rHA-A/H5N1/Qinghai and rHA-A/H5N1/Poland, tests for the antigenicity of rHA and rHA1 were performed using commercially available anti-H5 HA antibodies. mAbs recognising native HA, mAbs showing properties of serotype-specific antibodies and mAbs active in HI test were incorporated into the panel of antibodies. Commercial mAbs and pAbs used for the characterization of HA proteins are shown in the List A and described in detail in Example 2.

Antigenicity tests for rHA proteins having sequences of A/H5N1/India, A/H5N1/Vietnam, A/H5N1/Guiyang, A/H5N1/Ck/Vietnam, A/H5N2/California strains, as well as rHA1 proteins having sequences of A/H5N1/Vietnam, A/H5N1/HK/156 and A/H5N1/HK/483 strains were performed by ELISA using Ni-NTA plates (Qiagen). HA proteins diluted in 1% BSA/PBS to 1 μg/mL concentration were applied on the plates. In order to control the level of unspecific binding of antibodies, some wells were filled in with 1% BSA/PBS and incubated overnight at 2-8° C., in parallel to the antigen-containing wells. In the antigenicity tests for seven out of eight recombinant H5 HA proteins mentioned above, all anti-H5 HA mAbs and pAbs from List A were used. Antibodies diluted to 1 μg/mL in 2% BSA/PBS, were incubated in coated plates overnight at 2-8° C. To develop the plates, whole molecule-specific HRP-labelled pAbs against mouse IgG (Sigma-Aldrich) or HRP-labelled monoclonal antibodies against rabbit IgG, γ-chain specific (Sigma-Aldrich) were used. The secondary antibodies were diluted 1:1000 in 1% BSA/PBST and incubated in the plates for 45 min at room temperature. rHA1-A/H5N1/HK/156 antigenicity tests were performed using antibodies described as mAb 8, diluted to 0.1 μg/mL in 2% BSA/PBS. Antigen-bound mAbs were detected using whole molecule-specific, HRP-labelled, anti-mouse IgG pAbs (Sigma-Aldrich), diluted 1:1000 in 2% BSA/PBS and incubated with the plate for 60 min at 37° C. TMB (Sigma-Aldrich) was used as a substrate for horseradish peroxidase. Reaction was inhibited using 1.25 M solution of $H_2SO_4$. Absorption of samples was read at λ=450 nm. ELISA was not optimized for particular antigens and antibodies.

Figure 6:
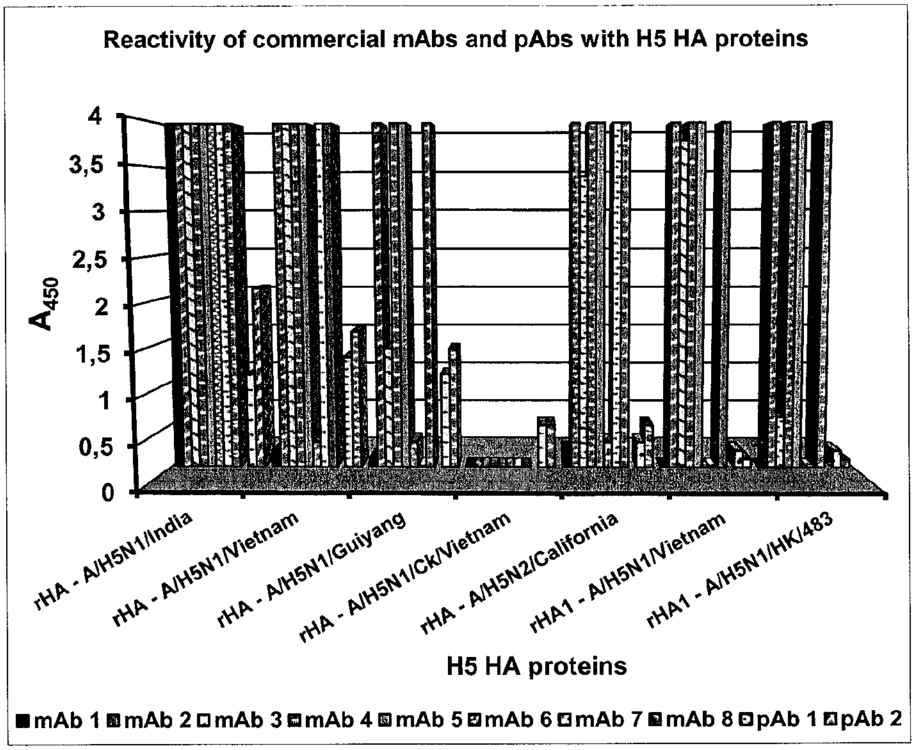
FIG. 6 shows the results of antigenicity analysis for recombinant proteins with HA sequences of various H5 serotype IV strains. HA H5 proteins, based on ectodomain (rHA) and HA1 subunit (rHA) of the antigen, were prepared in mammalian expression system (ITC). The tests were carried out using ELISA on Ni-NTA (Qiagen) plates. Commercially available mAb against H5 HA (USBiological, ABR/Thermo Scientific, Acris Antibodies) and pAbs against HA1 (pAb 1) and HA2 (pAb 2) subunit of the antigen (ITC) were used in the tests.

FIG. 6 shows the results of reactivity studies of rHA proteins based on the sequences of A/H5N1/India, A/H5N1/Vietnam, A/H5N1/Guiyang, A/H5N1/Ck/Vietnam, A/H5N2/California strains, as well as rHA1-A/H5N1/Vietnam and rHA1-A/H5N1/HK/483 proteins. rHA and rHA1 proteins are shown in order of decreasing homology to the immunogen (rHA-A/H5N1/Qinghai). Amino acid identity in HA1 subunit sequence of rHA antigens was from 99% to 88%, and rHA1 antigens 95% and 94%. As shown in FIG. 6, six antigens out of seven recombinant HA proteins formed detectable immunological complexes with monoclonal antibodies. Particular proteins were recognized by a certain number of commercial mAb clones with similar or different affinity. rHA-A/H5N1/India protein was recognized by all monoclonal antibodies (8/8) with high affinity, similarly to rHA-A/H5N1/Qinghai, FIG. 2. rHA-A/H5N1/Vietnam and rHA-A/H5N2/California proteins were recognized with high affinity by six, rHA1-A/H5N1/Vietnam protein by five, and rHA-A/H5N1/Guiyang and rHA1-A/H5N1/HK/483 proteins by four out of eight commercial monoclonal antibodies used. Antibodies referred to as mAb3 also bound rHA-A/H5N1/Guiyang and rHA1-A/H5N1/HK/483 proteins, although with lowered affinity. Above described H5 HA ectodomain-based antigens (rHA) were detected by polyclonal antibodies. Observed variation of antigenicity profiles of HA proteins could be associated with HA1 subunit variability and different range of specificities of used commercial monoclonal antibodies. Additionally, different presentation of rHA and rHA1 antigens and lower sensitivity of the test, in which rHA1 rather than rHA was used, could affect results obtained for the proteins based on ectodomain and HA1 subunit.

Studies of rHA1-A/H5N1/HK/156 antigenicity with the use of mAb 8 having a broad range of specificities against H5 HA (FIG. 6) showed, that the protein is recognized by those antibodies with high affinity (data not shown). Studies of rHA-A/H5N1/Ck/Vietnam antigenicity, on the other hand, with the use of all mAbs and pAbs against H5 HA shown in List A showed, that the protein is recognized only by polyclonal antibodies pAb 1 and pAb 2 (FIG. 6). None of the eight monoclonal antibodies was binding to this antigen. Taking into account profile of specificities of monoclonal antibodies used in the studies, one may concluded, that conformation of rHA-A/H5N1/Ck/Vietnam, as in the opposite to the other recombinant HA proteins, is not correct. The results of antigenicity analysis for rHA-A/H5N1/Qinghai and rHA-A/H5N1/Poland, indicating that those proteins retain features of native HA conformation, are described in Examples 3 and 3, respectively.

The results of antigenicity analysis for recombinant HA proteins, showed in FIGS. 2, 5 and 6, indicate, that nine out of ten recombinant HA proteins (List B) of varied homology to the immunogen, including hemagglutinin ectodomain-based (6 proteins) and HA1 subunit-based (3 proteins), has features of viral HA structure. Studies rationalize the use of all tested HA proteins in the selection procedure for generated antibodies. The use of HA1 subunit-based proteins allowed for the selection of mAbs against conformational epitopes of HA1 subunit, whereas the use of rHA-A/H5N1/Ck/Vietnam allowed for differentiation of antibodies recognizing conformational and non-conformational H5 HA epitopes.

Tests for the presence of oligomeric forms in rHA and rHA1 antigen were performed by sandwich ELISA, identically as in the oligomerization studies for rHA-A/H5N1/Qinghai and rHA-A/H5N1/Poland. Test conditions are described in Example 2. The results for ten recombinant H4 HA proteins from List B are shown in FIG. 3. The degree of rHA-A/H5N1/India and rHA-A/H5N1/Vietnam oligomerization was comparable to the one observed for rHA-A/H5N1/Qinghai. Slightly lower degree of oligomerization was shown for rHA-A/H5N2/California protein. rHA-A/H5N1/Guiyang antigen contained significantly less oligomeric forms than other rHA proteins from mammalian expression system, but more than both rHA-A/H5N1/Poland series from baculovirus expression system. No oligomeric forms were found in non-conformational rHA-A/H5N1/Ck/Vietnam antigen, and this founding confirms the results of antigenicity analysis of this protein with antibodies referred to as mAb 8 (FIG. 6), which found use in the test for oligomerization degree analysis. ELISA for the analysis of the degree of oligomerization of HA proteins confirmed, that rHA1 antigens are present on monomeric forms. Little degree of oligomerization was found only for rHA1-A/H5N1/Vietnam protein, which contained signal sequence, as in the opposite to rHA1-A/H5N1/HK/156 and rHA1-A/H5N1/HK/483 proteins.

H1-H16 Serotype Influenza Viruses

AIVs were used in the analysis of serotype specificity of generated antibodies. The viruses (x-OvO) had IZSVe certificates. The list of used AIVs is given below, in the List.

List C Avian influenza viruses used in the analysis of serotype specificity of generated antibodies.

| Hemagglutinin | Avian influenza virus | | |
|---|---|---|---|
| serotype | serotype | Strain | Origin |
| H1 | H1N1 | A/duck/It/1447/05(H1N1) | x-OvO |
| H2 | H2N3 | A/duck/Germ/1215/73(H2N3) | x-OvO |
| H3 | H3N8 | A/pass/It/6000/V00(H3N8) | x-OvO |
| | | A/psitt/It/2873/00(H3N8) | x-OvO |
| H4 | H4N8 | A/cockatoo/Eng/72(H4N8) | x-OvO |
| H5 | H5N1 | A/mallard/It/3401/05(H5N1) | x-OvO |
| | H5N2 | A/turk/It/80(H5N2) | x-OvO |
| | H5N3 | A/duck/It/775/04(H5N3) | x-OvO |
| | H5N9 | A/ck/It/22A/98(H5N9) | x-OvO |
| H6 | H6N2 | A/turkey/Canada/65 (H6N2) | x-OvO |
| H7 | H7N1 | A/ck/It/1067/V99(H7N1) | x-OvO |
| | H7N3 | A/ty/It/9289/V02(H7N3) | x-OvO |
| | H7N4 | A/mallard/It/4810-79/04(H7N4) | x-OvO |
| | H7N7 | A/macaw/626/80(H7N7) | x-OvO |
| H8 | H8N4 | A/turk/Ont/6118/68(H8N4) | x-OvO |
| H9 | H9N2 | A/ty/Wis/66(H9N2) | x-OvO |
| | H9N7 | A/turk/Scotland/1/70(H9N7) | x-OvO |
| H10 | H10N1 | A/ostrich/SA/01(H10N1) | x-OvO |
| H11 | H11N6 | A/duck/Eng/56(H11N6) | x-OvO |
| | H11N9 | A/duck/Memphis/546/174(H11N9) | x-OvO |
| H12 | H12N5 | A/duck/Alberta/60/76(H12N5) | x-OvO |
| H13 | H13N6 | A/gull/Maryland/704/77(H13N6) | x-OvO |
| H14 | H14N5 | A/mallard/Gurjev/263/82(H14N5) | x-OvO |

-continued

List C Avian influenza viruses used in the analysis of serotype specificity of generated antibodies.

| Hemagglutinin serotype | Avian influenza virus serotype | Strain | Origin |
|---|---|---|---|
| H15 | H15N9 | A/shearwater/2576/79(H15N9) | x-OvO |
| H16 | H16N3 | A/gull/Denmark/68110/02(H16N3) | x-OvO |

x-OvO Limited (Great Britain), Istituto Zooprofilattico Sperimentale delle Venezie (IZSVe, Italy)

Twenty-five AIV strains were used in the analysis of serotype specificity of the antibodies, including four H5 serotype AIVs, and the rest of H1, H2, H3, H4, H6, H7, H8, H9, H10, H11, H12, H13, H14, H15 and H16 serotype.

Homology of H5 HA Antigens

In the analysis of serotype specificity of generated antibodies, hemagglutinins or their fragments having sequences of thirteen IV strains of H5 serotype (List B and C) were used. This number includes H5N3 (1 strain), H5N9 (1 strain), H5N2 (2 strains) and, above all, H5N1 viruses (9 strains), classified into six different clades, mentioned in the list below.

List D Classification of H5N1 influenza viruses, from which sequences of H5 HA antigen were derived.

| Influenza virus strain of H5 serotype | Hemagglutinin Genbank Accession No. (EpiFluDatabase Accession No.) | Clade IV H5N1 |
|---|---|---|
| A/Hong Kong/156/97(H5N1) | AAC32088 | 0 |
| A/Hong Kong/483/97(H5N1) | AAC32099 | 0 |

-continued

List D Classification of H5N1 influenza viruses, from which sequences of H5 HA antigen were derived.

| Influenza virus strain of H5 serotype | Hemagglutinin Genbank Accession No. (EpiFluDatabase Accession No.) | Clade IV H5N1 |
|---|---|---|
| A/Vietnam/1203/2004(H5N1) | AAW80717 | 1 |
| A/Bar-headed Goose/Qinghai/12/05(H5N1) | ABE68927 | 2.2 |
| A/chicken/India/NIV33487/2006(H5N1) | ABQ45850 | 2.2 |
| A/swan/Poland/305-135V08/2006(H5N1) | (EPI156789) | 2.2 |
| A/goose/Guiyang/337/2006(H5N1) | ABJ96698 | 4 |
| A/chicken/Vietnam/NCVD-016/08(H5N1) | ACO07033 | 7 |
| A/mallard/Italy/3401/2005(H5N1) | ABG57086.1 | EA-nonGsGD |

EA-nonGsGD—H5 serotype virus, more similar to low pathogenic viruses of Eurasian origin Homology of hemagglutinins, from which sequences of H5 HA antigens were derived, was determined against 1-567 aa (full-length protein) and 17-338 aa (HA1 subunit) fragments of the HA of A/Bar-headed Goose/Qinghai/60/05 (H5N1) strain, which is the source of immunogen sequence (rHA-A/H5N1/Qinghai). Sequences were analysed using BLAST software. Relative homologies of full-length hemagglutinins are shown in the List E, while HA1 subunits of the proteins are shown in the List F. Hemagglutinins of different IV strains are shown in decreasing Max Score order.

List E Homology of full-length hemagglutinins, from which sequences of H5 HA antigens were derived, against hemagglutinin of A/H5N1/Qinghai strain, determined using BLAST software. Sequences producing significant alignments:

| Description | Max score | Total score | Query cover | E value | Ident | Accession[x] |
|---|---|---|---|---|---|---|
| hemagglutinin [Influenza A virus (A/Bar-headed Goose/Qinghai/60/05(H5N1))] | 1186 | 1186 | 100% | 0.0 | 100% | ABE68927.1 |
| hemagglutinin [Influenza A virus (A/chicken/India/NIV33487/06(H5N1))] | 1181 | 1181 | 99% | 0.0 | 99% | ABQ45850.1 |
| hemagglutinin [Influenza A virus (A/swan/Poland/305-135V08/2006(H5N1))] | 1177 | 1177 | 99% | 0.0 | 99% | (EPI156789) |
| hemagglutinin HA [Influenza A virus (A/Viet Nam/1203/2004(H5N1))] | 1150 | 1150 | 99% | 0.0 | 97% | AAW80717.1 |
| hemagglutinin subtype H5 [Influenza A virus (A/Hong Kong/156/97(H5N1))] | 1142 | 1142 | 99% | 0.0 | 96% | AAC32088.1 |
| hemagglutinin subtype H5 [Influenza A virus (A/Hong Kong/483/1997(H5N1))] | 1135 | 1135 | 99% | 0.0 | 95% | AAC32099.1 |
| hemagglutinin [Influenza A virus (A/duck/Italy/775/2004(H5N3))] | 1112 | 1112 | 99% | 0.0 | 93% | ABS89310.1 |
| hemagglutinin [Influenza A virus (A/goose/Guiyang/337/2006(H5N1))] | 1100 | 1100 | 98% | 0.0 | 94% | ABJ96698.1 |
| hemagglutinin [Influenza A virus (A/chicken/Italy/22A/1998(H5N9))] | 1089 | 1089 | 99% | 0.0 | 91% | ABR37720.1 |
| hemagglutinin [Influenza A virus (A/American green-winged teal/California/HKWF609/2007(H5N2))] | 1082 | 1082 | 99% | 0.0 | 89% | ACF47563.1 |
| hemagglutinin [Influenza A virus (A/turkey/Italy/1980(H5N2))] | 1067 | 1067 | 98% | 0.0 | 91% | ACS93985.1 |
| hemagglutinin [Influenza A virus (A/chicken/Vietnam/NCVD-016/2008(H5N1))] | 1066 | 1066 | 99% | 0.0 | 91% | ACO07033.1 |
| hemagglutinin [Influenza A virus (A/mallard/Italy/3401/2005(H5N1))] | 1058 | 1073 | 96% | 0.0 | 93% | ABG57086.1 |

[x]Genbank (EpiFluDatabase) Accession No.

List F Homology of sequences forming HA1 subunit of H5 HA antigens, against HA1 subunit of hemagglutinin from A/H5N1/Qinghai strain, determined using BLAST software. Sequences producing significant alignments:

| Description | Max score | Total score | Query cover | E value | Ident | Accession[x] |
|---|---|---|---|---|---|---|
| hemagglutinin [Influenza A virus (A/Bar-headed Goose/Qinghai/60/05(H5N1))] | 679 | 696 | 100% | 0.0 | 100% | ABE68927.1 |
| hemagglutinin [Influenza A virus (A/chicken/India/NIV33487/06(H5N1))] | 677 | 694 | 100% | 0.0 | 99% | ABQ45850.1 |
| hemagglutinin [Influenza A virus (A/swan/Poland/305-135V08/2006(H5N1))] | 677 | 693 | 100% | 0.0 | 99% | (EPI156789) |
| hemagglutinin HA [Influenza A virus (A/Viet Nam/1203/2004(H5N1))] | 654 | 685 | 100% | 0.0 | 95% | AAW80717.1 |
| hemagglutinin subtype H5 [Influenza A virus (A/Hong Kong/156/97(H5N1))] | 652 | 668 | 100% | 0.0 | 95% | AAC32088.1 |
| hemagglutinin subtype H5 [Influenza A virus (A/Hong Kong/483/1997(H5N1))] | 646 | 664 | 100% | 0.0 | 94% | AAC32099.1 |
| hemagglutinin [Influenza A virus (A/duck/Italy/775/2004(H5N3))] | 636 | 652 | 100% | 0.0 | 93% | ABS89310.1 |
| hemagglutinin [Influenza A virus (A/goose/Guiyang/337/2006(H5N1))] | 635 | 650 | 100% | 0.0 | 93% | ABJ96698.1 |
| hemagglutinin [Influenza A virus (A/mallard/Italy/3401/2005(H5N1))] | 633 | 649 | 100% | 0.0 | 93% | ABG57086.1 |
| hemagglutinin [Influenza A virus (A/chicken/Italy/22A/1998(H5N9))] | 619 | 636 | 100% | 0.0 | 90% | ABR37720.1 |
| hemagglutinin [Influenza A virus (A/American green-winged teal/California/HKWF609/2007(H5N2))] | 616 | 633 | 100% | 0.0 | 88% | ACF47563.1 |
| hemagglutinin [Influenza A virus (A/turkey/Italy/1980(H5N2))] | 615 | 631 | 100% | 0.0 | 90% | ACS93985.1 |
| hemagglutinin [Influenza A virus (A/chicken/Vietnam/NCVD-016/2008(H5N1))] | 605 | 623 | 100% | 0.0 | 89% | ACO07033.1 |

[x]Genbank (EpiFluDatabase) Accession No.

Analysis of full-length hemagglutinin homology for twelve IV strains of H5 serotype against HA from A/H5N1/Qinghai strain showed significant variation of proteins (List E), from which HA antigen sequences were derived, which were used in the analysis of serotype specificity of the generated antibodies. Because serotype-specific epitopes are localised within HA1 HA subunit, high variability of sequences forming this subunit in HA antigens, as shown in homology analysis (List F), is especially important for the effective selection of the desired diagnostic monoclonal antibodies. Antigens having HA1 subunit of very high and relatively low homology against HA1 subunit of HA of A/H5N1/Qinghai strain are included in the HA protein panel. For the proteins which are the most similar to the immunogen, i.e. rHA-A/H5N1/India and rHA-A/H5N1/Poland, homology factors for HA1 subunit: Max Score, Total Score, Identities, reached values of 677, 694 and 693, and 99%, respectively. The same factors for HA1 subunit of A/H5N9/Ck/Italy AIV, rHA-A/H5N2/California, A/H5N2/Tk/Italy AIV and rHA-A/H5N1/Ck/Vietnam antigens reached values of 619-605, 636-623 and 88-90%, respectively.

ELISA for Determining Serotype Specificity of the Obtained mAbs

Clones specific for the HA having amino acid sequence identical or very similar to the immunogen sequence, i.e. to rHA-A/H5N1/Qinghai and rHA-A/H5N1/Poland, were analysed using previously characterized rHA and rHA1 proteins of various homology against the immunogen, which were obtained using mammalian expression system (ITC). Because of the presence of histidine tags in the recombinant antigens, ELISA was performed using Ni-NTA plates. Preferably for antibody detection, targeted binding of the antigen to Ni-NTA plates provides availability of different epitopes of the antigen. ELISA using MaxiSorp plates (NUNC) was used for the determination of antibody specificity against AIVs. The first supernatant analyses for the presence of anti-AIV of H5 serotype (x-OvO) were performed only after hybridoma cloning (Example 5). Full characterization of antibody specificity against AIVs of H1, H2, H3, H4, H6, H7, H8, H9, H10, H11, H12, H13, H14, H15 and H16 serotype (x-OvO), was performed only for selected and purified clones of mAbs (Example 7). Similarly to tests for the analysis of antibody specificity against H5 HA (Example 3), highly specific anti-mouse antibodies were used as detecting antibodies in the tests for analysis of serotype-specificity of antibodies using rHA, rHA1 and various AIV strains. Thus, antibody selection was limited to the serotype-specific antibodies of the desired class, i.e. IgG.

ELISAs Using Recombinant HA Proteins

In order to perform ELISA using recombinant HA proteins, rHA and rHA1, including rHA-A/H5N1/Qinghai (ITC), were diluted in 1% BSA/PBS and then loaded into Ni-NTA plates (Qiagen). Some wells of the plate were filled in with 1% BSA/PBS and incubated overnight at 2-8° C., in parallel to the antigen-containing wells. Supernatant of non-cloned hybridomas was analyzed without dilution using plates coated with rHA and rHA1 in 1 µg/mL. After hybridoma cloning, culture supernatant was analysed without dilution and/or after dilution in PBS on the plates coated with rHA and rHA1 in 1 and 5 µg/mL concentration, respectively. Samples for reactivity tests with rHA having sequences of A/H5N1/Qinghai, A/H5N1/India, A/H5N1/Vietnam and A/H5N1/Guiyang strains were diluted 1:3000 or 1:3000 and 1:5000. For the tests on rHA-A/H5N2/California-coated plates, supernatants were analysed without dilution or, additionally, in 1:1500 and 1:3000 dilutions. Samples of supernatants for reactivity analysis with the remaining HA antigens were not diluted. In order to control the level of non-specific binding of antibodies, samples prepared from hybridoma culture supernatants were additionally analysed in non-coated wells of the plate. Assay was carried out in the presence of control samples. Positive control was commercial anti-H5 HA antibodies (mAb 8, List A), whereas negative control was RPMI buffer (BLK sample). Plates with the tested and control samples were incubated overnight at 2-8° C. HRP-labelled anti-mouse IgG antibodies (γ-chain specific, Sigma-Aldrich) were used for the detection of antigen-bound mAbs. Secondary antibodies were diluted 1:1000 in 1% BSA/PBST or 2% BSA/PBS and incubated in the plates for 45 min at room temperature or for 60 min at 37° C. TMB (Sigma-Aldrich) was used as a substrate for HRP. Reaction was inhibited using 1.25 M solution of $H_2SO_4$. Absorption of samples was read at $\lambda$=450 nm.

The results of reactivity studies for commercial mAbs and pAbs on Ni-NTA plates coated with rHA and rHA1 with the HA sequence of A/H5N1/Vietnam strain in 1 μg/mL concentration (FIG. 6) and in 0.25-4 μg/mL concentrations (data not shown) showed, that detectability of antibodies against HA1 subunit is lower with the use of rHA1 than rHA for plate coating and it depends on the concentration of antibodies and their affinity for the antigen. Positive signal for samples of supernatants from the cultures of hybridomas tested for rHA and rHA1 clearly indicates, that mAbs are HA1 subunit-specific, whereas positive signal for rHA and no signal for rHA1 does not necessary mean, that mAbs target HA2 subunit of the antigen. After increasing concentration of rHA1 for coating of Ni-NTA plates from 1 μg/mL to 5 μg/mL, the sensitivity of the test for serotype-specificity analysis was increased (data not shown). The test of an increased sensitivity was used to analyse samples of supernatants from hybridoma cultures, after they were cloned.

ELISAs Using Influenza Viruses of H1-16 Serotypes

To perform ELISAs, AIV preparations (x-OvO) were diluted in PBS to 4000 HAU/mL based on the value specified by the manufacturer, and then loaded on the MaxiSorp plates (NUNC). Plates with wells containing viral antigen were incubated overnight at 2-8° C., in parallel to PBS-filled wells. Efficiency of coating with particular viruses could be surprisingly varied due to the observed differences in the composition of preparations. After incubation, plates were blocked with 2% BSA/PBS. Hybridoma culture supernatants were analysed without dilution in the plates coated with AIVs of H5 serotype (positive selection). Purified mAb clones were diluted to 20 μg/mL in 2% BSA/PBS and analysed in the plates coated with AIVs of H5 serotype (positive selection) and of H1-H4 and H5-H16 serotypes (negative selection). A part of each negative selection plate was coated with H5N3 and H5N9 viruses to confirm correct testing for IVs of serotypes other than H5. Samples containing mAbs and BLK samples (RPMI buffer and/or 2% BSA/PBS) loaded into antigen-coated and non-coated wells of the plate, respectively, provide controls for non-specific binding of antibodies. The control was commercial anti-H5 HA antibodies (mAb 8, List A) diluted to 0.05, 0.01, 0.005 and 0.001 μg/mL concentration in 2% BSA/PBS during testing of culture supernatants and to 20 μg/mL during testing of purified mAbs. Plates with the obtained mAbs and control samples were incubated overnight at 2-8° C. HRP-labelled anti-mouse IgG antibodies (γ-chain specific, Sigma-Aldrich) were used for the detection of antigen-bound mAbs. Secondary antibodies were diluted 1:1000 in 2% BSA/PBS and incubated on the plates for 1 h at 37° C. TMB (Sigma-Aldrich) was used as a substrate for HRP. Reaction was inhibited using 0.5 M solution of $H_2SO_4$. Absorption of samples was read at $\lambda$=450 nm.

Summary

Screening of monoclonal antibodies for serotype-specificity was performed with ELISA method using previously characterized H5 HA antigens (positive selection) and IVs of serotypes other than H5 (negative selection). For positive selection, recombinant H5 HA proteins were used based on the ectodomain (rHA) or HA1 subunit (rHA1) of hemagglutinin, described in the List B. Recombinant antigens differed in the amino acid sequence and properties. Individual rHA and rHA1 proteins showed characteristic profiles of recognition by commercial anti-HA antibodies (FIG. 2, 5, 6). Out of ten recombinant proteins, for which antigenicity tests were conducted, nine antigens, including six rHA and three rHA1 proteins, showed structural properties of viral HA. rHA1 antigens were in the form of monomers, whereas rHA antigens were, at least partially, in the form of oligomers (FIG. 3), what makes them similar to trimeric HA from IV envelope. The content of oligomeric forms in rHA antigens was varied. Significantly different level of oligomerization and glycosylation was shown for H5 HA (17-530 aa, ΔRRRKKR (SEQ ID NO: 13), 6×His (SEQ ID NO: 14)) of very similar amino acid sequence: rHA-A/H5N1/Qinghai from mammalian and rHA-A/H5N1/Poland from baculovirus expression system (Examples 2, 3). For positive selection of antibodies, four certified AIV strains of H5 serotypes: H5N1, H5N2, H5N3 and H5N9, were also used (List C). Therefore, antibodies were screened using different forms of H5 HA antigen of preferably varied properties with an expected influence on the presentation of the epitopes for the desired diagnostic monoclonal antibodies. The use of conformational rHA1 proteins enabled identification of mAbs binding to hemagglutinin's HA1 subunit, while the use of protein, which does not show antigenicity of native HA (rHA-A/H5N1/Ck/Vietnam), allows for the differentiation between antibodies recognizing conformational and linear H5 HA epitopes.

In the analysis of serotype specificity of generated antibodies, hemagglutinins were used or their fragments showing characteristics of native antigen, which contained HA sequences of twelve IV strains of H5 serotype (List B and C). This number includes H5N3 (1 strain), H5N9 (1 strain), H5N2 (2 strains) and H5N1 viruses (8 strains), classified into five clades: 0, 1, 2.2, 4 and EA-nonGsGD (List D). Homology of HA1 subunit of conformational HA antigens to HA1 subunit of the immunogen (rHA-A/H5N1/Qinghai), measured as the percentage of identical amino acids in the sequence, was from 99% to 88% (List F). It could be assumed, that the use of different forms of H5 HA antigens with varied homology will enable to evaluate serotype-specificity of novel mAb clones, as the tests for the reactivity of commercial antibodies with recombinant H5 HA proteins revealed the range of specificities of individual clones against H5 hemagglutinins (FIG. 2, 5, 6). Negative selection was performed using twenty-one AIV strains representing HA serotypes other than H5. H1-H4 and H6-H16 AIVs (List C) were certified, just as AIVs of H5 serotype.

In summary, strategy used for the selection of mAbs provided high chance of identification of antibody clones recognizing different epitopes specific for H5 HA, which would react with IVs of H5 serotype, which belong to different clades and subclades, and at the same time would not cross-react with viruses of serotypes other than H5.

Example 5 The Results of Antibody Selection

As a result of the use of procedure for obtaining mAbs using rHA-A/H5N1/Qinghai for mice immunization, described in Example 1, 440 hybridomas were obtained, including 58, which produced anti-H5 HA antibodies. Specificities were determined by ELISA using two antigens: rHA-A/H5N1/Qinghai from mammalian expression system (ITC) and rHA-A/H5N1/Poland from baculovirus expression system (OET). Test conditions are described in Example 3. Supernatants from hybridoma cultures containing rHA-A/H5N1/Qinghai-recognizing antibodies were subjected to further analysis using recombinant HA proteins based on the ectodomain (rHA) and HA1 subunit (rHA1) of hemagglutinin, which were produced in mammalian cells (ITC). Assay was performed as described in Example 4. The results indicating correct conformation of HA proteins used are shown in Examples 2, 3 and 4. Antigens contained HA sequences of five H5N1 virus strains and one H5N2 virus strain. Antigen sequences were analysed in BLAST by comparison with HA sequence of A/Bar-headed Goose/Qinghai/60/05 (H5N1) strain. Homology of full-length, source sequences for HA antigens, expressed as percentage of identical amino acids, was from 99% to 89%, and from 99% to 88% for HA1 subunit-forming sequences. Table 1, below, shows the result of serotype specificity assays for the obtained antibodies.

In particular, Table 1 shows the test results for immunoreactivity of antibodies produced by non-cloned hybridomas. Samples from hybridoma supernatants were tested by ELISA using recombinant proteins based on ectodomain (rHA) and HA1 subunit (rHA1) of hemagglutinin. rHA-A/H5N1/Poland protein was produced in baculovirus expression system (OET, series 1). The remaining rHA and rHA1 proteins were obtained from mammalian expression system (ITC). MediSorp (rHA-A/H5N1/Poland) plates from NUNC and Ni-NTA plates (rHA, rHA1 from mammalian expression system) from Qiagen were used for coating with HA antigens. Homology of hemagglutinins, from which sequences of H5 HA antigens were derived, was determined against 1-567 aa (full-length protein) and 17-338 aa (HA1 subunit) fragments of the HA of A/Bar-headed Goose/Qinghai/60/05 (H5N1) strain, which is the source of immunogen sequence (rHA-A/H5N1/Qinghai). Sequences were compared using BLAST software and expressed as percentage of identical amino acids.

TABLE 1

| HA antigens | Homology HA Ident [%] | | | | | | | | | | | |
|---|---|---|---|---|---|---|---|---|---|---|---|---|
| oryginal sequence | HA1- | HA1 | 58 hybridomas before cloning | | | | | | | | | |
| (IV strain, H5N1 AIV clade) | 567 aa | 17-338 aa | 25 | 3 | 3 | 9 | 4 | 7 | 3 | 2 | 1 | 1 |
| Hemagglutinin ectodomain-based proteins from mammalian expression system (rHA) | | | | | | | | | | | | |
| rHA - A/H5N1/Qinghai<br>A/Bar-headed Goose/Qinghai/12/05<br>clade 2.2 | 100 | 100 | + | + | + | + | + | + | + | + | + | + |
| rHA - A/H5N1/India<br>A/chicken/India/NIV33487/2006<br>clade 2.2 | 99 | 99 | + | + | + | + | + | + | + | + | + | + |
| rHA - A/H5N1/Vietnam<br>A/Vietnam/1203/2004<br>clade 1 | 97 | 95 | + | + | + | + | + | + | + | + | + | + |
| rHA - A/H5N1/Guiyang<br>A/goose/Guiyang/337/2006<br>clade 4 | 94 | 93 | + | + | – | + | + | + | + | – | – | – |
| rHA - A/H5N2/California<br>A/American green-winged teal/<br>California/HKWF609/2007 | 89 | 88 | + | – | + | + | + | – | – | + | – | – |
| Hemagglutinin ectodomain-based protein from baculovirus expression system (rHA) | | | | | | | | | | | | |
| rHA - A/H5N1/Poland<br>A/swan/Poland/305-135V08/2006<br>clade 2.2 | 99 | 99 | + | + | + | + | – | + | – | + | + | – |
| Hemagglutinin HA1 subunit-based protein from mammalian expression system (rHA1) | | | | | | | | | | | | |
| rHA1 - A/H5N1/Vietnam<br>A/Vietnam/1203/2004<br>clade 1 | – | 95 | + | + | + | – | – | – | – | – | – | – |
| ↓<br>6 hybridomas were selected for cloning | | | | | | | | | | | | |

Antibodies produced by the most of non-cloned hybridomas (31/58) recognized recombinant proteins from mammalian and baculovirus expression system, including both rHA and rHA1-A/H5N1/Vietnam. Few hybridomas (6/31) were found to produce antibodies which do not detect proteins with hemagglutinin sequences of the lowest homology to the immunogen, i.e. rHA-A/H5N2/California or rHA-A/H5N1/Guiyang. Tests of the supernatants from the remaining cultures of primary hybridomas (27/58) did not show the presence of rHA1-A/H5N1/Vietnam-recognizing antibodies. Positive signal from rHA-A/H5N1/Vietnam and no signal from rHA1-A/H5N1/Vietnam, observed in the tests of all supernatants from cultures of this group of hybridomas, does not have to indicate, that mAbs are directed against HA2 subunit of the antigen. Rationale behind this interpretation is shown in Example 4. Among 27 hybridomas for which no production of antibodies against rHA1-A/H5N1/Vietnam was shown, 13 produced antibodies recognizing all used rHA proteins from mammalian expression system, while antibodies produced by the remaining 14 hybridomas did not show reactivity against rHA-A/H5N2/California and/or rHA-A/H5N1/Guiyang with the lowest homology to the immunogen. No antibodies recognising baculovirus expression system-derived rHA antigen having HA sequence of the HA from A/H5N1/Poland strain were found in the culture supernatants of some hybridomas (8/27), despite high homology to the immunogen.

Taking into account, that serotype-specific epitopes are localised in HA1 subunit of HA, and reactivity with antigens of varied homology indicates the range of specificities of the obtained antibodies, the most promising material for further screening was the group of 25 primary hybridomas, which produced antibodies recognizing all antigens used in the serotype-specificity test. From this group, six hybridomas were chosen for cloning: G-1-31, G-2-14, G-5-32, G-6-42, G-7-24 and G-7-27. Immunoreactivity profiles obtained in the tests of supernatants from cultures of selected hybridomas are shown below, in Table 2. The results are shown as signal values ($A_{450}$) obtained in ELISAs using recombinant HA proteins.

In particular, Table 2 shows the results of immunoreactivity tests of antibodies produced by hybridomas selected for cloning. Tests were performed by ELISA using recombinant proteins based on ectodomain (rHA) and HA1 subunit (rHA1) of hemagglutinin. rHA-A/H5N1/Poland protein was produced in baculovirus expression system (OET, series 1). The remaining rHA and rHA1 proteins were obtained from mammalian expression system (ITC). MediSorp (rHA-A/H5N1/Poland) plates from NUNC and Ni-NTA plates (rHA, rHA1 from mammalian expression system) from Qiagen were used for coating with HA antigens. The results are shown as signal values ($A_{450}$) obtained from the analyses of hybridoma culture supernatants. Homology of hemagglutinins, from which sequences of H5 HA antigens were derived, was determined against 1-567 aa (full-length protein) and 17-338 aa (HA1 subunit) fragments of the HA of A/Bar-headed Goose/Qinghai/60/05 (H5N1) strain, which is the source of immunogen sequence (rHA-A/H5N1/Qinghai). Sequences were compared using BLAST software and expressed as percentage of identical amino acids.

In the tests for serotype-specificity of antibodies produced by the selected hybridoma using rHA antigen from mammalian expression system and rHA-A/H5N1/Poland from baculovirus expression system, signals ($A_{450}$) of very high ($A_{450}$>4) and high (~2.6-~3.3) values were obtained. Using rHA1-A/H5N1/Vietnam for tests, lower $A_{450}$ values were read than in case of rHA1-A/H5N1/Vietnam (~1.2-~3.6 vs >4), which confirms earlier observations regarding lower detection sensitivity for antibodies against HA1 subunit of HA with the use of short fragments of the protein (1-345 aa) under applied test conditions.

Cloning of selected hybridomas: G-1-31, G-2-14, G-5-32, G-6-42, G-7-24 and G-7-27 provided 64 clones producing anti-H5 HA antibodies. Specificity of the obtained mAbs against rHA-A/H5N1/Qinghai and rHA-A/H5N1/Poland and their isotyping were determined by ELISA, as described in Example 3. Hybridoma culture supernatants were subjected to further analysis for the presence of serotype-specific antibodies. Comparing to the tests performed with the use of supernatants from uncloned hybridoma cultures, tests for serotype-specificity of antibodies produced by cloned hybridomas was performed using panel of HA antigens, which was broadened by two recombinant, HA1 subunit-based proteins from mammalian expression system: rHA1-A/H5N1/HK/156 and rHA1-A/H5N1/HK/483 (ITC) and AIVs: H5N1, H5N2, H5N3 and H5N9 (x-OvO). The results of antigenicity analysis indicating correct conformation of rHA1 antigens used are shown in FIG. 6 and are described in Example 4. AIVs are shown in the List C and are described in Example 4. Sequences of antigens: rHA1-A/H5N1/HK/156 and rHA1-A/H5N1/HK/483, comprised 95% and 94%, respectively, identical amino acids to HA1 subunit of the immunogen, whereas sequences forming HA1 subunit of hemagglutinin in viral particles: 93-90%. Into the panel of antigens, rHA-A/H5N1/Ck/Vietnam antigen was

TABLE 2

| HA antigens | Homology HA Ident [%] | | | | | | | |
|---|---|---|---|---|---|---|---|---|
| oryginal sequence | HA1- | HA1 | Hybridomas selected for cloning (no.) | | | | | |
| (IV strain, H5N1 AIV clade) | 567 aa | 17-338 aa | G-1-31 | G-2-14 | G-5-32 | G-6-42 | G-7-24 | G-7-27 |
| Hemagglutinin ectodomain-based proteins from mammalian expression system (rHA) | | | | | | | | |
| rHA - A/H5N1/Qinghai A/Bar-headed Goose/Qinghai/12/05 clade 2.2 | 100 | 100 | >4.0 | >4.0 | >4.0 | >4.0 | >4.0 | >4.0 |
| rHA - A/H5N1/India A/chicken/India/NIV33487/2006 clade 2.2 | 99 | 99 | >4.0 | >4.0 | >4.0 | >4.0 | >4.0 | >4.0 |
| rHA - A/H5N1/Vietnam A/Vietnam/1203/2004 clade 1 | 97 | 95 | >4.0 | >4.0 | >4.0 | >4.0 | >4.0 | >4.0 |
| rHA - A/H5N1/Guiyang A/goose/Guiyang/337/2006 clade 4 | 94 | 93 | >4.0 | >4.0 | >4.0 | >4.0 | >4.0 | >4.0 |
| rHA - A/H5N2/California A/American green-winged teal/ California/HKWF609/2007 | 89 | 88 | >4.0 | >4.0 | >4.0 | >4.0 | >4.0 | 3.784 |
| Hemagglutinin ectodomain-based protein from baculovirus expression system (rHA) | | | | | | | | |
| rHA - A/H5N1/Poland A/swan/Poland/305-135V08/2006 clade 2.2 | 99 | 99 | 3.143 | 2.594 | 3.220 | 3.343 | 3.104 | 3.335 |
| Hemagglutinin HA1 subunit-based protein from mammalian expression system (rHA1) | | | | | | | | |
| rHA1 - A/H5N1/Vietnam A/Vietnam/1203/2004 clade 1 | — | 95 | 1.532 | 1.244 | 1.861 | 3.638 | 1.670 | 1.975 |

also added, which did not show any features of native HA structure in antigenicity and oligomerization studies (FIG. 6) of recombinant proteins described in Example 4. Serotype-specificity of the obtained mAbs was determined by ELISA under conditions described in Example 4. Table 3, below, shows the result of serotype-specificity analysis for the obtained clones of mAbs.

In particular, Table 3 shows the test results for immunoreactivity of antibodies produced by cloned hybridomas. Tests were performed by ELISA using recombinant proteins based on ectodomain (rHA) and HA1 subunit (rHA1) of hemagglutinin, as well as AIV of H5 serotype. rHA-A/H5N1/Poland protein was produced in baculovirus expression system (OET). The remaining rHA and rHA1 proteins were produced in mammalian expression system (ITC). Influenza viruses of H5 serotype (x-OvO) were derived from IZSVe. MediSorp (rHA-A/H5N1/Poland, series 3), MaxiSorp (AIV) plates from NUNC and Ni-NTA plates (rHA, rHA1 from mammalian expression system) from Qiagen were used for coating with HA antigens. Homology of hemagglutinins, from which sequences of H5 HA antigens were derived, was determined against 1-567 aa (full-length protein) and 17-338 aa (HA1 subunit) fragments of the HA of A/Bar-headed Goose/Qinghai/60/05 (H5N1) strain, which is the source of immunogen sequence (rHA-A/H5N1/Qinghai). Sequences were compared using BLAST software and expressed as percentage of identical amino acids.

TABLE 3

| HA antigens<br>Recombinant HA protein<br>original sequence<br>(IV strains, H5N1 AIV clade)<br>Influenza virus<br>(serotype, IV strain, H5N1 AIV clade) | Homology HA Ident [%]<br>HA1-<br>567 aa | <br>HA1<br>17-338 aa | Hybridomas before cloning (no.)<br>G-1-31<br>64 hybridomas after cloning<br>22 | <br>G-2-14<br><br>1 | <br>G-5-32<br><br>10 | <br>G-6-42<br><br>6 | <br>G-7-24<br><br>14 | <br>G-7-27<br><br>11 |
|---|---|---|---|---|---|---|---|---|
| Hemagglutinin ectodomain-based proteins from mammalian expression system (rHA) | | | | | | | | |
| rHA - A/H5N1/Qinghai A/Bar-headed Goose/Qinghai/12/05, clade 2.2 | 100 | 100 | + | + | + | + | + | + |
| rHA - A/H5N1/India A/chicken/India/NIV33487/2006, clade 2.2 | 99 | 99 | + | + | + | + | + | + |
| rHA - A/H5N1/Vietnam A/Vietnam/1203/2004, clade 1 | 97 | 95 | + | + | + | + | + | + |
| rHA - A/H5N1/Guiyang A/goose/Guiyang/337/2006, clade 4 | 94 | 93 | + | + | + | + | + | + |
| rHA - A/H5N1/Ck/Vietnam [1] A/chicken/Vietnam/NCVD-016/08, clade 7 | 91 | 89 | – | – | – | – | – | – |
| rHA - A/H5N2/California A/American green-winged teal/ California/HKWF609/2007 | 89 | 88 | + | + | + | + | + | + |
| Hemagglutinin ectodomain-based protein from baculovirus expression system (rHA) | | | | | | | | |
| rHA - A/H5N1/Poland A/swan/Poland/305-135V08/2006, clade 2.2 | 99 | 99 | + | + | + | + | + | + |
| Hemagglutinin HA1 subunit-based proteins from mammalian expression system (rHA1) | | | | | | | | |
| rHA1 - A/H5N1/Vietnam A/Vietnam/1203/2004, clade 1 | – | 95 | + | + | + | + | + | + |
| rHA1 - A/H5N1/HK/156 A/Hong Kong/156/97, clade 0 | – | 95 | + | + | + | + | + | + |
| rHA1 - A/H5N1/HK/483 A/Hong Kong/483/1997, clade 0 | – | 94 | + | + | + | + | + | + |
| H5 serotype influenza viruses | | | | | | | | |
| IV - H5N3 A/duck/Italy/775/2004 | 93 | 93 | + | + | + | + | + | + |
| IV - H5N1 A/mallard/Italy/3401/2005, clade EA-nonGsGD | 93 | 93 | + | + | + | + | + | + |
| IV - H5N9 A/chicken/Italy/22A/1998 | 91 | 90 | + | + | + | + | + | + |
| IV - H5N2 A/turkey/Italy/1980 | 91 | 90 | + | + | + | + | + | + |
| mAb isotype | | | IgG1 | IgG1 | IgG1 | IgG1 | IgG1 | IgG1 |

TABLE 3-continued

| HA antigens Recombinant HA protein original sequence | | | Hybridomas before cloning (no.) | | | | | |
|---|---|---|---|---|---|---|---|---|
| (IV strains, H5N1 AIV clade) | Homology HA Ident [%] | | G-1-31 | G-2-14 | G-5-32 | G-6-42 | G-7-24 | G-7-27 |
| Influenza virus | HA1- | HA1 | 64 hybridomas after cloning | | | | | |
| (serotype, IV strain, H5N1 AIV clade) | 567 aa | 17-338 aa | 22 | 1 | 10 | 6 | 14 | 11 |
| Selected hybridomas: G-1-31-22, G-2-14-10, G-5-32-5, G-6-42-42, G-6-42-71, | | | ↓ 1 clon | ↓ 1 clon | ↓ 1 clon | ↓ 2 clon | ↓ 1 clon | ↓ 1 clon |

[1] Antygen showing non-native hemagglutinin conformation

Obtained mAb clones, all of IgG1 isotype, recognized conformational HA antigens: rHA (5/5) and rHA1 (3/3) from mammalian expression system, rHA-A/H5N1/Poland from baculovirus expression system, and H5 HA in viral particles (4/4). None of the obtained mAb clones was binding to rHA-A/H5N1/Ck/Vietnam, which showed no characteristics of native HA. In a situation, where all obtained mAb clones showed desired, broad range of specificities against H5 HA (Table 3), few clones of mAbs derived from cloning of each of the six primary hybridomas, were selected for further analysis. By this approach, probability of finding clones recognizing different epitopes specific for H5 serotype of hemagglutinin, was increased. One mAb clone was selected from each of hybridomas: G-1-31, G-5-32, G-7-24 and G-7-27, and 2 mAb clones were selected from G-6-42 hybridoma. One G-2-14-10 clone obtained from cloned G-2-14 hybridoma was also selected for further characterization.

Selected clones of G-1-31-22, G-2-14-10, G-5-32-5, G-6-42-42, G-6-42-71, G-7-24-17 and G-7-27-18 antibodies were purified from hybridoma culture supernatants using "HiTrap Protein G HP" (GE Healthcare). Preparation was according to manufacturer's instructions. 0.1 M glycine-HCl buffer, pH 2.7, was used for the elution of mAbs. Protein fractions were neutralized during elution using 1 M Tris-HCl, pH 9.0. Buffer exchange and antibody concentrations were performed by centrifugation in "Vivaspin® 6 Centrifugal Concentrator", 10 000 MWCO (Sartorius Stedim Biotech). Purified mAbs: G-1-31-22, G-2-14-10, G-5-32-5, G-6-42-42, G-6-42-71, G-7-24-17 and G-7-27-18 were tested using mass spectrometry and ELISAs for the analysis of serotype-specificity. Differentiation of the above mentioned antibody clones was performed based on the immunoreactivity profiles and peptide maps of Fab fragments. In order to evaluate the ability of generated mAbs to inhibit hemagglutination, HI testes were carried out. Test results are shown in subsequent Examples 6-10. Possible applications of the obtained antibodies are described in Examples 11 and 12. The object of the present patent application are monoclonal antibodies specific to HA of H5 serotype IVs: G-1-31-22, G-2-14-10, G-5-32-5, G-6-42-42, G-6-42-71, G-7-24-17 and G-7-27-18 and their use.

Example 6 Mass Spectra of the Selected Antibody Clones

Purified clones of antibodies: G-1-31-22, G-2-14-10, G-5-32-5, G-6-42-42, G-6-42-71, G-7-24-17 and G-7-27-18, chosen as a result of the selection for serotype-specificity (Table 3) and described in Example 5, were analysed using MALDI TOF/TOF mass spectrometer (4800 Plus, AB SCIEX). Before performing mass spectrometry, the samples were purified using ZipTip®$_{C4}$ (Millipore) according to the procedures included in the manufacturer's instruction: "User Guide for Reversed-Phase ZipTip". The matrix was sinapinic acid (Fluka) in 5 mg/mL concentration, dissolved in 0.1% trifluoroacetic acid containing 50% of acetonitrile. Mass spectra were measured in the linear mode (MS Linear Positive Ion), in the range of 20-170 kDa. External calibration was achieved with IgG standard (AB SCIEX). All mass spectra were processed using Gaussian filter and the procedures for signal detection with the use of Data Explorer Software (V4.9).

Figure 7A:
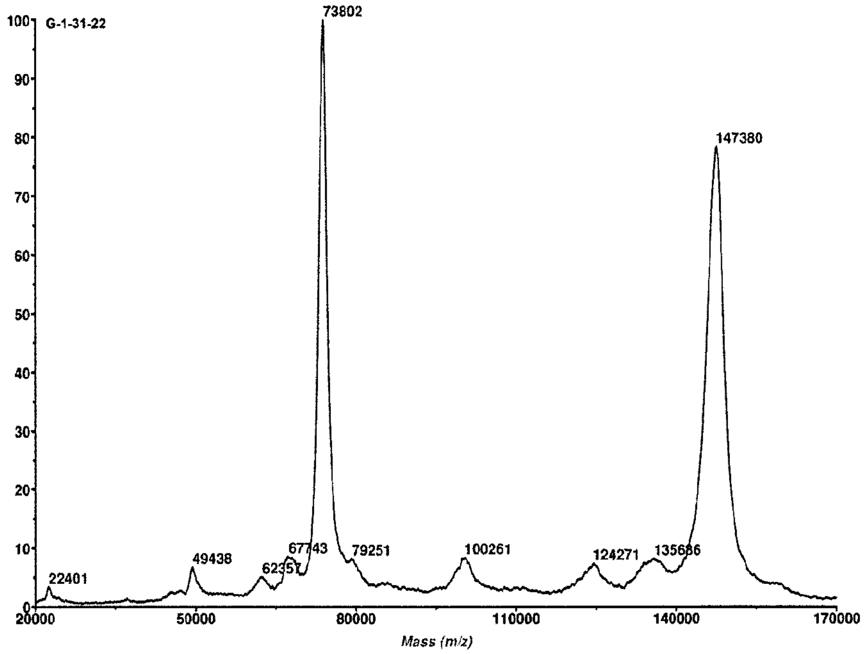
FIG. 7*a*-*g* show mass spectra of produced mAbs: (a) G-1-31-22, (b) G-2-14-10, (c) G-5-32-5, (d) G-6-42-42, (e) G-6-42-71, (f) G-7-24-17, (g) G-7-27-18. Mass spectra were obtained using MALDI TOF/TOF (4800 Plus, AB SCIEX) mass spectrometer.
Figure 7B:
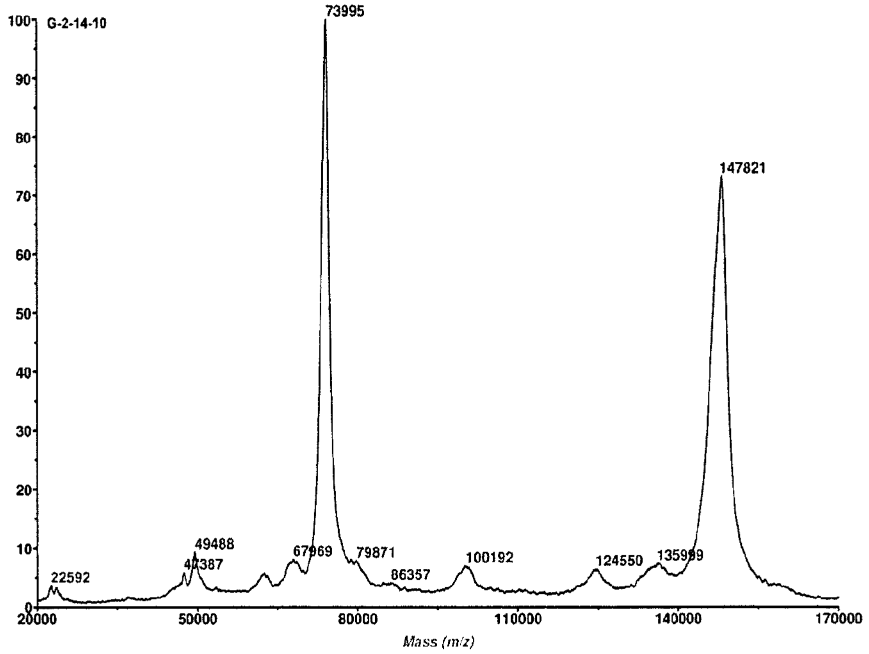
Figure 7C:
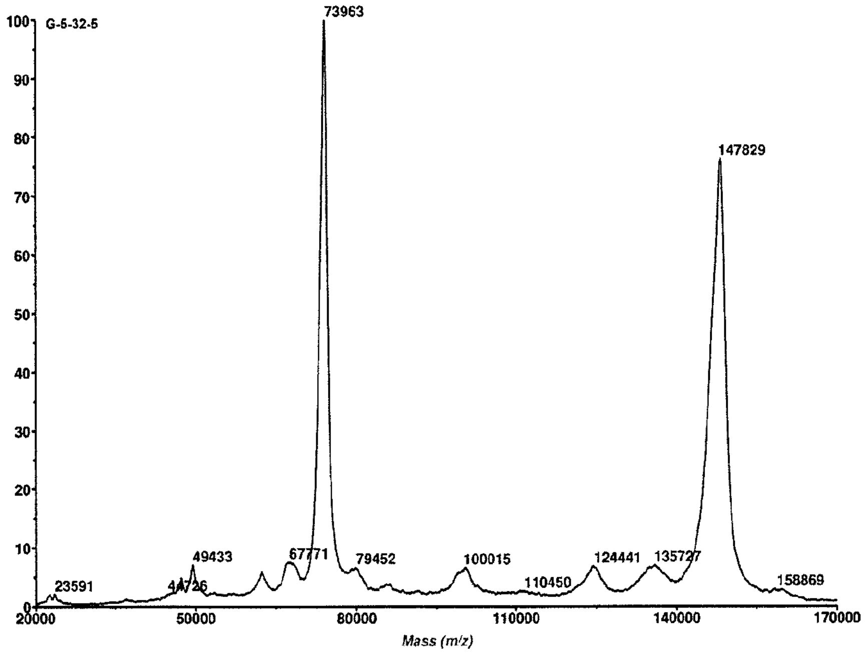
Figure 7D:
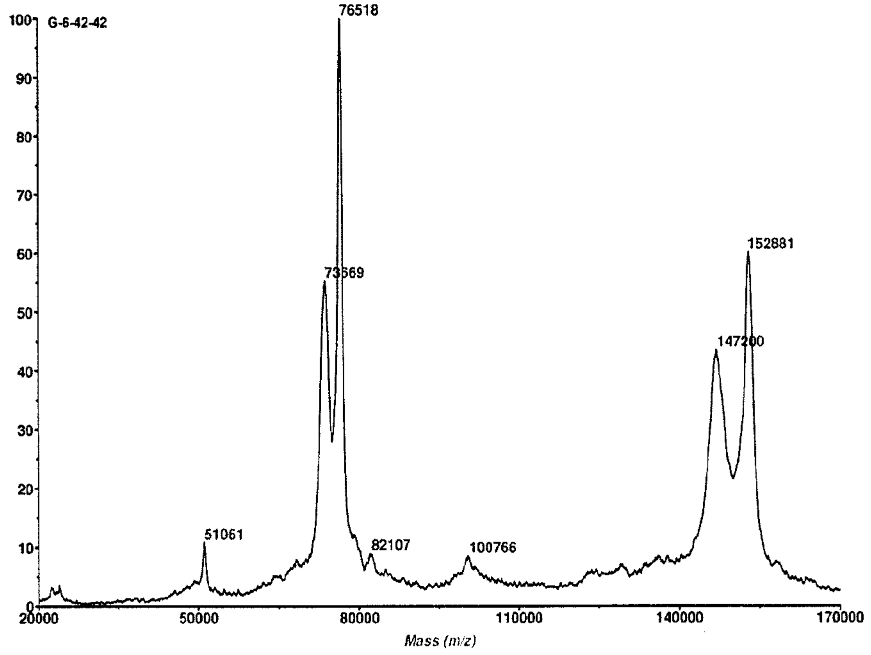
Figure 7E:
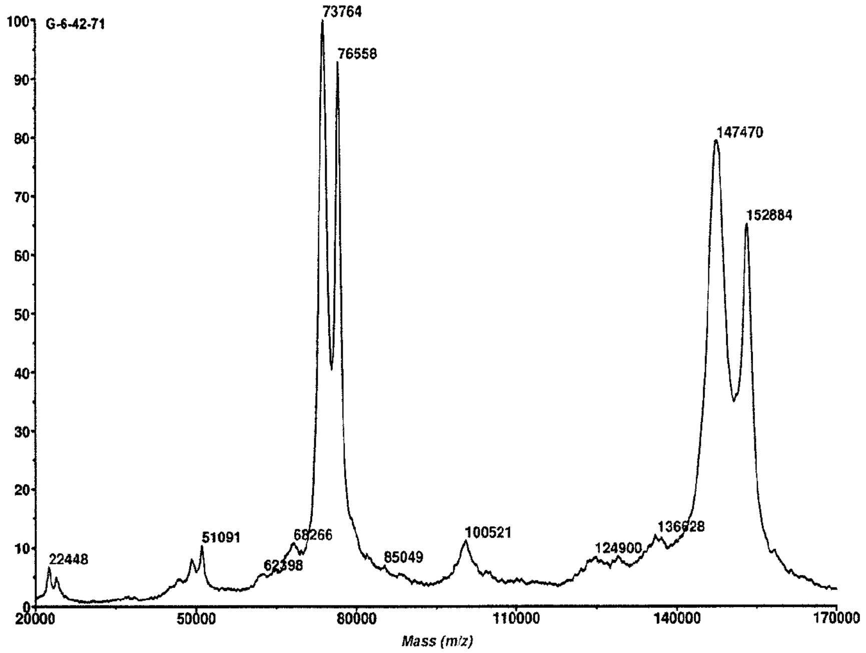
Figure 7F:
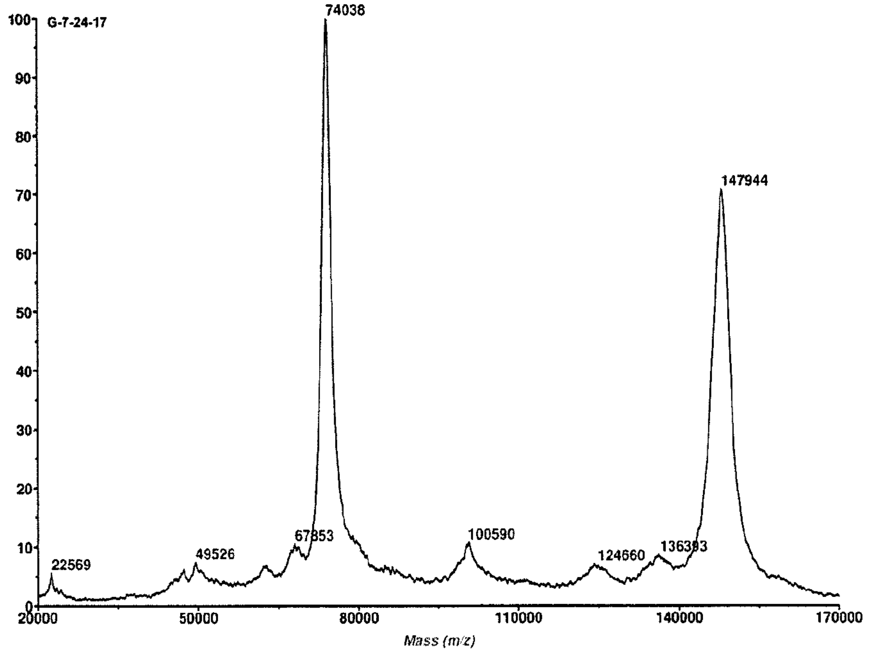
Figure 7G:
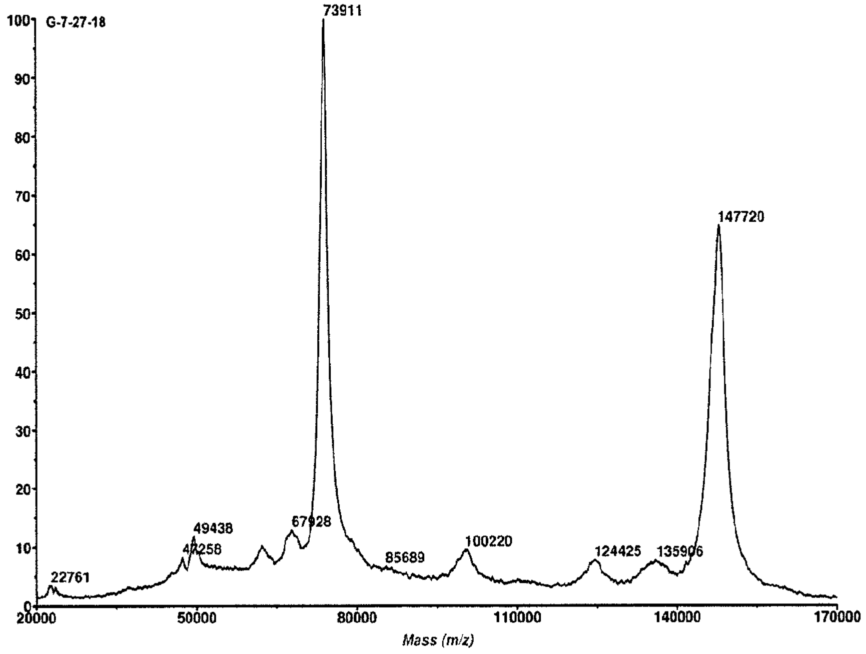

FIG. 7*a-g* shows mass spectra of purified anti-H5 HA mAbs: G-1-31-22, G-2-14-10, G-5-32-5, G-6-42-42, G-6-42-71, G-7-24-17 and G-7-27-18. Molecular weight signals in the range of 147-153 kDa and 74-77 kDa represent tested antibodies and correspond to singly- and doubly-ionized samples, respectively. Determined molecular weights are in line with values expected for mouse IgG antibodies. Differences in spectra of the individual clones may result from different protein glycosylation. Molecular weight of G-1-31-22 mAb is 147 kDa, while of G-2-14-10, G-5-32-5, G-7-24-17 and G-7-27-18 mAbs is 148 kDa. Mass spectra of G-6-42-42 and G-6-42-71 mAb, obtained by cloning primary G-6-42 hybridoma (Table 3), indicate presence of 2 antibody forms having molecular weights of 147 kDa and 153 kDa (FIG. 7*d,e*). Presumably, those 2 antibody forms differ in the level of glycosylation, and higher molecular weight proteins were formed as a result of additional, non-enzymatic glycosylation.

Relationship between an increase in molecular weights of antibodies and an increased level of non-enzymatic glycosylation was well documented in the studies of immunoglobulin fractions from diabetic patients (Lapolla A. et al., 1997, 2000a, 2000b). For example, molecular weights of IgG antibodies from healthy individuals and antibody standard, determined with the use of mass spectrometer, were 149 kDa and 148 kDa, respectively, and 152 kDa for antibodies in protein fraction from patients with poorly-controlled diabetes (Lapolla A. et al., 1997, 2000a). The effect of an increased non-enzymatic glycosylation was also obtained in vitro, by incubating protein fraction from plasma of healthy individual or IgG antibody standard in the presence of high glucose concentrations, when an increase of antibody molecular weight was observed, from 149 kDa and 148 kDa to 153 kDa, respectively (Lapolla A. et al., 2000a).

Example 7 Reactivity of Selected Antibody Clones with Hemagglutinin Antigens Monoclonal antibodies: G-1-31-22, G-2-14-10, G-5-32-5, G-6-42-42, G-6-42-71, G-7-24-17 and G-7-27-18, chosen as a result of the selection for serotype-specificity (Table 3), were purified by affinity chromatography, as described in Example 5. In further studies, reactivity of selected mAb clones with HA of H1-H16 serotypes was determined in order to evaluate specificity and affinity mAbs for H5 HA of different IV strains, and their ability to cross-react with HA of serotypes other than H5. The studies were carried out using H5 HA antigens with different properties. Among those antigens, there were recombinant proteins based on the ectodomain (rHA) or HA1 subunit (rHA1) of hemagglutinin and AIV of H5 serotype (List B and C). Recombinant HA proteins from mammalian and, exceptionally, baculovirus expression system, contained HA1 subunit of, usually, correct conformation, were in monomeric forms (rHA1) or, mostly or partially, formed oligomeric forms (rHA). Four certified AIV strains of H5 serotype: H5N1, H5N2, H5N3 and H5N9 were used in the studies of the obtained mAbs. Conformational antigens contained HA sequences from twelve IV strains of H5 serotype, with varied homology to the immunogen (rHA-A/H5N1/Qinghai)—percentage of identical amino acids in the sequences of HA1 subunit of proteins used in the studies was from 99% to 88% (List F). Antigens: rHA-A/H5N1/Qinghai from mammalian expression system and rHA-A/H5N1/Poland from baculovirus expression system, are described in detail in Examples 2 and 3, respectively, whereas the remaining H5 HA antigens, produced in mammalian cells, are described in Example 4.

Comparing to the tests performed for the supernatants from G-1-31-22, G-2-14-10, G-5-32-5, G-6-42-42, G-6-42-71, G-7-24-17 and G-7-27-18 hybridoma cultures (Example 5), the assays for serotype-specificity of antibodies purified from the supernatants of those hybridomas were performed using panel of antigens, which additionally contained HA ectodomain-based recombinant protein from bacterial expression system and AIVs of H1-H4 and H6-H16 serotypes. The protein (17-522 aa, ΔRRRKKR (SEQ ID NO: 13)) with HA sequence of A/swan/Poland/305-135V08/2006 (H5N1) strain of AIV, was over-expressed in *Escherichia coli* in The Institute of Biotechnology and Antibiotics (Instytut Biotechnologii i Antybiotyków, IBA) in Warsaw (Poland). Following purification and renaturation, the H5 HA protein was subjected to the analyses with the use of mass spectrometry, ELISAs for HA proteins antigenicity and oligomerization studies, similarly to other recombinant H5 HA antigens. In the immunoreactivity tests, antigen preparation of ~80% purity was used. Molecular weight of rHA-A/H5N1/Poland protein from bacterial system, determined using MALDI TOF/TOF mass spectrometer (4800 Plus, AB SCIEX), was 57 kDa. Contrary to the results obtained for rHA-A/H5N1/Qinghai and rHA-A/H5N1/Poland proteins from mammalian and baculovirus expression system (Examples 2, 3), respectively, experimentally determined molecular weight of bacterial HA was in line with the weight calculated on the basis of amino acid composition in GPMAW 8.2 programme (Lighthouse). This is due to the fact, that proteins produced in bacteria do not undergo glycosylation. Conducted analyses revealed, that produced protein has features of native antigen: it retains conformational epitopes recognized by commercial anti-H5 HA antibodies (List A), including also HI antibodies, and it forms oligomeric structures. Two antigenic variants of the protein were prepared in the IBA. In the tests described in the present Example and in Examples 8 and 11, the second antigenic variant was used. In the tests of purified mAbs, twenty-one certified AIV strains representing H1-H4 and H6-H16 serotypes (List C) were used.

Specificity for H5 HA

Specificity of purified mAbs: G-1-31-22, G-2-14-10, G-5-32-5, G-6-42-42, G-6-42-71, G-7-24-17 and G-7-27-18 against H5 HA was tested by titrating them against rHA-A/H5N1/Qinghai protein from mammalian expression system (ITC), which was used as the immunogen in antibody producing procedure (Examples 1, 2). Also, titration against rHA-A/H5N1/Poland from baculovirus (OET) and bacterial expression system (IBA) with high homology to the immunogen (Lists: E, F), was performed.

To perform the assay, rHA-A/H5N1/Qinghai (ITC) and rHA-A/H5N1/Poland (OET, series 8), diluted in PBS to 1 μg/mL concentration, were loaded into MediSorp plates (NUNC), and rHA-A/H5N1/Poland preparation (IBA) of ~80% purity, containing renatured hemagglutinin in ~1 μg/mL PBS, was loaded into PolySorp, MediSorp, MaxiSorp and MultiSorp plates (NUNC). Some wells of the plate were filled in with PBS instead of the antigen solution. Following the overnight incubation at 2-8° C., the plates were blocked with 10% FBS/PBS. Purified mAb clones were analysed as series of 2-fold dilutions in 2% BSA/PBS. Antibodies diluted in a range of 8 μg/mL-0.015 ng/mL were loaded into the plates coated with antigens from mammalian and baculovirus expression system, whereas antibodies diluted in a range of 8 μg/mL-7.8 (3.9) ng/mL were loaded into the plates coated with the protein from bacterial expression system. The level of non-specific antibody binding was controlled by samples containing antibodies in 4 μg/mL and/or 8 μg/mL concentration and 2% BSA/PBS (BLK sample) loaded into non antigen-coated and coated wells, respectively. Plates with the obtained mAbs and control samples were incubated overnight at 2-8° C. HRP-labelled anti-mouse IgG antibodies (γ-chain specific, Sigma-Aldrich) were used for the detection of antigen-bound mAbs. Secondary antibodies were diluted 1:1000 in 2% BSA/PBS and incubated on the plates for 1 h at 37° C. TMB (Sigma-Aldrich) was used as a substrate for HRP. Reaction was inhibited using 0.5 M solution of $H_2SO_4$. Absorption of samples was read at λ=450 nm.

Figure 8:
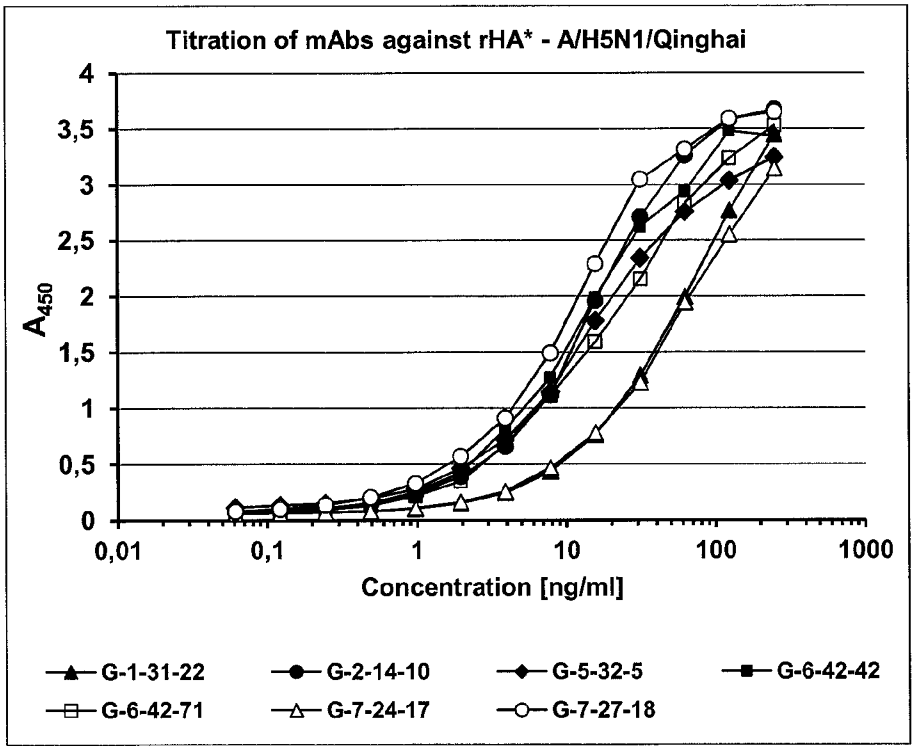
FIG. 8 shows titration curves of mAbs: G-1-31-22, G-2-14-10, G-5-32-5, G-6-42-42, G-6-42-71, G-7-24-17 and G-7-27-18 on rHA-A/H5N1/Qinghai from (*) mammalian expression system. The protein (17-530 aa, ΔRRRKKR (SEQ ID NO: 13), 6×His (SEQ ID NO: 14)) was produced based on the sequence of HA of A/Bar-headed Goose/Qinghai/12/05 (H5N1) strain of AIV (ITC). The assay was performed by ELISA on MediSorp plates (NUNC) coated with 1 μg/mL antigen.
Figure 9:
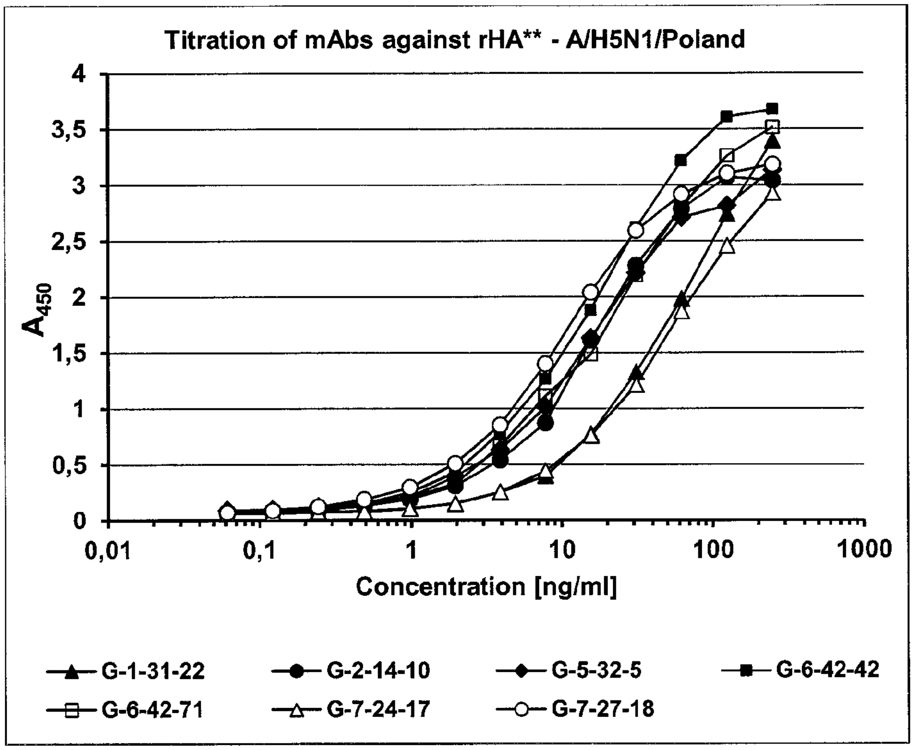
FIG. 9 shows titration curves of mAbs: G-1-31-22, G-2-14-10, G-5-32-5, G-6-42-42, G-6-42-71, G-7-24-17 and G-7-27-18 on rHA-A/H5N1/Poland from (**) baculovirus expression system. The protein (17-530 aa, ΔRRRKKR (SEQ ID NO: 13), 6×His (SEQ ID NO: 14)) was produced based on the sequence of HA of A/swan/Poland/305-135V08/2006 (H5N1) strain of AIV (OET, series 8). The assay was performed by ELISA on MediSorp plates (NUNC) coated with 1 μg/mL antigen.
Figure 10:
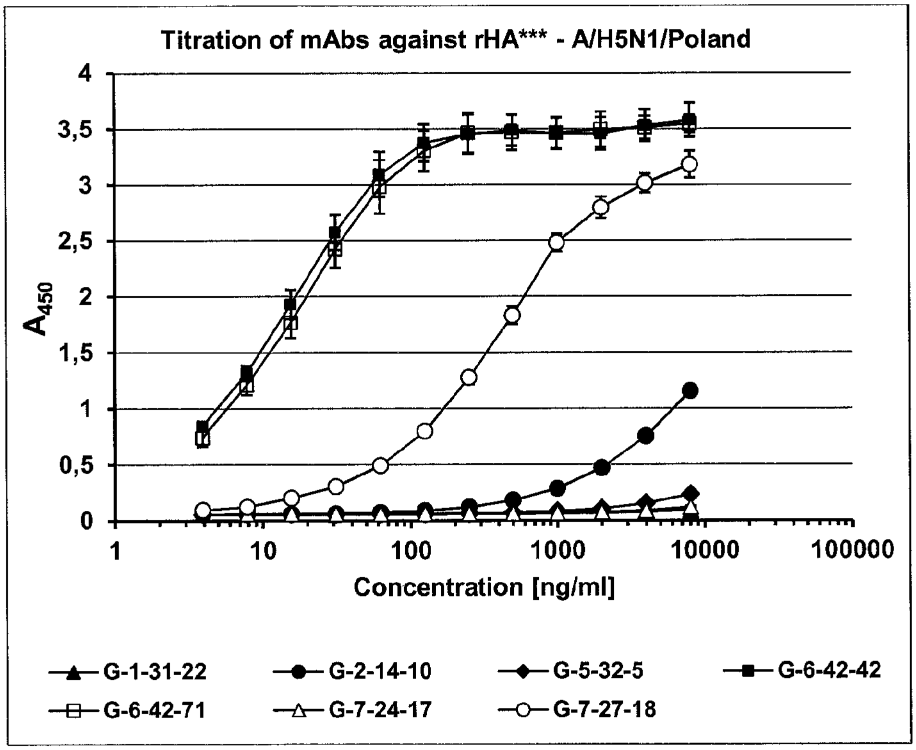
FIG. 10 shows titration curves of mAbs: G-1-31-22, G-2-14-10, G-5-32-5, G-6-42-42, G-6-42-71, G-7-24-17 and G-7-27-18 on rHA-A/H5N1/Poland from (***) bacterial expression system. The protein (17-522 aa, ΔRRRKKR (SEQ ID NO: 13)) was produced based on the sequence of HA of A/swan/Poland/305-135V08/2006 (H5N1) strain of AIV (IBA). The assay was performed by ELISA on PolySorp, MediSorp, MaxiSorp and MultiSorp plates (NUNC) coated with rHA preparation with purity ~80%, which contained renatured hemagglutinin in ~1 μg/mL concentration. The results are shown as mean values $A_{450}$±SD obtained using particular type of polystyrene plates.

Titration curves of mAbs: G-1-31-22, G-2-14-10, G-5-32-5, G-6-42-42, G-6-42-71, G-7-24-17 and G-7-27-18 against rHA-A/H5N1/Qinghai from mammalian expression system is shown in FIG. 8, and against na rHA-A/H5N1/Poland from baculovirus and bacterial expression system in FIG. 9 and FIG. 10, respectively. The results suggest, that all tested mAb clones have high affinity for antigens from eukaryotic expression system—high levels of signals ($A_{450}$) were obtained for antibody concentrations in nanogram range (FIG. 8, 9). No significant differences were observed between titration curves for individual antibodies against antigens from mammalian and baculovirus expression system. The results of immunoreactivity studies for particular mAb clones with bacterial rHA-A/H5N1/Poland protein bound to PolySorp, MediSorp, MaxiSorp and MultiSorp plated (NUNC), were similar, therefore they are presented as mean values $A_{450}$±SD, obtained for particular type of plates (FIG. 10). Reactivity with the antigen was shown for G-2-14-10, G-6-42-42, G-6-42-71 and G-7-27-18 antibodies, wherein high $A_{450}$ values were obtained for nanogram (G-6-42-42, G-6-42-71, G-7-27-18) or microgram (G-2-14-10) ranges of antibody concentrations. Under conditions used in the assay, very weak reactivity of G-5-32-5 mAb and no reactivity of G-1-31-22 and G-7-24-17 mAbs for bacterial H5 HA protein were found.

Concentrations, at which the levels of ($A_{450}$) signal were 1.5 and/or 1.0, were determined using Gene5 software (Bio-Tek), by interpolation from linear segments of 4-parametric titration curves. Table 4, below, shows interpolated values obtained for the individual clones of mAbs.

In particular, Table 4 shows concentration of mAbs: G-1-31-22, G-2-14-10, G-5-32-5, G-6-42-42, G-6-42-71, G-7-24-17, G-7-27-18, determined by interpolation from linear ranges of 4-parametric titration curves against recombinant HA proteins with high homology to the immunogen. rHA*-A/H5N1/Qinghai protein (17-530 aa, ΔRRRKKR (SEQ ID NO: 13), 6×His (SEQ ID NO: 14)) with HA sequence derived from A/Bar-headed Goose/Qinghai/12/05 (H5N1) strain of AIV was produced in (*) mammalian expression system (ITC). rHA-A/H5N1/Poland (17-530 aa, ΔRRRKKR (SEQ ID NO: 13), 6×His (SEQ ID NO: 14)) and rHA*-A/H5N1/Poland (17-522 aa, ΔRRRKKR (SEQ ID NO: 13)) were produced in () baculovirus (OET, series 8) and (*) bacterial expression system (IBA), respectively, based on the HA sequence derived from A/swan/Poland/305-135V08/2006 (H5N1) strain of AIV. The analysis was performed by ELISA. Titration of HA protein from mammalian and baculovirus expression system was performed using MediSorp plates (NUNC) coated with the antigens in 1 μg/mL concentration, and the results are shown as concentration values interpolated for the level of ($A_{450}$) signal, i.e. 1.5. Titration against HA protein from bacterial expression system was performed on PolySorp, MediSorp, MaxiSorp and MultiSorp plates (NUNC) coated with rHA preparation with purity ~80%, which contained renatured hemagglutinin in ~1 μg/mL concentration. The results are shown as means of concentration values (±SD) interpolated for $A_{450}$ levels of 1.0 and/or 1.5, obtained by assays performed with the use of particular type of polystyrene plates. Titration curves and interpolated values were determined using Gene5 software (Bio-Tek).

TABLE 4

| mAb clones | mAb concentration for $A_{450}$ = 1.5 [ng/mL] rHA* A/H5N1/ Qinghai | rHA** A/H5N1/ Poland | rHA*** A/H5N1/ Poland | mAb concentration for $A_{450}$ = 1.0 [ng/mL] rHA*** A/H5N1/ Poland |
|---|---|---|---|---|
| G-1-31-22 | 39 | 38 | — | — |
| G-2-14-10 | 11 | 15 | — | ~6368 ± 157 |
| G-5-32-5 | 13 | 14 | — | — |
| G-6-42-42 | 9 | 10 | ~10 ± 1 | ~5 ± 1 |
| G-6-42-71 | 14 | 14 | ~12 ± 2 | ~6 ± 1 |
| G-7-24-17 | 39 | 43 | — | — |
| G-7-27-18 | 7 | 9 | ~322 ± 28 | ~161 ± 12 |

*mammalian,
**baculovirus,
***bacterial expression system

Values interpolated from titration curves of mAbs: G-2-14-10, G-5-32-5, G-6-42-42, G-6-42-71, G-7-27-18 against rHA-A/H5N1/Qinghai from mammalian expression system and rHA-A/H5N1/Poland from baculovirus expression system for $A_{450}$=1.5 reached values in the range of 7-14 ng/mL and 9-15 ng/mL, respectively, and in the case of G-1-31-22 and G-7-24-17 mAbs, they were 39 ng/mL and 39 ng/mL, and 38 ng/mL, respectively. Values interpolated from titration curves of G-6-42-42, G-6-42-71 mAbs against rHA-A/H5N1/Poland from bacterial expression system for $A_{450}$=1.5 reached values of ~10 ng/mL±1 and ~12 ng/mL±2, respectively, and which were comparable to the values obtained by titration of those antibodies against antigens from eukaryotic expression system. In case of G-7-27-18 mAb titration, concentration interpolated for $A_{450}$=1.5 from the titration curve against bacterial HA protein was ~322 ng/mL±28 and was, in average, 41-fold higher than against antigens derived from mammalian and baculovirus expression system. Within the range of used G-2-14-10 mAb dilutions, concentration interpolated for $A_{450}$=1.0 from the titration curve against bacterial HA protein was ~6368 ng/mL±157, and was over 1000-fold higher than the concentration interpolated for the same signal level obtained for G-6-42-42 and G-6-42-71 mAbs, and ~40-fold higher than the one obtained for G-7-27-18 mAb.

Data shown in Table 4 indicate similarity of the results obtained for particular mAb clones in the studies using rHA proteins (17-530 aa, ΔRRRKKR (SEQ ID NO: 13), 6×His (SEQ ID NO: 14)) from mammalian and baculovirus expression system with high homology, differing in the level of glycosylation (Examples 2, 3) and oligomerization (FIG. 3). In case of four out of seven obtained mAb clones, for which reactivity with non-glycosylated, bacterial H5 HA protein (17-522 aa, ΔRRRKKR (SEQ ID NO: 13)) was shown under the applied conditions, interpolated concentration values indicate similarity of epitop presentation for G-6-42-42 and G-6-42-71 mAbs in recombinant HA proteins of different origin, as well as large or very large differences in epitope presentation for G-7-27-18 and G-2-14-10 mAbs, respectively, in the antigens produced in prokaryotic and eukaryotic expression system.

Reactivity with Recombinant H5 HA Proteins

Before performing reactivity studies of the obtained mAbs with recombinant H5 HA proteins, analysis of serially diluted antibodies on Ni-NTA plates coated with rHA-A/H5N1/Vietnam from mammalian expression system (ITC) (List B) was conducted. The assay was performed under conditions described in Example 4. Table 5, below, shows concentrations of mAbs from linear range of titration curves, resulting in $A_{450}$~2.5.

In particular, Table 5 shows concentrations of mAbs: G-1-31-22, G-2-14-10, G-5-32-5, G-6-42-42, G-6-42-71, G-7-24-17, G-7-27-18 from linear range of titration curves against rHA-A/H5N1/Vietnam, for which signal level ($A_{450}$) was ~2.5. The protein (18-530 aa, ΔRRRKKR (SEQ ID NO: 13), 6×His (SEQ ID NO: 14)) with HA sequence derived from A/Vietnam/1203/2004 (H5N1) was produced in (*) mammalian expression system (ITC). The assay was performed by ELISA on Ni-NTA plates (Qiagen) coated with 1 μg/mL antigen.

TABLE 5

| mAb clones | mAb concentration for $A_{450}$ ~2.5 [ng/mL] rHA* A/H5N1/Vietnam |
|---|---|
| G-1-31-22 | 50.0 |
| G-2-14-10 | 22.5 |
| G-5-32-5 | 20.0 |
| G-6-42-42 | 8.75 |
| G-6-42-71 | 12.5 |
| G-7-24-17 | 50.0 |
| G-7-27-18 | 12.5 |

*mammalian expression system

For immunoreactivity studies, Ni-NTA plates (Qiagen) were coated with H5 HA proteins: rHA and rHA1 from mammalian (ITC) and rHA protein from baculovirus (OET, series 8) expression system. Antigens were diluted to 1 μg/mL in 1% BSA/PBS. Some wells of the plate were filled in with 1% BSA/PBS and incubated overnight at 2-8° C., in parallel to the antigen-containing wells. Tested mAb clones were diluted in 2% BSA/PBS to concentrations given in Table 5, and then loaded into coated and non-coated wells of the plate. Assay was carried out in the presence of control samples. Positive control was commercial anti-H5 HA antibodies (mAb 8, List A), whereas negative control was 2% BSA/PBS (BLK sample). Plates with the tested and control samples were incubated overnight at 2-8° C. HRP-labelled anti-mouse IgG antibodies (γ-chain specific, Sigma-Aldrich) were used for the detection of antigen-bound mAbs. Secondary antibodies were diluted 1:1000 in 2% BSA/PBS and incubated on the plates for 1 h at 37° C. TMB (Sigma-Aldrich) was used as a substrate for HRP. Reaction was inhibited using 1.25 M solution of $H_2SO_4$. Absorption of samples was read at $\lambda$=450 nm.

Figure 11:
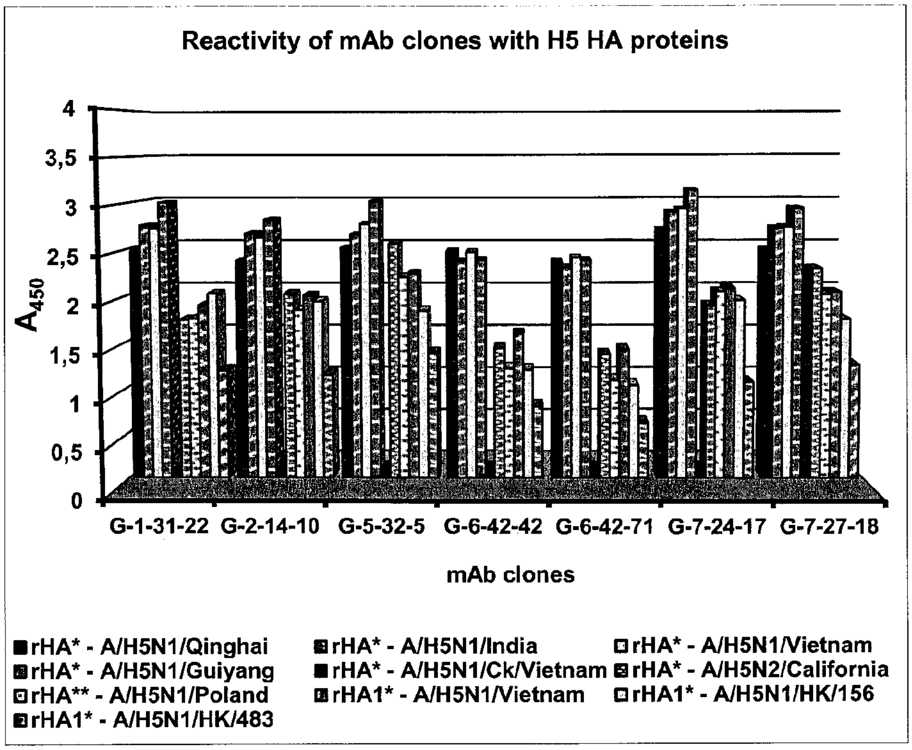
FIG. 11 shows the results of the reactivity tests for mAbs: G-1-31-22, G-2-14-10, G-5-32-5, G-6-42-42, G-6-42-71, G-7-24-17 and G-7-27-18 against proteins based on the H5 HA sequences of various IVs. The assay was performed by ELISA using recombinant antigens based on the ectodomain (rHA) and HA1 subdomain (rHA1) of hemagglutinin (List B) in 1 μg/mL concentration for coating Ni-NTA plates (Qiagen). rHA-A/H5N1/Poland protein was produced in (**) baculovirus expression system (OET, series 8). The remaining rHA and rHA1 proteins were obtained from (*) mammalian expression system (ITC). Purified antibodies were tested in concentrations from linear range of titration curves for rHA-A/H5N1/Vietnam, for which the level of ($A_{450}$) signal was ~2.5. The results are shown as $A_{450}$ values.

The results of reactivity studies for mAbs: G-1-31-22, G-2-14-10, G-5-32-5, G-6-42-42, G-6-42-71, G-7-24-17 and G-7-27-18 with recombinant proteins based on the ectodomain (rHA) and HA1 subunit (rHA1) of hemagglutinin, are shown in FIG. 11. Obtained mAb clones recognized all conformational HA antigens: rHA (5/5) and rHA1 (3/3) from mammalian expression system, rHA-A/H5N1/Poland from baculovirus expression system. None of the obtained mAb clones was binding to rHA-A/H5N1/Ck/Vietnam, which showed no characteristics of native HA. The results obtained for the purified antibodies are in line with the results of the tests for presence of serotype-specific antibodies in supernatants from cultures of cloned hybridomas, which are shown in Table 3 and described in Example 5. Immunoreactivity studies proved, that mAbs: G-1-31-22, G-2-14-10, G-5-32-5, G-6-42-42, G-6-42-71, G-7-24-17 and G-7-27-18 recognize conformational H5 HA epitopes and are directed against HA1 subunit of the antigen. In contrast to some of the commercially available anti-H5 HA antibodies (FIG. 6), described in the List A, all of the obtained mAbs showed reactivity with H5 HA of antigenically distant IV strains.

Figure 12:
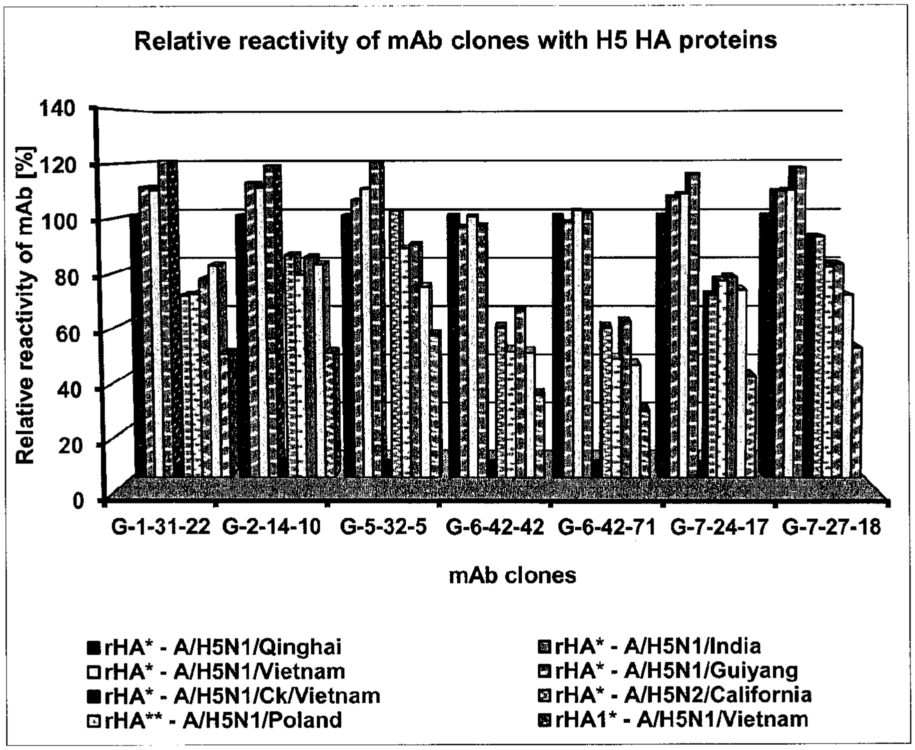
FIG. 12 shows the level of reactivity of mAbs: G-1-31-22, G-2-14-10, G-5-32-5, G-6-42-42, G-6-42-71, G-7-24-17 and G-7-27-18 against proteins based on the H5 HA sequences of various IVs relative to the reactivity against immunogen. The assay was performed by ELISA using recombinant antigens based on the ectodomain (rHA) and HA1 subdomain (rHA1) of hemagglutinin (List B) in 1 μg/mL concentration for coating Ni-NTA plates (Qiagen). rHA-A/H5N1/Poland protein was produced in (**) baculovirus expression system (OET, series 8). The remaining rHA and rHA1 proteins were obtained from (*) mammalian expression system (ITC). Purified antibodies were tested in concentrations from linear range of titration curves for rHA-A/H5N1/Vietnam, for which the level of ($A_{450}$) signal was ~2.5. ($A_{450}$) signal values obtained in the reactivity tests of produced antibodies against recombinant H5 HA proteins are shown as % of $A_{450}$ values read in the tests, in which rHA-A/H5N1/Qinghai was used (relative reactivity against recombinant H5 HA proteins).

To provide better data comparability, signal values ($A_{450}$) obtained in the studies of reactivity of generated antibodies with recombinant H5 HA proteins having sequences from different viral strains, were expressed as % of $A_{450}$ values read in the tests, in which the immunogen (rHA-A/H5N1/Qinghai) was used. The results thus obtained, further described as relative reactivity of the obtained antibodies with recombinant HA proteins, is shown in FIG. 12. Obtained mAb clones retained high reactivity, shown with rHA-A/H5N1/Qinghai, with rHA (17/18-530 aa, ΔRRRKKR (SEQ ID NO: 13), 6×His (SEQ ID NO: 14)) from mammalian expression system having HA sequences of A/H5N1/India, A/H5N1/Vietnam and A/H5N1/Guiyang influenza viruses—relative reactivities with individual antigens were 96-113%, 100-111% and 96-121%, respectively. Identity of amino acids from HA1 subunit of the above-mentioned antigens to HA1 subunit of the immunogen was from 99% to 93% (List F).

For most of the obtained clones (5/7), decrease in relative reactivities with rHA-A/H5N2/California (19-506 aa, 6×His (SEQ ID NO: 14)) from mammalian expression system was found, to values in a range of 58-85%. HA1 subunit of this antigen contained 88% of amino acids identical to the sequence of HA1 subunit of the immunogen (List F). Reduced relative reactivities were also observed in the studies using rHA-A/H5N1/Poland (17-530 aa, ΔRRRKKR (SEQ ID NO: 13), 6×His (SEQ ID NO: 14)) from baculovirus expression system, with high homology to the immunogen (99% of sequence identity for HA1 subunit, List F). This was the case for all of the obtained mAbs (7/7), and relative reactivities were from 46% to 87%.

In the tests using HA1 subunit-based proteins from mammalian expression system: rHA1-A/H5N1/Vietnam (1-345 aa, 6×His (SEQ ID NO: 14)), rHA1-A/H5N1/HK/156 (18-346 aa, 6×His (SEQ ID NO: 14)) and rHA1-A/H5N1/HK/483 (17-346 aa, 6×His (SEQ ID NO: 14)), lower reactivity was found in comparison to the reactivity with rHA proteins from mammalian expression system, which were based on the HA sequences from A/H5N1/Qinghai, A/H5N1/India, A/H5N1/Vietnam and A/H5N1/Guiyang influenza viruses. Relative reactivities with individual rHA1 antigens were 60-89%, 43-81% and 26-55%, respectively. The differences in relative reactivities of the obtained antibody clones with rHA-A/H5N1/Vietnam and rHA1-A/H5N1/Vietnam, were from 21% to 42%. This is in line with previous observations, that sensitivity of detection of anti-HA1 subunit antibodies is lower when rHA1 proteins, and not rHA proteins are used for coating of Ni-NTA plates (Examples 4, 5). Identity of amino acids in rHA1 proteins with sequences of HA of A/H5N1/Vietnam, A/H5N1/HK/156, A/H5N1/HK/483 influenza viruses to the sequence of HA1 subunit of the immunogen, was 95%, 95% and 94%, respectively (List F).

Reduced relative reactivity with rHA-A/H5N2/California antigen with relatively high oligomerization (FIG. 3), which was observed for most of the obtained mAbs (5/7), could result from lower homology of the protein to the immunogen (88% vs 99%-93% of HA1 subunit sequence identity, List F), but also from the difference in antigen presentation associated with the length of protein fragment (19-506 aa vs 17/18-530 aa). Significantly lower reactivity of all obtained mAbs with rHA-A/H5N1/Poland from baculovirus expression system than with rHA-A/H5N1/Qinghai of similar sequence, as well as with other rHA proteins of the same length (17/18-530 aa) from mammalian expression system, showed in the studies using Ni-NTA plates, resulted probably from relatively low protein oligomerization, which could influence coating efficiency and/or presentation of the antigen bound to the plate by 6×His tag. The argument behind this interpretation are the results of works on the optimization of ELISA for determining specificity of obtained mAbs (Example 3) and tests for specificity of the obtained mAb clones against rHA-A/H5N1/Poland and rHA-A/H5N1/Qinghai, which were performed using MediSorp plates and described in the first part on present Example. Those studies showed no significant differences in the reactivity level of individual mAb clones with antigens from mammalian and baculovirus expression system, despite the differences in the level of glycosylation (Examples 2, 3) and oligomerization (FIG. 3). As in case of rHA-A/H5N1/Poland from baculovirus expression system, very low oligomerization or its absence influencing antigen coating and presentation, was probable cause of reduced relative reactivities of the obtained mAbs with rHA1 proteins bound on Ni-NTA plate. Analysis of the obtained results leads to the conclusion that observed variation in relative reactivities of the obtained mAbs with recombinant H5 HA antigens results from different properties of proteins used in tests rather than from the variation of sequences of HA1 subunit of those proteins.

Reactivity with H1-H16 Serotype Influenza Viruses

The tests for the ability of mAbs: G-1-31-22, G-2-14-10, G-5-32-5, G-6-42-42, G-6-42-71, G-7-24-17 and G-7-27-18 to recognize HA in viral particles were performed by ELISA using twenty five AIV strains, representing H1-H16 serotypes (List C). The assay was performed under conditions described in Example 4. Table 6, below, shows the results of reactivity analysis for the obtained clones of mAbs.

In particular, Table 6 shows the results of the reactivity tests for mAbs: G-1-31-22, G-2-14-10, G-5-32-5, G-6-42-42, G-6-42-71, G-7-24-17 and G-7-27-18 against LPAIV of the H1, H2, H3, H4, H5, H6, H7, H8, H9, H10, H11, H12, H13, H14, H15 and H16 serotypes (List C). The assay was performed by ELISA by coating MaxiSorp plates (NUNC) with viruses diluted do 4000 HAU/mL based on the value specified by the manufacturer. Influenza viruses (x-OvO) were derived from IZSVe. Purified antibodies were tested in 20 μg/mL concentration.

TABLE 6

| HA serotype | Avian influenza virus (AIV) | mAb clones G-1-31-22 | G-2-14-10 | G-5-32-5 | G-6-42-42 | G-6-42-71 | G-7-24-17 | G-7-27-18 |
|---|---|---|---|---|---|---|---|---|
| H1 | A/duck/It/1447/05(H1N1) | – | – | – | – | – | – | – |
| H2 | A/duck/Germ/1215/73(H2N3) | – | – | – | – | – | – | – |
| H3 | A/pass/It/6000/V00(H3N8) | – | – | – | – | – | – | – |
| | A/psitt/It/2873/00(H3N8) | – | – | – | – | – | – | – |
| H4 | A/cockatoo/Eng/72(H4N8) | – | – | – | – | – | – | – |
| H5 | A/mallard/It/3401/05(H5N1) | + | + | + | + | + | + | + |
| | A/turk/It/80(H5N2) | + | + | + | + | + | + | + |
| | A/duck/It/775/04(H5N3) | + | + | + | + | + | + | + |
| | A/ck/It/22A/98(H5N9) | + | + | + | + | + | + | + |
| H6 | A/turkey/Canada/65 (H6N2) | – | – | – | – | – | – | – |
| H7 | A/ck/It/1067/V99(H7N1) | – | – | – | – | – | – | – |
| | A/ty/It/9289/V02(H7N3) | – | – | – | – | – | – | – |
| | A/mallard/It/4810-79/04(H7N4) | – | – | – | – | – | – | – |
| | A/macaw/626/80(H7N7) | – | – | – | – | – | – | – |
| H8 | A/turk/Ont/6118/68(H8N4) | – | – | – | – | – | – | – |
| H9 | A/ty/Wis/66(H9N2) | – | – | – | – | – | – | – |
| | A/turk/Scotland/1/70(H9N7) | – | – | – | – | – | – | – |
| H10 | A/ostrich/SA/01(H10N1) | – | – | – | – | – | – | – |
| H11 | A/duck/Eng/56(H11N6) | – | – | – | – | – | – | – |
| | A/duck/Memphis/546/174(H11N9) | – | – | – | – | – | – | – |
| H12 | A/duck/Alberta/60/76(H12N5) | – | – | – | – | – | – | – |
| H13 | A/gull/Maryland/704/77(H13N6) | – | – | – | – | – | – | – |
| H14 | A/mallard/Gurjev/263/82(H14N5) | – | – | – | – | – | – | – |
| H15 | A/shearwater/2576/79(H15N9) | – | – | – | – | – | – | – |
| H16 | A/gull/Denmark/68110/02(H16N3) | – | – | – | – | – | – | – |

All obtained mAb clones, i.e. G-1-31-22, G-2-14-10, G-5-32-5, G-6-42-42, G-6-42-71, G-7-24-17 and G-7-27-18, recognized HA of H5N1, H5N2, H5N3 and H5N9 AIVs. The results obtained for the purified antibodies are in line with the results of the tests for the presence of antibodies specific against AIV of H5 serotype in supernatants from cultures of cloned hybridomas, which are shown in Table 3 and described in Example 5. Tests with the use of AIVs of H1-H4 and H6-H16 serotypes showed, that generated antibodies do not cross-react with HA of serotypes other than H5.

Figure 13:
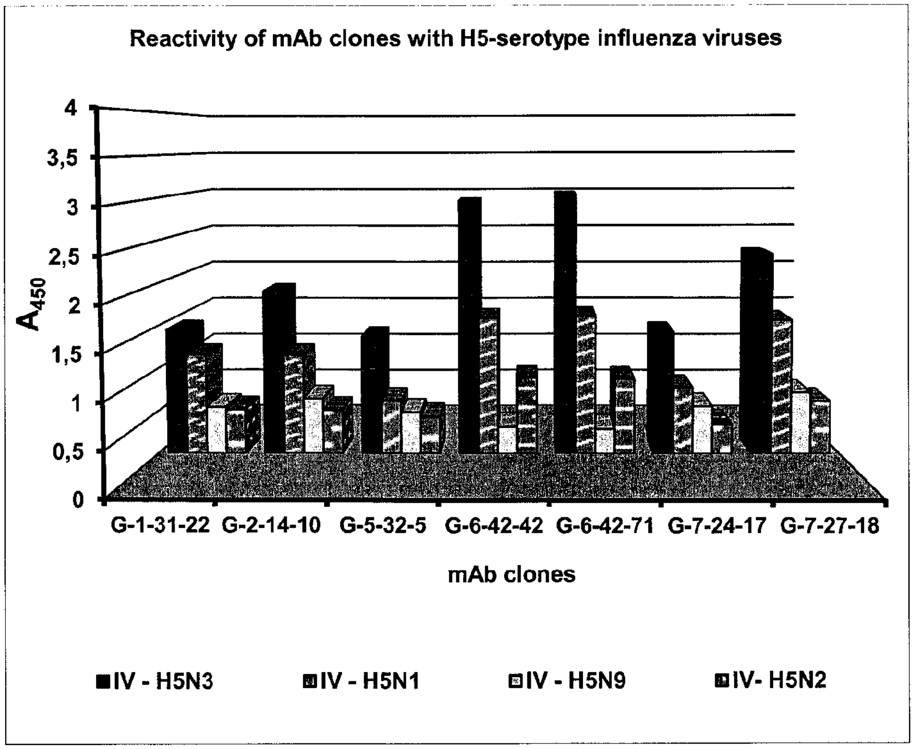
FIG. 13 shows the results of the reactivity tests for mAbs: G-1-31-22, G-2-14-10, G-5-32-5, G-6-42-42, G-6-42-71, G-7-24-17 and G-7-27-18 against LPAIV of the H5 serotype. The assay was performed by ELISA by coating MaxiSorp plates (NUNC) with H5N3, H5N1, H5N9 and H5N2 viruses diluted do 4000 HAU/mL based on the value specified by the manufacturer. Influenza viruses (x-OvO) were derived from IZSVe. Purified antibodies were tested in 20 μg/mL concentration. The results are shown as $A_{450}$ values.

FIG. 13 shows test results for the reactivity of mAbs: G-1-31-22, G-2-14-10, G-5-32-5, G-6-42-42, G-6-42-71, G-7-24-17 and G-7-27-18 with H5N3, H5N1, H5N9 and H5N2 AIVs. Reactivity of all obtained antibody clones was the highest against H5N3 AIV. In the tests using this virus, signal ($A_{450}$) values were in the range of 1.4-3.0. According to the results of H5 HA antigen sequences analysis against immunogen source sequence (rHA-A/H5N1/Qinghai), which are shown in Lists E and F, both full-length protein and HA1 subunit of HA of H5N3 virus showed the highest homology factors (Max Score, Total Score, Identities) among hemagglutinins of AIV strains used in the studies of immunoreactivity of the obtained mAbs.

Figure 14:
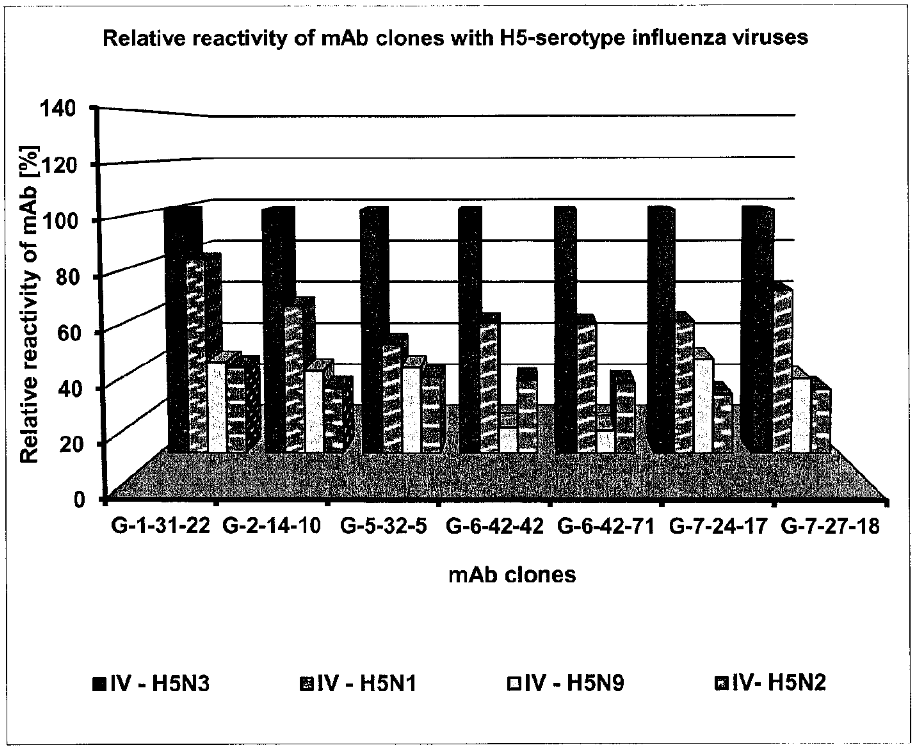
FIG. 14 shows the level of reactivity of mAbs: G-1-31-22, G-2-14-10, G-5-32-5, G-6-42-42, G-6-42-71, G-7-2417 and G-7-27-18 against H5N1, H5N9 and H5N2 LPAIVs relative to the reactivity against H5N3 AIV. The assay was performed by ELISA by coating MaxiSorp plates (NUNC) with H5N3, H5N1, H5N9 and H5N2 viruses diluted do 4000 HAU/mL based on the value specified by the manufacturer. Influenza viruses (x-OvO) were derived from IZSVe. Purified antibodies were tested in 20 μg/mL concentration. ($A_{450}$) signal values obtained in the reactivity tests of produced antibodies against H5N1, H5N9 and H5N2 AIVs are shown as % of $A_{450}$ values read in the tests, in which H5N3 AIV was used (relative reactivity against AIV of H5 serotype).

To provide better data comparability, signal values ($A_{450}$) obtained in the studies of reactivity of generated antibodies against H5N1, H5N9 and H5N2 viruses, were expressed as % of $A_{450}$ values read in the tests, in which H5N3 AIVs were used. The results thus obtained, further described as relative reactivity of the obtained antibodies against AIVs of H5 serotype, is shown in FIG. 14. Reactivity of mAbs: G-1-31-22, G-2-14-10, G-5-32-5, G-6-42-42, G-6-42-71, G-7-24-17 and G-7-27-18 with H5N1 AIV was 45-80% of the reactivity determined with H5N3 virus. Comparing to the hemagglutinin of H5N3 AIV, HA1 subunit of HA of H5N1 virus is characterized by the same sequence identity determined to the immunogen (93%) and lower homology factors: Max Score and Total Score (List F). Further lowering of reactivity of the obtained mAbs was observed in assays using H5N9 AIV and H5N2 AIV. Relative reactivities of antibodies with those viruses were in range 10-39% and 24-35%, respectively. According to the data in the List F, HA1 subunit of H5N9 and H5N2 viruses contains 90% of amino acids identical to the sequence of HA1 subunit of the immunogen, and homology factors, Max Score and Total Score, are higher in case of antigen of H5N9 virus than H5N2 virus.

Analysis of the results leads to the conclusion, that observed variation of reactivities of particular mAb clones with H5N1, H5N2, H5N3 and H5N9 AIVs may be associated with variation of sequences forming HA1 subunit of HA viruses used in the tests and/or with the effectiveness of coating ELISA plates with viral antigens. Information regarding differences in the composition of viral preparations, which could influence conditions of assays for the immunoreactivity of antibodies, is included in the description of ELISA method with the use of influenza viruses (Example 4).

Summary

Further studies of mAbs: G-1-31-22, G-2-14-10, G-5-32-5, G-6-42-42, G-6-42-71, G-7-24-17 and G-7-27-18, after their purification from hybridoma culture supernatants, were performed using H5 HA antigens of varied properties. Among the antigens, there were HA ectodomain-based recombinant proteins (rHA) from mammalian, baculovirus and bacterial expression systems, proteins based on the HA1 subunit (rHA1), obtained in mammalian cells, as well as twenty five AIV strains of H1-H16 serotypes (Lists B, C).

The vast majority of H5 HA antigens (13/14) showed characteristics of native hemagglutinin (FIG. 2, 5, 6).

Obtained mAb clones recognized all conformational, glycosylated H5 HA antigens: rHA (6/6) and rHA1 (3/3) from eukaryotic expression system (FIG. 11), as well as AIVs of H5 serotype (4/4) (FIG. 13) with varied homology to rHA-A/H5N1/Qinghai immunogen (99% to 88% of sequence identity for HA1 subunit, List F). Under the testing conditions, for some clones (4/7) significant reactivity towards non-glycosylated bacterial H5 HA protein was also shown. None of the obtained mAb clones was binding to non-conformational rHA-A/H5N1/Ck/Vietnam protein (FIG. 11) nor to AIVs of H1-H4 and H6-H16 serotypes (Table 6).

The obtained results lead to the conclusion, that mAbs: G-1-31-22, G-2-14-10, G-5-32-5, G-6-42-42, G-6-42-71, G-7-24-17 and G-7-27-18 are directed against conformational epitopes of Hemagglutinin HA1 subunit, show broad range of specificities to the HA of H5 serotype and at the same time, do not cross-react with the HA of H1-H4 and H6-H16 serotypes.

Example 8 Clones Differentiation Based on Immunoreactivity Profiles

Figure 15:
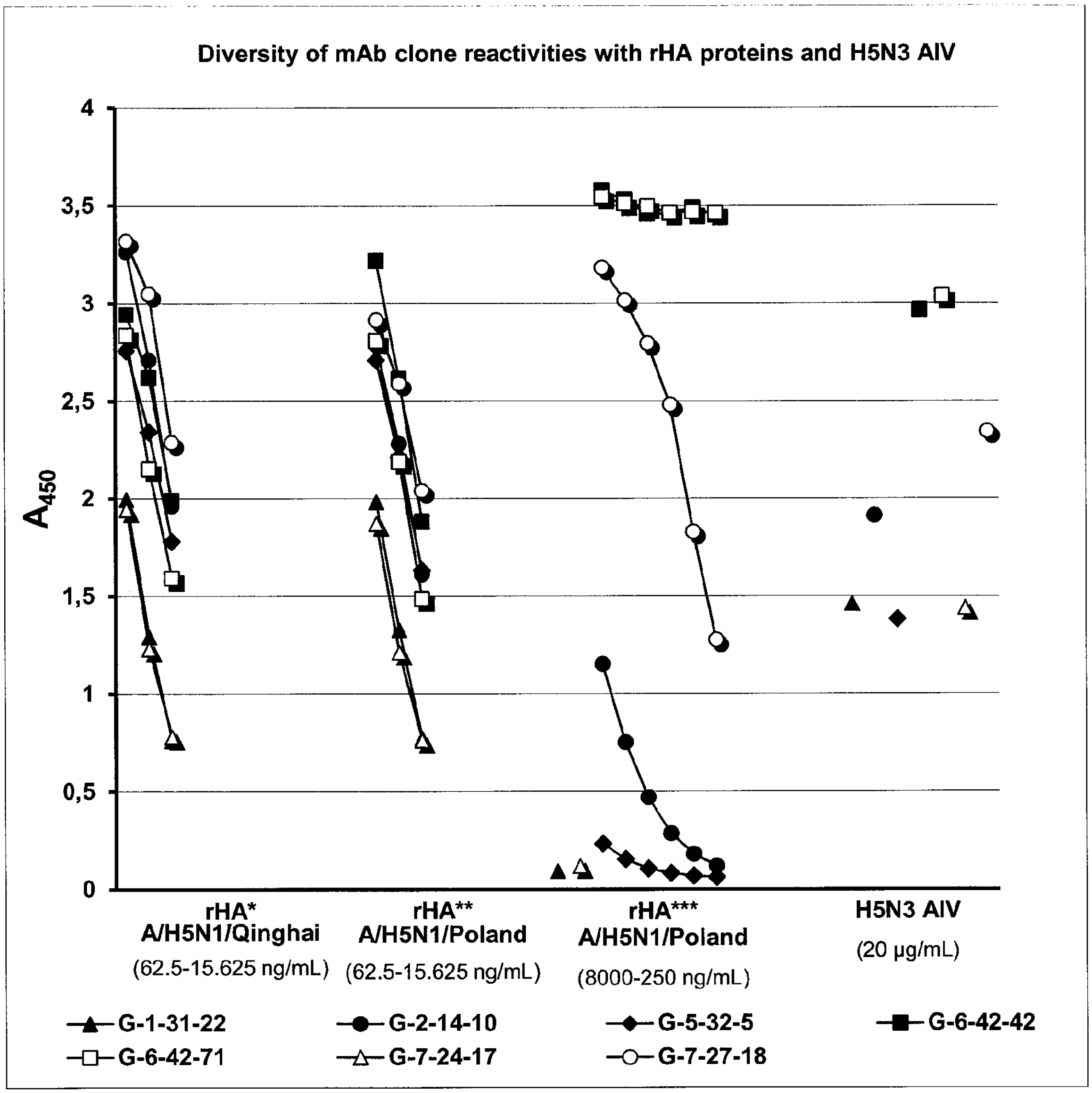
FIG. 15 shows reactivity profiles for mAbs: G-1-31-22, G-2-14-10, G-5-32-5, G-6-42-42, G-6-42-71, G-7-24-17 and G-7-27-18 against recombinant HA proteins and avian influenza virus with the highest homology to the immunogen among used rHA proteins and AIV of H5 serotype, respectively. Antigen: 17-530 aa (ΔRRRKKR (SEQ ID NO: 13), 6×His (SEQ ID NO: 14)) with HA sequence derived from A/Bar-headed Goose/Qinghai/12/05 (H5N1) strain of AIV was produced in (*) mammalian expression system (ITC). HA proteins: 17-530 aa (ΔRRRKKR (SEQ ID NO: 13), 6×His (SEQ ID NO: 14)) and 17-522 aa (ΔRRRKKR (SEQ ID NO: 13)) were produced in () baculovirus (OET, series 8) and (*) bacterial expression system (IBA), respectively, based on the HA sequence derived from A/swan/Poland/305-135V08/2006 (H5N1) strain of AIV. H5N3 influenza virus (x-OvO) was derived from IZSVe. MediSorp (rHA*, rHA), PolySorp, MediSorp, MaxiSorp and MultiSorp (rHA*) plates (NUNC) were used for coating with rHA proteins (1 μg/mL), whereas MaxiSorp plates (NUNC) were used for coating with H5N3 virus (4000 HAU/mL). The results are shown as ($A_{450}$ signal values obtained using generated mAbs in 62.5-15.625 ng/mL (rHA*, rHA), 8000-250 ng/mL (rHA*) and 20 μg/mL (AIV H5N3) concentrations.
Figure 16:
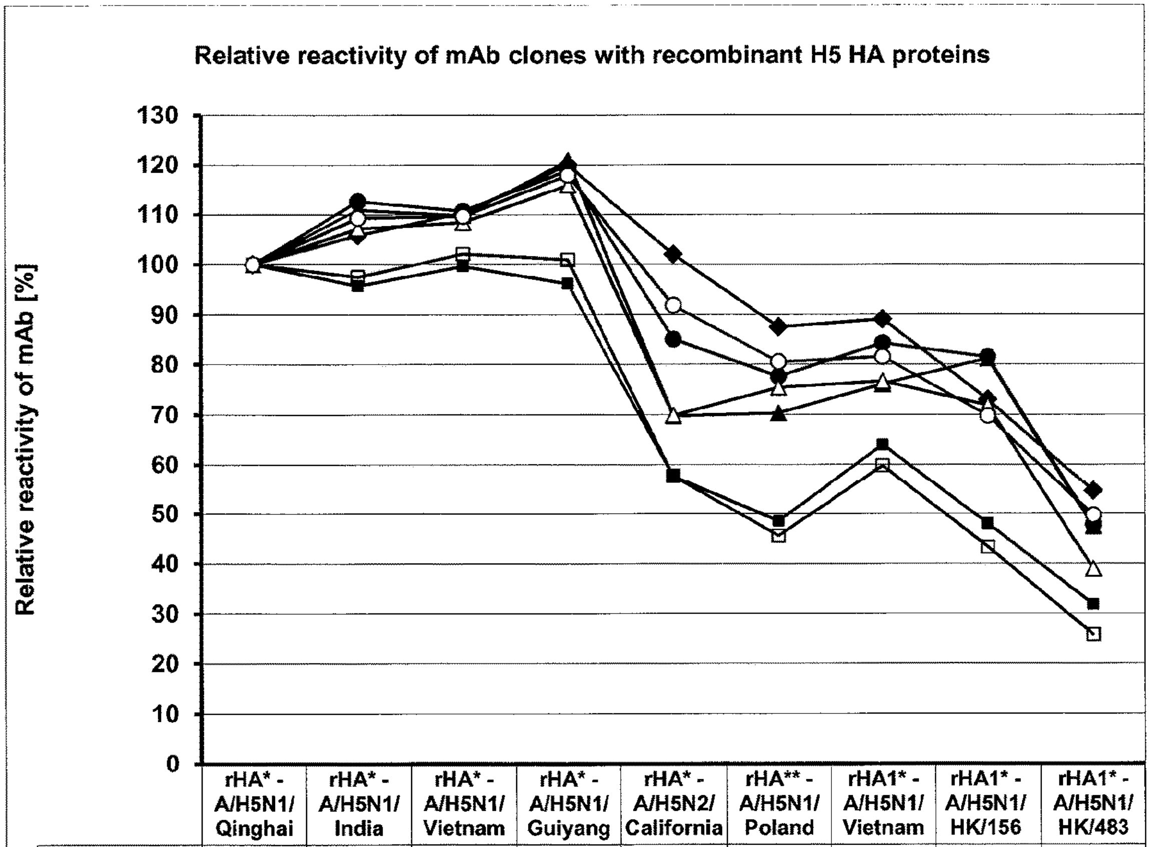
FIG. 16 shows profiles of relative reactivities for mAbs: G-1-31-22, G-2-14-10, G-5-32-5, G-6-42-42, G-6-42-71, G-7-24-17 and G-7-27-18 against proteins with H5 HA sequences from various IV strains. The assay was performed by ELISA using recombinant antigens based on the ectodomain (rHA) and HA1 subdomain (rHA1) of hemagglutinin (List B) in 1 μg/mL concentration for coating Ni-NTA plates (Qiagen). rHA-A/H5N1/Poland protein was produced in (**) baculovirus expression system (OET, series 8). The remaining rHA and rHA1 proteins were obtained from (*) mammalian expression system (ITC). Purified antibodies were tested in concentrations from the linear range of titration curves for rHA-A/H5N1/Vietnam, for which the level of ($A_{450}$) signal was ~2.5. Relative reactivity of the obtained mAbs against recombinant H5 HA proteins is the level of reactivity expressed as % of $A_{450}$ values read in the tests, in which rHA*-A/H5N1/Qinghai was used.
Figure 17:
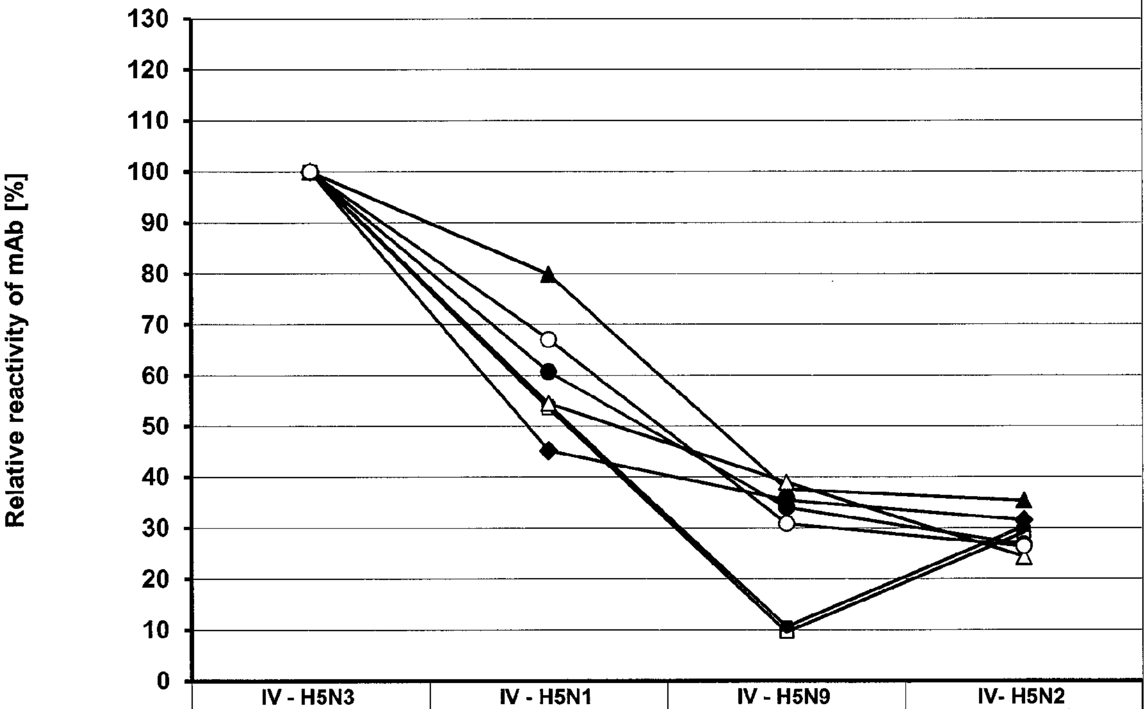
FIG. 17 shows profiles of relative reactivities for mAbs: G-1-31-22, G-2-14-10, G-5-32-5, G-6-42-42, G-6-42-71, G-7-24-17 and G-7-27-18 against H5N1, H5N9 and H5N2 AIVs. The assay was performed by ELISA by coating MaxiSorp plates (NUNC) with H5N3, H5N1, H5N9 and H5N2 viruses diluted do 4000 HAU/mL. Influenza viruses of H5 serotype (x-OvO) were derived from IZSVe. Purified antibodies were tested in 20 μg/mL concentration. Relative reactivity of the obtained mAbs against AIVs of H5 serotype is the level of reactivity expressed as % of $A_{450}$ values read in the tests, in which H5N3 AIV was used.

Based on the results of the reactivity tests for mAbs: G-1-31-22, G-2-14-10, G-5-32-5, G-6-42-42, G-6-42-71, G-7-24-17 and G-7-27-18 with H5 HA antigens (Example 7), reactivity profiles were created for use in comparative analysis of the obtained clones. FIG. 15 shows reactivity profiles for antibodies with rHA-A/H5N1/Qinghai from mammalian expression system, rHA-A/H5N1/Poland from baculovirus expression system and rHA-A/H5N1/Poland from bacterial expression system, as well as with H5N3 AIV of the highest homology to the immunogen among recombinant HA proteins and AIV of H5 serotype used in the tests, respectively. FIG. 16 shows relative reactivities profiles of the obtained clones with recombinant proteins of H5 HA sequences of different IV strains, whereas FIG. 17 shows profiles with H5N1, H5N9 and H5N2 AIVs. The term "relative reactivity" was introduced and described in Example 7. In case of recombinant antigens, this term means the level of reactivity relative to the reactivity with the immunogen (rHA-A/H5N1/Qinghai), and in case of AIVs-relative to the reactivity with H5N3 virus. Relative reactivity with recombinant H5 HA proteins and AIVs of H5 serotype are expressed as % of $A_{450}$ value determined in tests using rHA-A/H5N1/Qinghai and H5N3 AIV, respectively. Information regarding antigens used in the immunoreactivity assays are shown in Lists B and C. Recombinant H5 HA proteins are described in detail in Examples 2, 3, 4, 7. Test methods are described in Example 7.

G-6-42-42 and G-6-42-71 antibodies differ clearly from the other obtained clones by characteristic reactivity profiles (FIG. 15, 16, 17). In the test using MediSorp plates (FIG. 15), those antibodies showed high affinity for rHA-A/H5N1/Qinghai from mammalian expression system and rHA-A/H5N1/Poland from baculovirus expression system. In comparison to the other five clones, G-6-42-42 and G-6-42-71 mAbs are characterized by: the highest reactivities with rHA-A/H5N1/Poland produced in *E. coli*, and also with H5N3 virus (FIG. 15), equalized (at ~100% level) relative reactivities with rHA-A/H5N1/India, rHA-A/H5N1/Vietnam and rHA-A/H5N1/Guiyang, and the lowest relative reactivities with other rHA and rHA1 proteins (FIG. 16). According to the results shown in FIG. 17, G-6-42-42 and G-6-42-71 antibodies differ also by significantly lower relative reactivities with H5N9 AIV than with H5N2 virus (11%, 10% vs 30%, 29%). Similarity of all immunoreactivity profiles for G-6-42-42 and G-6-42-71 (FIG. 15, 16, 17) indicate, that those antibodies, derived from cloning the same primary hybridoma, designated as G-6-42 (Table 3), represent one clone. Additionally, mass spectra of both G-6-42-42 and G-6-42-71 antibodies showed the presence of two protein forms (FIG. 7*d, e*), which was not found for the other clones (FIG. 7*a, b, c, f, g*).

An important criterion differentiating remaining obtained mAbs: G-1-31-22, G-2-14-10, G-5-32-5, G-7-24-17 and G-7-27-18 are the levels of signals ($A_{450}$) for particular antibody concentrations, treated as an indicative measure of the affinity for antigens and shown in FIG. 15. Relative reactivity profiles of G-1-31-22, G-2-14-10, G-5-32-5, G-7-24-17 and G-7-27-18 antibodies with recombinant H5 HA proteins and AIVs of H5 serotype, shown in FIGS. 16 and 17, show significant similarity, but also differences, which became the basis r differentiation of those clones. The key discriminatory antigens were rHA-A/H5N2/California (FIG. 16) and H5N1 AIV (FIG. 17).

G-1-31-22 and G-7-24-17 antibodies differ from G-2-14-10, G-5-32-5 and G-7-27-18 antibodies, inter alia, because they show lower binding affinity with rHA-A/H5N1/Qinghai from mammalian expression system and rHA-A/H5N1/Poland from baculovirus expression system adsorbed on MediSorp plates (FIG. 15), as well as with Ni-NTA plate-bound rHA-A/H5N1/Vietnam (Table 5). Contrary to other obtained clones, no reactivity with bacterial rHA-A/H5N1/Poland under testing conditions was shown for G-1-31-22 and G-7-24-17 antibodies, and their reactivity with H5N3 AIV was the lowest and comparable only to the reactivity of G-5-32-5 mAb with this virus (FIG. 15). The results shown in FIG. 16 showed significantly lower level of relative reactivity for G-1-31-22 and G-7-24-17 clones with rHA-A/H5N2/California than G-2-14-10, G-5-32-5 and G-7-27-18 clones (70% vs 85-102%). While reactivity profiles of G-1-31-22 and G-7-24-17 clones, shown in FIGS. 15 and 16, are similar, relative reactivity profiles of those antibodies with AIV of H5 serotype, shown in FIG. 17, indicate, that G-1-31-22 and G-7-24-17 antibodies are different clones. G-1-31-22 mAbs showed significantly higher relative reactivity with H5N1 AIV than G-7-24-17 mAbs (80% vs 54%) and the other clones of the obtained antibodies (80% vs 45-67%).

The immunoreactivity profiles, shown in FIGS. 15, 16 and 17, show, that G-5-32-5 antibodies have features differentiating them from both G-1-31-22 and G-7-24-17, as well as from G-2-14-10 and G-7-27-18 antibodies. G-5-32-5 mAb is characterised by high binding affinity for rHA-A/H5N1/Qinghai from mammalian expression system and rHA-A/H5N1/Poland from bculovirus expression system adsorbed on MediSorp plates, and at the same time, by very weak reactivity with bacterial HA protein and one of the lowest reactivities with H5N3 AIV (FIG. 15). This clone is distinguished from the other antibodies by the highest level of relative reactivity with rHA-A/H5N2/California, rHA1-A/H5N1/Vietnam and rHA1-A/H5N1/HK/483 from mammalian expression system and rHA-A/H5N1/Poland from baculovirus expression system, bound to Ni-NTA plates (FIG. 16), as well as by the lowest level of relative reactivity with H5N1 AIV (FIG. 17). The results suggest, that G-5-32-5 mAbs recognize glycosylated HA proteins produced in eukaryotic expression system with higher affinity than HA in viral particles.

G-2-14-10 and G-7-27-18 clones were in a group of antibodies with high binding affinity for rHA-A/H5N1/Qinghai from mammalian expression system and rHA-A/

H5N1/Poland from baculovirus expression system adsorbed on MediSorp plates (FIG. 15). Comparing to G-1-31-22, G-7-24-17 and G-5-32-5 clones, G-2-14-10 and G-7-27-18 antibodies showed significant reactivity with rHA-A/H5N1/Poland produced in bacterial expression system, and higher reactivity with H5N3 AIV (FIG. 15). Reactivity of G-7-27-18 mAb with both bacterial H5 HA, and with H5N1 AIV was higher than of G-2-14-10 mAb, which suggests, that those antibodies are different clones (FIG. 15). Beside the differences shown in FIG. 15, G-2-14-10 and G-7-27-18 antibodies are characterized by significant similarity to relative reactivity profiles with recombinant HA proteins H5N1, H5N9 and H5N2 viruses (FIG. 16, 17). In terms of relative reactivities, G-2-14-10 and G-7-27-18 clones are differentiated from G-1-31-22, G-7-24-17, G-5-32-5 antibodies primarily by the results obtained in tests using rHA-A/H5N2/California and H5N1 AIV (FIG. 16, 17). The relative reactivity levels of G-2-14-10 and G-7-27-18 mAbs with rHA-A/H5N2/California were lower than of G-5-32-5 mAb and higher than G-1-31-22 and G-7-24-17 mAbs, whereas with H5N1 virus they were lower than G-1-31-22 mAb and higher than G-7-24-17 and G-5-32-5 mAb.

Summary

As a result of applying procedure of mAb generation by hybridoma method (Example 1), 7 antibody clones, denoted G-1-31-22, G-2-14-10, G-5-32-5, G-6-42-42, G-6-42-71, G-7-24-17 and G-7-27-18, were obtained. Analysis of immunoreactivity profiles revealed, that G-1-31-22, G-2-14-10, G-5-32-5, G-7-24-17 and G-7-27-18 mAbs are different clones, whereas G-6-42-42 and G-6-42-71 mAbs represent one antibody clone, different from the other five clones. Thus, six mAb clones were obtained, which recognized different epitopes specific for H5 hemagglutinin.

Example 9

Differentiation of Clones Based on the Peptide Maps of Fab Fragments

The aim of the studies described below was to obtain Fc and Fab fragments of G-1-31-22, G-2-14-10, G-5-32-5, G-6-42-42, G-6-42-71, G-7-24-17 and G-7-27-18 antibodies by ficin digestion and comparison of their peptide maps generated as a result of trypsinolysis. Based on the mass spectra recorded, peptides characteristic only for one particular or only for some of the obtained antibody clones ("discriminatory" peptides), as well as those present in all of the analysed mAbs ("common" peptides) were determined.

Purified mAbs were concentrated with the use of centrifugal concentrators "VivaSpin6", MWCO 10 000 (Sartorius Stedim Biotech) with simultaneous buffer exchange to PBS, pH 7.4. Ficin digestion of antibodies was performed using commercial "Pierce™ Mouse $IgG_1$ Fab and $F(ab')_2$ Micro Preparation Kit" (Pierce/Thermo Scientific). Sample preparation, digestion and purification were conducted strictly according to manufacturer's instructions. Maximally concentrated protein, i.e. 250 μg in 125 μL solution, was loaded into the ficin-containing column. The digestion time was 5 h. After separation by affinity chromatography, fractions containing Fab and Fc fragments, as well as undigested antibodies, were concentrated using "VivaSpin 6" centrifugal concentrators, MWCO 5 000 (Sartorius Stedim Biotech) with simultaneous buffer exchange to PBS, pH 7.4.

Concentrated fractions were separated using non-reducing electrophoresis (SDS-PAGE) in 2 polyacrylamide gels system (5% stacking gel, pH 6.8 and 12.5% resolving gel, pH 8.8). The protein bands corresponding to the Fab, Fc and undigested IgG were excised from the gel, reduced using 10 mM dithiothreitol (Sigma-Aldrich), alkylated with 50 mM iodoacetamide (Sigma-Aldrich) and digested with 10 ng/mL trypsin solution (Promega). Simultaneously, digestion of the above mentioned fractions with trypsin in solution was performed. Each time, peptide-containing samples were concentrated using concentrator (Koncentrator 5301, Eppendorf) and analysed by MALDI TOF/TOF mass spectrometry.

Molecular weights and fragmentation ions of the peptides were determined using MALDI TOF/TOF mass spectrometer (4800 Plus, AB SCIEX). The matrix was alpha-cyano-4-hydroxycinnamic acid dissolved in 0.1% trifluoroacetic acid containing 50% of acetonitrile. Peptide masses were recorded in reflector-positive mode (MS Reflector Positive Ion) in the range of 900-8000 Da. External calibration was achieved with a 4700 proteomics analyzer calibration mixture (AB SCIEX). Masses of molecules, included into calculations and shown in the description, are monoisotopic masses of ionized single molecule with hydrogen atom attached. Peptides were identified based on the obtained peptide maps and fragmentation spectra using databases available in Mascot system. Theoretical masses of peptides, whose sequence was confirmed using Mascot system, were calculated with the use of generally available internet service on ExPASy server. Peptides found in protein databases were further referred to, in the text and tables, as "identified". In tables, they are designated with "*" symbol. For a distinction, "non-identified" peptides were those not assigned to any known protein. In case of those peptides, monoisotopic masses given are means from all obtained mass spectra. Data in the tables below are specific result of both trypsinolysis method used. Symbols "+" and "−" in the tables referred to the presence and absence, respectively, of a given peptide in peptide maps of particular mAbs.

Peptide Maps of Fc Fragments

Peptide maps of Fc fragments of G-1-31-22, G-2-14-10, G-5-32-5, G-6-42-42, G-6-42-71, G-7-24-17 and G-7-27-18 mAbs and amino acid sequences of peptides identified in those maps are shown in Table 7(a, b), below.

More specifically, Table 7 shows (a) peptide maps of Fc fragments of G-1-31-22, G-2-14-10, G-5-32-5, G-6-42-42, G-6-42-71, G-7-24-17 and G-7-27-18 mAbs and (b) amino acid sequences of peptides identified in those maps. Peptide maps, obtained as a result of trypsinolysis, were analysed using MALDI TOF/TOF mass spectrometry. Peptides were identified based on the obtained peptide maps and fragmentation spectra using databases available in Mascot system.

TABLE 7a

| Peptide maps of Fc fragments of monoclonal antibodies (mAbs) | | | | | | | | | | | | | |
|---|---|---|---|---|---|---|---|---|---|---|---|---|---|
| mAb | Mass [Da] | | | | | | | | | | | | |
| clones | 1169.6* | 1243.7* | 1301.7* | 1826.9* | 2112.0* | 2753.3* | 2782.3* | 1580.9 | 1771.9 | 1854.9* | 2258.1* | 1965.8 | 2764.1 |
| G-1-31-22 | + | + | + | + | + | + | + | + | + | − | − | − | − |
| G-2-14-10 | + | + | + | + | + | + | + | + | + | − | − | − | + |

TABLE 7a-continued

Peptide maps of Fc fragments of monoclonal antibodies (mAbs)

| mAb | Mass [Da] | | | | | | | | | | | | |
|---|---|---|---|---|---|---|---|---|---|---|---|---|---|
| clones | 1169.6* | 1243.7* | 1301.7* | 1826.9* | 2112.0* | 2753.3* | 2782.3* | 1580.9 | 1771.9 | 1854.9* | 2258.1* | 1965.8 | 2764.1 |
| G-5-32-5 | + | + | + | + | + | + | + | + | + | − | − | − | + |
| G-6-42-42 | + | + | + | + | + | + | + | + | + | + | − | + | − |
| G-6-42-71 | + | + | + | + | + | + | + | + | + | + | − | + | − |
| G-7-24-17 | + | + | + | + | + | + | + | + | + | + | − | + | − |
| G-7-27-18 | + | + | + | + | + | + | + | + | + | − | + | − | + |

*„identified" peptides

TABLE 7b

Amino acid sequences of peptides identified in peptide maps of Fc fragments

| Mass [Da] | Amino Acid Sequence |
|---|---|
| 1169.6 | IQHQDWTGGK (SEQ ID NO: 1) |
| 1243.7 | VNSAAFPAPIEK (SEQ ID NO: 2) |
| 1301.7 | VHNEGLPAPIVR (SEQ ID NO: 3) |
| 1826.9 | EPQVYVLAPPQEELSK (SEQ ID NO: 4) |
| 1854.9 | SVSELPIMHQDWLNGK (SEQ ID NO: 5) |
| 2112.0 | FSWFVDDVEVNTATTKPR (SEQ ID NO: 6) (1 MC)[a] |
| 2258.1 | SVSELPIMHQDWLNGKEFK (SEQ ID NO: 7) (1 MC)[a] |
| 2753.3 | STVSLTCMVTSFYPDYIAVEWQR (SEQ ID NO: 8) (CYS_CAM)[b] |
| 2782.3 | DTLTISGTPEVTCVVVDVGHDDPEVK (SEQ ID NO: 9) (CYS_CAM)[b] |

[a]MC is 1 omitted restriction site

[b]CYS_CAM is iodoacetamide-modified cysteine (modification was introduced intentionally before trypsin digestion of protein, in order to avoid reorganisation of disulphide bridges during hydrolysis)

Analysis of peptide maps of Fc fragments of the obtained mAbs allowed to identify thirteen peptides (Table 7a). Amino acid sequences identified as fragments of IgG antibodies, could be assign to nine of those peptides (Table 7b). The majority of the peptides (9/13) shown in Table 7a, are "common" peptides, among which seven are "identified" and two "non-identified" peptides. Another four peptides are "discriminatory" fragments (Table 7a). Amino acid sequences of two of them are known (Table 7b). Identical "discriminatory" peptide profile in Fc fragments was found in two groups of clones, one of which included G-6-42-42, G-6-42-71 and G-7-24-17 mAbs, and the other G-2-14-10 and G-5-32-5 mAbs. Compared to mAbs from the second group, G-7-27-18 mAbs contained additional "discriminatory" peptide. No "discriminatory" fragments were found in G-1-31-22 clone.

Peptide Maps of Fab Fragments

As in case of Fc fragments, analysis of peptide maps of Fab fragments of G-1-31-22, G-2-14-10, G-5-32-5, G-6-42-42, G-6-42-71, G-7-24-17 and G-7-27-18 clones allowed to identify "common" and "discriminatory" peptides. "Common" peptides from Fab fragments of antibodies and amino acid sequences of identified "common" peptides are shown in Table 8(a, b), below.

More specifically, Table 8 shows (a) "common" peptides in peptide maps of Fab fragments of G-1-31-22, G-2-14-10, G-5-32-5, G-6-42-42, G-6-42-71, G-7-24-17 and G-7-27-18 mAbs and (b) amino acid sequences of identified "common" peptides. Peptide maps, obtained as a result of trypsinolysis, were analysed using MALDI TOF/TOF mass spectrometry. Peptides were identified based on the obtained peptide maps and fragmentation spectra using databases available in Mascot system.

TABLE 8a

| Peptide maps of Fab fragments of monoclonal antibodies (mAbs) - "common" peptides | | | | | | | | | |
|---|---|---|---|---|---|---|---|---|---|
| mAb | Mass [Da] | | | | | | | | |
| clones | 1696.9* | 1666.8 | 1678.8 | 2015.0 | 2028.0 | 2037.0 | 2255.2 | 2421.0 | 2439.1 |
| G-1-31-22 | + | + | + | + | + | + | + | + | + |
| G-2-14-10 | + | + | + | + | + | + | + | + | + |
| G-5-32-5 | + | + | + | + | + | + | + | + | + |
| G-6-42-42 | + | + | + | + | + | + | + | + | + |
| G-6-42-71 | + | + | + | + | + | + | + | + | + |
| G-7-24-17 | + | + | + | + | + | + | + | + | + |
| G-7-27-18 | + | + | + | + | + | + | + | + | + |

*"identified" peptides

TABLE 8b

| Amino acid sequences of "common" peptides identified in peptide maps of Fab fragments | |
|---|---|
| Mass [Da] | Amino Acid Sequence |
| 1696.9 | PAVLNQPSSVSGSLGQR (SEQ ID NO: 10) |

Analysis of peptide maps of Fab fragments of the obtained antibodies allowed to identify nine "common" peptides (Table 8a). Among them, only one (1696.9 Da) was identified using Mascot search engine. It was assign amino acid sequence shown in Table 9b. Although for most of the other peptides good quality fragmentation spectra were obtained, they could not be identified based on protein databases.

"Discriminatory" peptides in peptide maps of Fab fragments of G-1-31-22, G-2-14-10, G-5-32-5, G-6-42-42, G-6-42-71, G-7-24-17 and G-7-27-18 antibodies, as well as amino acid sequences of identified "discriminatory" peptides are shown in Table 9 (a, b), below.

More specifically, Table 9 shows (a) "discriminatory" peptides in peptide maps of Fab fragments of G-1-31-22, G-2-14-10, G-5-32-5, G-6-42-42, G-6-42-71, G-7-24-17 and G-7-27-18 antibodies and (b) amino acid sequences of identified "discriminatory" peptides. Peptide maps, obtained as a result of trypsinolysis, were analysed using MALDI TOF/TOF mass spectrometry. Peptides were identified based on the obtained peptide maps and fragmentation spectra using databases available in Mascot system.

TABLE 9a

| Peptide maps of Fab fragments of monoclonal antibodies (mAbs) - "differentiating" peptides | | | | | | | | | | | | | | |
|---|---|---|---|---|---|---|---|---|---|---|---|---|---|---|
| mAb | Mass [Da] | | | | | | | | | | | | | |
| clones | 1944.1 | 1445.7 | 1515.8 | 1705.9* | 1111.5 | 1800.8 | 1580.9 | 1430.7 | 1884.0 | 1647.8 | 1819.8 | 1110.5 | 1872.1* | 3300.5* |
| G-1-31-22 | − | + | + | + | + | − | − | − | + | − | − | − | − | − |
| G-2-14-10 | + | + | − | + | − | − | − | − | − | − | − | − | − | − |
| G-5-32-5 | + | + | − | − | − | − | − | − | − | + | + | + | − | − |
| G-6-42-42 | + | − | + | − | − | − | + | − | − | − | − | − | − | − |
| G-6-42-71 | + | − | + | − | − | − | + | − | − | − | − | − | − | − |
| G-7-24-17 | + | − | + | + | + | + | − | + | − | − | − | − | − | − |
| G-7-27-18 | − | + | − | + | + | + | − | − | − | − | − | − | + | + |

*"identified" peptides

TABLE 9b

| Amino acid sequences of "discriminatory" peptides identified in peptide maps of Fab fragments | |
|---|---|
| Mass [Da] | Amino Acid Sequence |
| 1705.9 | LWIYGTSDLASGVPAR (SEQ ID NO: 11) |
| 3300.5 | ATLTVDASSSTAYIQLSSLSSEDSAVYFCAR (SEQ ID NO: 12) |

Analysis of peptide maps of Fab fragments from the obtained antibodies determined fourteen "differentiating" peptides, among which three of 1705.9 Da, 1872.1 Da and 3300.5 Da molecular weight were identified using protein databases (Table 9a). Sequences shown in Table 9b were assigned to peptides 1705.9 Da and 3300.5 Da. Three "differentiating" peptides were recognised in Fab fragments of clones G-2-14-10, G-6-42-42 and G-6-42-71, five of clones G-1-31-22 and G-5-32-5, and six of clones G-7-24-17 and G-7-27-18.

Profiles of "Differentiating" Peptides in Peptide Maps of Fab Fragments

Peptide maps of Fab fragments of antibodies G-1-31-22, G-2-14-10, G-5-32-5, G-6-42-42, G-6-42-71, G-7-24-17 and G-7-27-18 were subjected to detailed comparative analysis. Table 10 (a-e) shows profiles of "discriminatory" peptides from Fab fragments of individual mAbs and their comparison with profiles of the other antibody clones. Peptides present in peptide map of only one, particular antibody clone were identified among "discriminatory" peptides and are further referred to as peptides characteristic for that clone.

More specifically, Table 10 shows "discriminatory" peptides in peptide maps of Fab fragments of clones: (a) G-6-42-42 and G-6-42-71, (b) G-2-14-10 and G-5-32-5, (c) G-1-31-22, (d) G-7-24-17, (e) G-7-27-18, obtained as a result of trypsinolysis nad analysed using MALDI TOF/TOF mass spectrometry.

TABLE 10a

"Differentiating" peptides in peptide maps of Fab fragments of G-6-42-42 and G-6-42-71 clones

| mAb clones | Mass [Da] 1580.9 | 1515.8 | 1944.1 |
|---|---|---|---|
| G-6-42-42 | + | + | + |
| G-6-42-71 | + | + | + |
| G-7-24-17 | − | + | + |
| G-1-31-22 | − | + | − |
| G-2-14-10 | − | − | + |
| G-5-32-5 | − | − | + |
| G-7-27-18 | − | − | − |

For G-6-42-42 and G-6-42-71 antibodies, the same "discriminatory" fragments were observed, derived both from Fab part (Table 10a), and Fc part (Table 7a). Those are the only clones among generated mAbs, for which identical peptide maps were obtained. It was assumed, that they represent one antibody clone. In Fab part of G-6-42-42 (G-6-42-71) antibodies, 1580.9 Da peptide characteristic for this clone was recognized. It was also found, that G-6-42-42 (G-6-42-71) antibodies differ from four out of five other clones in that they contain, at the same time, 1515.8 Da and 1944.1 Da fragments.

TABLE 10b

"Differentiating" peptides in peptide maps of Fab fragments of G-2-14-10 and G-5-32-5 clones

| mAb clones | Mass [Da] 1110.5 | 1647.8 | 1819.8 | 1705.9* | 1445.7 | 1944.1 |
|---|---|---|---|---|---|---|
| G-2-14-10 | − | − | − | + | + | + |
| G-5-32-5 | + | + | + | − | + | + |
| G-1-31-22 | − | − | − | + | + | − |
| G-7-27-18 | − | − | − | + | + | − |

TABLE 10b-continued

"Differentiating" peptides in peptide maps of Fab fragments of G-2-14-10 and G-5-32-5 clones

| mAb clones | Mass [Da] 1110.5 | 1647.8 | 1819.8 | 1705.9* | 1445.7 | 1944.1 |
|---|---|---|---|---|---|---|
| G-7-24-17 | − | − | − | + | − | + |
| G-6-42-42 (G-6-42-71) | − | − | − | − | − | + |

*-identified" peptides

As a result of digestion of Fab part of G-2-14-10 clone, three "discriminatory" peptide were obtained (Table 10b), including one identified, with a mass of 1705.9 Da (Table 9b). Among peptides derived from Fab fragment of G-2-14-10 antibodies, no peptide characteristic for this clone was found. In peptide map of Fab fragment of G-5-32-5 antibodies, five "non-identified" "discriminatory" peptides were found, including three characteristic for this clone 1110.5 Da, 1647.8 Da and 1819.8 Da (Table 10b). Both G-2-14-10 mAb, and G-5-32-5 mAb differ from four other clones in that at the same time they contain 1445.7 Da and 1944.1 Da peptides. Profiles of "discriminatory" peptides, shown in Table 10b, indicate that G-2-14-10 and G-5-32-5 antibodies are different clones, and at the same time each of them is different than other antibody clones.

TABLE 10c

"Discriminatory" peptides in peptide map of Fab fragment of G-1-31-22 clone

| mAb clones | Mass [Da] 1884.0 | 1705.9* | 1111.5 | 1445.7 | 1515.8 |
|---|---|---|---|---|---|
| G-1-31-22 | + | + | + | + | + |
| G-7-27-18 | − | + | + | + | − |
| G-7-24-17 | − | + | + | − | + |
| G-2-14-10 | − | + | − | + | − |
| G-5-32-5 | − | − | − | + | − |
| G-6-42-42 (G-6-42-71) | − | − | − | − | + |

*-identified" peptides

Analysis of peptide maps of Fab fragment of G-1-31-22 clone, enabled identification of five "discriminatory" peptide (Table 10c), including one identified, with a mass of 1705.9 Da (Table 9b). In the peptide map of G-1-32-22 mAb, 1884.0 Da peptide characteristic for this clone was recognized. G-1-31-22 antibodies differ from other clones also by simultaneous presence of "non-identified" 1111.5 Da, 1445.7 Da and 1515.8 Da peptides.

TABLE 10d

"Discriminatory" peptides in peptide map of Fab fragment of G-7-24-17 clone

| mAb clones | Mass [Da] 1430.7 | 1705.9* | 1111.5 | 1515.8 | 1800.8 | 1944.1 |
|---|---|---|---|---|---|---|
| G-7-24-17 | + | + | + | + | + | + |
| G-1-31-22 | − | + | + | + | − | − |
| G-7-27-18 | − | + | + | − | + | − |
| G-6-42-42 (G-6-42-71) | − | − | − | + | − | + |

TABLE 10d-continued

| "Discriminatory" peptides in peptide map of Fab fragment of G-7-24-17 clone | | | | | | |
|---|---|---|---|---|---|---|
| mAb | Mass [Da] | | | | | |
| clones | 1430.7 | 1705.9* | 1111.5 | 1515.8 | 1800.8 | 1944.1 |
| G-2-14-10 | − | + | − | − | − | + |
| G-5-32-5 | − | − | − | − | − | + |

*-identified" peptides

In the peptide map of Fab fragment of G-7-24-17 clone, six "discriminatory" peptides were found (Table 10d), including one with a mass of 1705.9 Da, which was identified (Table 9b). In Fab part of G-7-24-17 antibodies, 1430.7 Da peptide characteristic for this clone was recognized. G-7-24-17 clone differs also by simultaneous presence of 1111.5 Da, 1515.8 Da, 1800.8 Da and 1944.1 Da peptides.

TABLE 10e

| "Discriminatory" peptides in peptide map of Fab fragments of G-7-27-18 clone | | | | | | |
|---|---|---|---|---|---|---|
| mAb | Mass [Da] | | | | | |
| clones | 1872.1* | 3300.5* | 1705.9* | 1111.5 | 1445.7 | 1800.8 |
| G-7-27-18 | + | + | + | + | + | + |
| G-1-31-22 | − | − | + | + | + | − |
| G-7-24-17 | − | − | + | + | − | + |
| G-2-14-10 | − | − | + | − | + | − |
| G-5-32-5 | − | − | − | − | + | − |
| G-6-42-42 (G-6-42-71) | − | − | − | − | − | − |

*-identified" peptides

Analysis of peptide map of Fab fragment of G-7-27-18 clone enabled identification of six "discriminatory" peptides (Table 10e). Among them, there are three peptides with a mass of 1705.9 Da, 1872.1 Da and 3300.5 Da, which were identified (Table 9b). Peptides: 1872.1 Da and 3300.5 Da were found only in peptide map of G-7-27-18 mAb. Moreover, G-7-27-18 clone differs from other antibodies by simultaneous presence of 1111.5 Da, 1445.7 Da and 1800.8 Da peptides.

Summary

As a result of ficin digestion, Fc and Fab fragments of G-1-31-22, G-2-14-10, G-5-32-5, G-6-42-42, G-6-42-71, G-7-24-17 and G-7-27-18 antibodies were obtained and then their peptide maps were generated as a result of trypsinolysis. Based on the obtained peptide maps and fragmentation spectra, an attempt was made to identify peptides using databases available in Mascot system.

Most peptides in the maps of Fc fragments of analysed mAbs (Table 7a) were "common" peptides (9/13; 69%). Amino acid sequences of most of the peptides derived from Fc fragments (9/13; 69%) were found in protein databases (Table 7b). The obtained results are consistent with the current state of knowledge, that within the species and isotype, Fc fragments are conserved part of immunoglobulin, without relevance to the specificity of antibodies. Unlike in the case of Fc fragments, in peptide maps of Fab fragments of tested antibodies (Tables 8a, 9a) the majority were "discriminatory" peptides (14/23; 61%). Additionally, only small number of peptides (4/23; 17%) was identified in Fab fragments (Tables 8b, 9b), significantly less than in Fc fragments (17% vs 69%). Fab fragments are characterised by a great sequence variability determining their specificity, and therefore databases can be incomplete in those areas.

Of major importance for the identification of the obtained antibodies was comparative analysis of peptide maps of antibody variable fragments responsible for antigen binding, i.e. Fab fragments. Clones discrimination was based mainly on the presence of peptides characteristic for individual clones or particular groups of clones ("discriminatory peptides"). The most informative was the presence of peptides having unique amino acid sequences, which were not deposited in protein databases so far ("non-identified discriminatory peptides").

Detailed analysis of peptide maps of Fab fragments showed, that the obtained antibodies differ in the number and the profile of "discriminatory" peptides (Table 10a-e). Among seven obtained mAbs, six different antibody clones were recognized and it was shown, that G-6-42-42 and G-6-42-71 antibodies are the same clone. This corresponds to the results of immunoreactivity profile-based mAbs discrimination, which are shown in Example 8.

Example 10 DETERMINATION OF ACTIVITY OF THE OBTAINED MABS IN HEMAGGLUTINATION INHIBITION TEST Monoclonal antibodies generated as a result of mice vaccination with rHA-A/H5N1/Qinghai and selected for the specificity against HA of H5 serotype, were subjected to HI test. The test uses the ability of antibodies binding specifically to particular antigenic sites on HA molecule to block binding between the protein and erythrocyte surface receptors, what is manifested by the lost ability of the antigen to erythrocyte agglutination.

The studies included purified G-1-31-22, G-2-14-10, G-5-32-5, G-6-42-42, G-6-42-71, G-7-24-17 and G-7-27-18 antibodies. As reference antibodies, commercial anti-H5 HA mAbs (Pierce/Thermo Scientific, Acris Antibodies), denoted mAb 7, mAb 8, mAb 9, were used. According to specifications, antibodies recognize H5 HA in HI test (List A). HI test was performed using H5N3 LPAIVs as an antigen. Hemagglutinin of this AIV strain is characterized by the highest homology with immunogen's source sequence among hemagglutinins of H5 serotype IVs used in the mAb manufacturing procedure (List E, F). It is the case for both full-length protein, and HA1 subunit, where epitopes for HI antibodies are localised. HI test was also performed using H5N2 LPAIV as an antigen. Comparative analyses of H5N3, H5N1, H5N9 and H5N2 AIV hemagglutinin showed, that HA HA1 subunit of H5N2 virus has the lowest homology to HA1 subunit of the immunogen, if all homology factors are taken into account: Max Score, Total Score, Identities (List F). According to the results of ELISA using four LPAIV strains of H5 serotype (Example 7), reactivity of all obtained mAb clones with H5N3 AIV was the highest, whereas with H5N2 AIV was one of the lowest (FIG. 13) and was 24-35% of reactivity determined with H5N3 virus (FIG. 14). IZSVe-certified viruses and anti-sera were used in HI test and are described below, in List G.

List G Influenza viruses and anti-sera used in the studies of hemagglutination inhibition activity of the obtained mAbs.

| HI test with low pathogenicity H5N3 avian influenza virus | | | Origin |
|---|---|---|---|
| Antigen | LPAIV | A/duck/It/775/04(H5N3) | x-OvO |
| Positive Control | Antiserum | A/duck/It/775/04(H5N3) | x-OvO |

-continued

| List G Influenza viruses and anti-sera used in the studies of hemagglutination inhibition activity of the obtained mAbs. | | | |
|---|---|---|---|
| Negative control | Antiserum | A/macaw/626/80(H7N7) | x-OvO |
| HI test with low pathogenicity H5N2 avian influenza virus | | | Origin |
| Antigen | LPAIV | A/turk/It/80(H5N2) | x-OvO |
| Positive Control | Antiserum | A/turk/It/80(H5N2) | x-OvO |
| Negative control | Antiserum | A/macaw/626/80(H7N7) | x-OvO |

LPAIV—low-pathogenic (LP) avian influenza virus (AIV)

x-OvO Limited (Great Britain), Istituto Zooprofilattico Sperimentale delle Venezie (IZSVe, Italy)

Fresh preparation of erythrocytes collected from the blood of SPF chickens from sterile culture in DPD, NVR was used in the test. Each performed HI test included positive control with anti-H5N3 AIV or H5N2 AIV antisera incubated with H5N3 or H5N2 viral antigens, respectively. Regardless the antigen used, negative controls were samples containing anti-H7N7 AIV antiserum. For all tested antibodies and antisera, blood cells controls without viral antigen were performed (internal assay control). For each HI test, hemagglutination unit was determined (HAU).

To evaluate HI activities of the obtained mAbs, series of 2-fold dilutions of selected antibody clones and their mixture in PBS-Dulbecco (Sigma-Aldrich) were prepared in 96 well conical bottom (V) plates (CellStar/Greiner bio-one). Thus, antibody dilutions in the range from 2× to 4096 (8192)× were prepared. Reference anti-H5 HA mAbs were diluted analogically. On each test plate, serial dilutions of control antisera against H5N3 AIV or H5N2 AIV (positive control) and H7N7 AIV (negative control) were prepared, resulting in dilutions from 2× to 4096(8192)×. Next, into each of the wells containing mAbs and antisera diluted 4× and more in the final volume of 25 μL, 25 μL of H5N3 AIV or H5N2 AIV suspension containing 4 HAU was added. 25 μL PBS-Dulbecco was added into each of the wells for blood cells control containing 2-fold diluted mAbs and antisera. After 25 min of initial incubation at room temperature, 25 μL 1% erythrocyte suspension was added into each well. The results were observed after minimum 30 min incubation with blood cells.

According to the principle of the test, hemagglutination inhibition was evaluated visually by comparing samples with blood cell controls. In HI-positive samples, virus antigens do not agglutinate erythrocytes and therefore they fall freely on the bottom of the wells, as in the blood cells control samples. HI titer of monoclonal antibodies was defined as the lowest concentration of antibodies causing hemagglutination inhibition. HI titer of antisera was generally defined as the inverse of the highest dilution, which inhibits erythrocyte agglutination by viral antigens. The results of HI tests for G-1-31-22, G-2-14-10, G-5-32-5, G-6-42-42, G-6-42-71, G-7-24-17, G-7-27-18 mAbs using H5N3 and H5N2 AIVs as antigens are shown in Table 11, below, together with the results for reference antibodies and control antisera.

More specifically, Table 11 shows HI tests results for G-1-31-22, G-2-14-10, G-5-32-5, G-6-42-42, G-6-42-71, G-7-24-17, G-7-27-18 mAbs using H5N3 and H5N2 LPAIV (x-OvO) as antigens. Each test performed included positive control (anti-H5N3 AIV or anti-H5N2 AIV antisera) and negative (anti-H7N7 AIV antiserum), and blood cells controls. In HI test using H5N3 AIV, commercial anti-H5 HA mAbs (Pierce/Thermo Scientific, Acris Antibodies) were used as reference antibodies.

TABLE 11

| mAbs and control antisera | mAb concentrations [μg/mL] Antiserum dilution | Result HI activity | HI titer |
|---|---|---|---|
| HI test with low pathogenicity H5N3 avian influenza virus | | | |
| G-1-31-22 | 0.3-526 | – | – |
| G-2-14-10 | 0.8-1011 | – | – |
| G-5-32-5 | 0.9-1008 | – | – |
| G-6-42-42 | 0.7-1034 | – | – |
| G-6-42-71 | 0.9-973 | – | – |
| G-7-24-17 | 0.5-877 | – | – |
| G-7-27-18 | 0.9-1023 | – | – |
| G-1-31-22 + G-2-14-10 + G-5-32-5 + G-6-42-42 + G-6-42-71 + G-7-24-17 + G-7-27-18 | 0.7-726 | – | – |
| mAb 9 (Pierce/Thermo Sci., Cat. No. MA1-81928) | 0.1-125 | + | 7.8 μg/mL |
| mAb 7 (Acris Antibodies, Cat. No. AM00945PU-N) | 0.1-125 | + | 2.0 μg/mL |
| mAb 8 (Acris Antibodies, Cat. No. AM00941PU-N) | 0.1-25 | + | 1.0 μg/mL |
| Antiserum against H5N3 LPAIV | 4x-2048x (4096x) | + | 1:512, 1:1024 |
| Antiserum against H5N7 LPAIV | 4x-2048x (4096x) | – | – |
| HI test with low pathogenicity H5N2 avian influenza virus | | | |
| G-1-31-22 | 0.5-526 | – | – |
| G-2-14-10 | 1.0-1011 | – | – |
| G-5-32-5 | 1.0-1008 | – | – |
| G-6-42-42 | 1.0-1034 | – | – |
| G-6-42-71 | 0.9-973 | – | – |
| G-7-24-17 | 0.9-877 | – | – |
| G-7-27-18 | 1.0-1023 | – | – |
| Antiserum against H5N2 LPAIV | 4x-4096x | + | 1:512 |
| Antiserum against H5N7 LPAIV | 4x-4096x | – | – |

HI tests showed, that non of the mAb clones produced as a result of mice vaccination with rHA-A/H5N1/Qinghai and selected for serotype specificity, has the ability to inhibit hemagglutination by H5N3 and H5N2 AIVs. No HI activity was showed for G-1-31-22, G-2-14-10, G-5-32-5, G-6-42-42, G-6-42-71, G-7-24-17, G-7-27-18 mAbs, despite using a wide variety of antibody concentrations: from submicrogram to couple of hundreds of grams, wherein some clones were tested in concentration of up to ~1 mg. Under the same conditions, HI titers of commercial mAbs, denoted mAb 9, mAb 7 and mAb 8, determined using H5N3 AIV, were 7.8 μg/mL, 2.0 μg/mL and 1.0 μg/mL, respectively. Correct assay performance was confirmed by high titers of HI-positive control antisera (anti-H5N3 AIV or anti-H5N2 AIV antisera) and no HI activity of negative control antisera (anti-H7N7 antiserum). Additionally, observation of blood cells control samples did not showed, that tested samples of antibodies and antisera influenced the quality of erythrocytes.

G-1-31-22, G-2-14-10, G-5-32-5, G-6-42-42, G-6-42-71, G-7-24-17 and G-7-27-18 antibodies differ from mAb 7 and mAb 8 of narrow and broad range of specificities against H5 HA (FIG. 6), respectively, in this, that they do not inhibit hemagglutination (Table 11), while maintaining broad serotype specificity (FIG. 11, 13). Negative results of HI tests for the produced mAbs (Table 11) together with positive results of ELISA for their reactivity with H5N3 and H5N2 AIV (FIG. 13) indicate, that epitopes recognized by the obtained antibodies may be beyond RBD.

Example 11

The Use of Produced mAbs for the Evaluation of Quality of H5 Hemagglutinin Antigens The main challenge for works on subunit vaccines against influenza, based on the use of hemagglutinin produced using genetic engineering methods, is to obtain viral HA-like antigens. Particularly important for vaccine HA quality is the correctness of structure of HA1 subunit, where conformational epitopes for neutralizing antibodies are localized. One of the indicators of HA proteins usefulness for vaccine manufacturing is the reactivity of antibodies of known properties with produced antigens. Antigenicity studies found broad application in the analysis of HA proteins produced in a form of inclusive bodies in bacterial cells, where suitable protein renaturation and purification methods must be used in order to produce valuable vaccine antigen (Sączyńska V., 2014). Because newly obtained antibody clones recognize only conformational epitopes of HA1 subunit and show broad range of H5 HA specificities, they can be successfully used in the studies of properties of antigens for production of vaccines against HPIVs of H5 serotype, regardless of the original vaccine antigen sequence. Envisioned is also the use of generated antibodies for controlling stability of antigens and vaccines against influenza. Another possible application for the obtained mAbs is their use to monitor quality of H5 HA proteins intended for use or already used as reagents in diagnostic tests, i.e. for verification whether conformation of serotype-specific epitopes in antigens is correct.

To determine applicability of the obtained antibodies for the evaluation of H5 HA antigens quality, antigenicity tests for bacterial expression system-produced rHA-A/H5N1/Poland using G-6-42-42, G-6-42-71 and G-7-27-18, were performed. Following purification and renaturation, H5 HA protein (17-522 aa, ΔRRRKKR (SEQ ID NO: 13)), produced on the basis of HA sequence of A/swan/Poland/305-135V08/2006 (H5N1) strain of AIVs (IBA), was subjected to analyses, which showed its correct conformation. Test methods and protein properties are described in detail in Example 7. rHA-A/H5N1/Poland was analysed under reducing conditions before and after denaturation. Denaturation was conducted by diluting protein preparation in 2× concentrated denaturation buffer (4% SDS, 625 mM β-mercaptoethanol, 120 mM Tris-HCl, pH 8.0) in 1:1 ratio (v./v.) and by heating the obtained solution in 99° C. for 10 minutes. The antigenicity analysis was performed by ELISA on PolySorp, MediSorp, MaxiSorp and MultiSorp plates (NUNC) coated with conformational and denatured rHA preparation with purity ~80%, which contained hemagglutinin in ~1 μg/mL concentration. Serially 2-fold diluted G-6-42-42, G-6-42-71 and G-7-27-18 mAbs were loaded into plates blocked with 10% FBS/PBS. The assay was performed under conditions described in Example 7. Concentrations interpolated from 4-parameter titration curves with bacterial HA protein were determined using Gene5 software (Bio-Tek).

Figure 18:
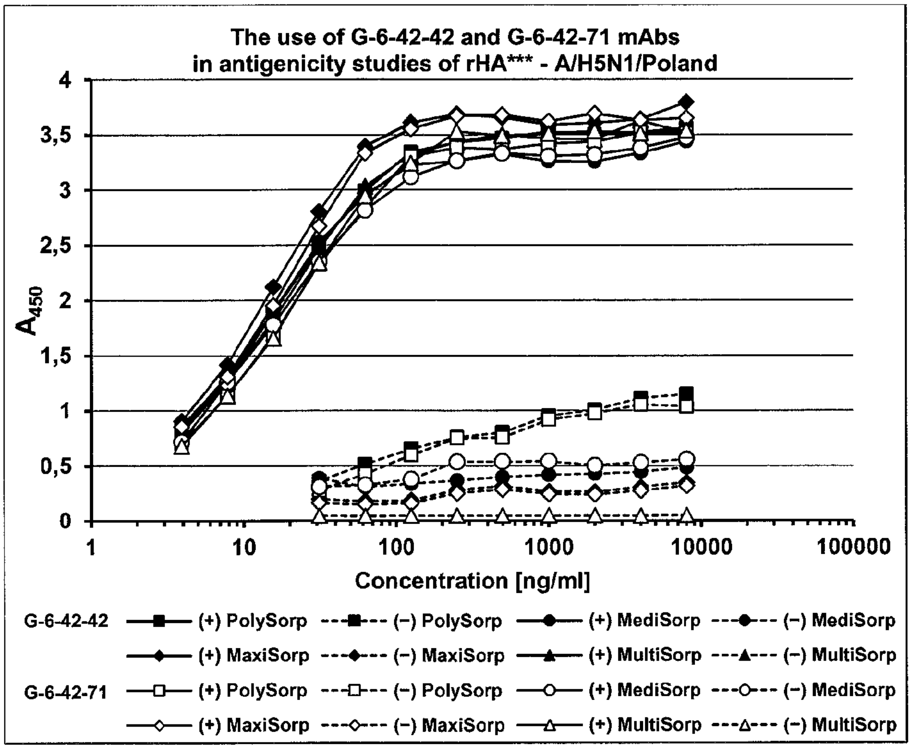
FIG. 18 shows titration curves of G-6-42-42 and G-6-42-71 mAbs on conformational (+) and denatured (−) rHA-A/H5N1/Poland from (***) bacterial expression system. The protein (17-522 aa, ΔRRRKKR (SEQ ID NO: 13)) was produced based on the HA sequence of A/swan/Poland/305-135V08/2006 (H5N1) strain of AIV (IBA). Purified and renatured H5 HA protein was subjected to denaturation in reducing conditions. The assay was performed by ELISA on PolySorp, MediSorp, MaxiSorp and MultiSorp plates (NUNC) coated with rHA preparation with purity ~80%, which contained hemagglutinin in ~1 μg/mL concentration.
Figure 19:
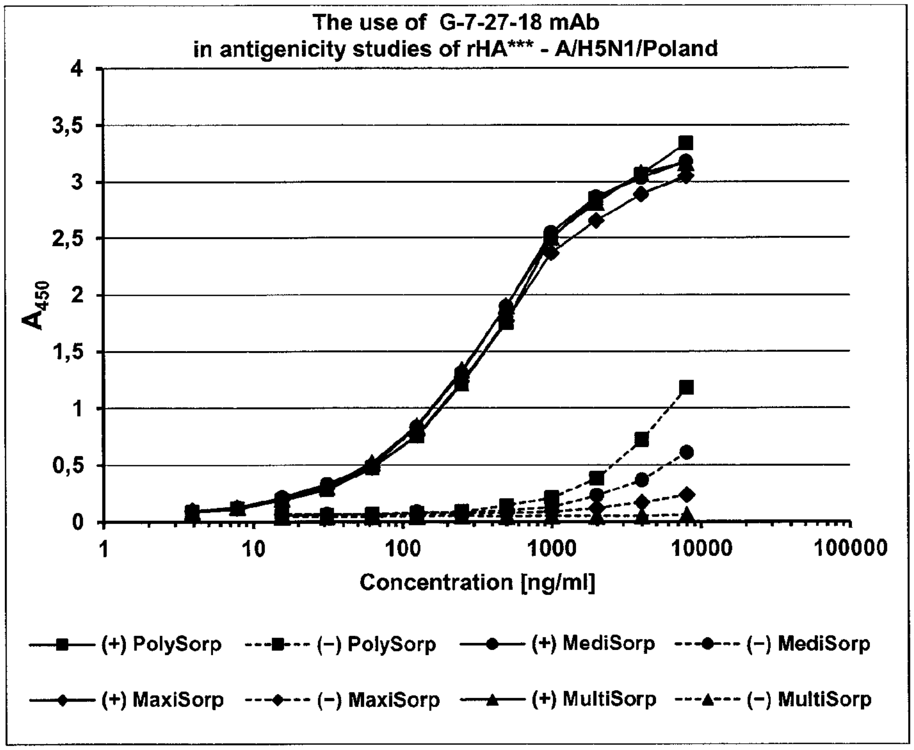
FIG. 19 shows titration curves of G-7-27-18 mAb on conformational (+) and denatured (−) rHA-A/H5N1/Poland from (***) bacterial expression system. The protein (17-522 aa, ΔRRRKKR (SEQ ID NO: 13)) was produced based on the HA sequence of A/swan/Poland/305-135V08/2006 (H5N1) strain of AIV (IBA). Purified and renatured H5 HA protein was subjected to denaturation in reducing conditions. The assay was performed by ELISA on PolySorp, MediSorp, MaxiSorp and MultiSorp plates (NUNC) coated with rHA preparation with purity ~80%, which contained hemagglutinin in ~1 μg/mL concentration.

FIGS. 18 and 19 show the results of antigenicity analysis of conformational and denatured rHA-A/H5N1/Poland from bacterial expression system using G-6-42-42, G-6-42-71 and G-7-27-18 antibodies. The differences in titration curves for G-6-42-42, G-6-42-71 and G-7-27-18 mAbs with conformational and denatured rHA protein, expressed in high levels of ($A_{450}$ reads from the assays with the protein before denaturation and very low reads after denaturation, indicate loss of proper conformation by HA protein under denaturing conditions. In contrary to the results obtained with conformational rHA protein, $A_{450}$ values read in the tests with denatured antigen depended on the type of plate used for antigen binding and were decreasing with an increase of hydrophilicity of the surface being coated. The most important signals from titration of antibodies were read with the antigen, which, following denaturation, was adsorbed on PolySorp plates having high binding affinity for hydrophobic molecules. Concentrations interpolated for $A_{450}$=1.0 from titration curves for G-6-42-42, G-6-42-71 and G-7-27-18 mAbs with denatured, bacterial HA protein bound to this type of plate, were 338-, 389- and 35-fold higher than with conformational protein. Antibodies used in the analysis did not recognize denatured antigen bound to MultiSorp plates of the highest hydrophilicity.

The results described in the present example confirm earlier findings, that generated G-6-42-42, G-6-42-71 and G-7-27-18 antibodies recognize conformational epitopes of hemagglutinin (Examples 5, 7). Some reactivity level of those antibodies with denatured rHA protein, observed in tests using some types of plates, was probably resulting from partial protein renaturation after dilution in PBS under plate-coating conditions.

The results confirm usefulness of the produced antibodies for studying properties of newly obtained H5 HA proteins and for the detection of changes of those proteins during their storage. This is the case for both antigens for the production of vaccines against IVs of H5 serotype, e.g. H5N1 HPAIV, and antigens used in diagnostic tests.

Example 12

The Use of Generated mAbs in Diagnostic Tests

In order to show possible applications of generated mAbs in diagnostic tests, prototype blocking ELISA was developed for detection of anti-H5 HA antibodies (BELISA H5). G-7-27-18 clone was used in BELISA H5. As the antigen, 17-530 aa protein (ΔRRRKKR (SEQ ID NO: 13), 6×His (SEQ ID NO: 14)) having sequence of HA of A/swan/Poland/305-135V08/2006 strain of H5N1 virus, produced in baculovirus expression system (OET), was used. The protein properties are described in detail in Example 2. BELISA H5 was optimized. Assays using polystyrene plates with various polarity enabled selection of the best plate for antigen binding and epitop presentation for G-7-27-18 mAb. Preferable conditions for plates incubation at particular stages of purification procedure were determined in additional experiments. Optimum concentration/dilution of reagents were determined by titration.

In optimal variant of BELISA H5, MediSorp plates (NUNC) were coated with antigen in 0.5 μg/mL (50 μL/well) overnight, at 2-8° C. Unspecific binding sites on the plates were blocked for 1 h at room temperature using Protein-Free T20 (PBS) Blocking Buffer (200 μL/well) from Pierce. Into each well for control mAbs, 100 μL of incubation buffer (1% BSA/PBS) was added, and into each of the other wells—50 μl of incubation buffer was added. Control and tested serum samples were diluted in the wells of the plate by adding 50 μL of serum to 50 μL of 1% BSA/PBS. The samples were incubated in the plates for 1 h at 37° C., with shaking (150 rpm). Next, 7-27-18 mAb (50 μL/well) diluted to 1 μg/mL in Antibody Stabilizer PBS (Candor Bioscience) was added into the wells, and the plate was incubated again for 1 h at 37° C., with 150 rpm. HRP-labelled anti-mouse IgG antibodies (γ-chain specific, Sigma-Aldrich) were used for the detection of antigen-bound mAbs. Secondary antibodies were diluted 1:3500 in HRP-Protector (Candor Bioscience) and incubated on the plates (50 μL/well) for 1 h at 37° C., at 150 rpm. TMB (Sigma-Aldrich) was used as a substrate for HRP (50 μl/well). After 15 min incubation at room temperature, reaction was inhibited by 0.5 M $H_2SO_4$ solution (50 μL/well). Absorption of samples was read at λ=450 nm.

Assays were carried out in the presence of control samples. The control of maximum binding of mAb 7-27-18 with H5 HA antigen (mAb control) was obtained in the wells of the plate, into which serum was not added. Normal chicken serum (Abcam) was used as negative control, whereas antisera obtained by vaccination of SPF chickens with inactivated H5N3 and H5N2 AIVs (x-OvO) were used as positive controls. Strong positive control was anti-H5N3 AIV antiserum, and weak positive control was anti-H5N2 AIV antiserum. 13 BELISA H5s were performed according to the above protocol. mAb control was assayed in 8 repeats on each plate. Remaining control samples and serum test samples were analysed in duplicates. The level of mAb 7-27-18-antigen binding inhibition by sera, expressed as percent, was calculated according to the formula: % inhibition=100−[($A_{450}$ sample/$A_{450}$ control mAb)×100]. Mean $A_{450}$ values for control mAb and tested samples were included into calculations.

Initial evaluation of diagnostic value of BELISA H5 was conducted using commercially available chicken sera (Abcam, x-OvO), sera from DPD, NVRI, as well as serum samples prepared during chicken immunization studies conducted by IBA. Sera for analysis were previously tested for the presence of antibodies against HA of influenza viruses using HI test. HI test allows to classify animals as anti-HA-positive or anti-HA-negative, and to determine serotype specificity of anti-sera. In the validation procedures of test for diagnostics of IV infections, HI test is treated as a so-called gold standard. HI titer for normal chicken sera (Abcam) and sera from immunization studies (IBA) were determined in IBA using H5N2 AIV (x-OvO) as antigen. Antisera (x-OvO), certified by IZSVe, were characterised using specified HI titer values.

Anti-H5-negative sera were from a group of non-vaccinated chickens differentiated in terms of type, breed, age and conditions under which chickens were raised. Anti-H5-negative sera, as well as sera positive against HA of H1-H4 and H6-H16 serotypes (x-OvO) were obtained by immunization of SPF chicken with inactivated AIVs, shown in List C. Anti-H5-positive sera were obtained by animal vaccination using H5 HA antigens from: SPF chickens with inactivated H5N1, H5N2, H5N3, H5N9 (x-OvO) AIVs shown in List C and free range chickens with recombinant H5 HA protein (rH5-*E. coli*). rH5-*E. coli* protein (the first antigen variant) was produced in IBA based on HA sequence from A/swan/Poland/305-135V08/2006 strain of H5N1 virus. The protein properties are described in Example 7. H5 HA antigens with varied sequences were used to obtain antisera. Indicators for relative homology of those antigens are shown in List E and F. Samples used for the initial evaluation of diagnostic values of BELISA H5, are described in detail in the List, below.

List H Samples of chicken sera analysed by BELISA H5 (IBA) using G-7-27-18 mAb.

| Sera | Number of chickens/ series | Number of samples | HI titer | Origin |
|---|---|---|---|---|
| Controls for bELISA | | | | |
| Negative control Normal chicken serum | Series 1 | 1 | <1:8[6] | Abcam (Cat. No. ab7477) |
| Positive control, strong anti-H5N3 AIV (1)[1] | Series 1 | 1 | 1:512[7] | x-OvO* |
| Positive control, weak anti-H5N2 AIV (3)[1] | Series 1 | 1 | 1:512[7] | x-OvO* |
| Anti-H5-negative (1) | | | | |
| non-laying type SPF chickens[2] | 10 | 18 | n.d.[8] | DPD, NVRI ** |
| laying-type chickens[3] | 30 | 130 | <1:8[6] | IBA*** |
| meat-type chickens[4] | 42 | 61 | <1:8[6] | controls in immunization tests |
| Anti-H5-negative (2) | | | | |
| anti AIV: H1-H4, H6-H12, H14-H16[1] | after 1 series | 20 | positive[7] | x-OvO* |
| anti H13 AIV[1] | 2 series | 2 | positive[7] | x-OvO* |
| Anti-H5-positive (1) | | | | |
| anti H5N1 AIV[1] | 1 series | 1 | 1:512[7] | x-OvO* |
| anti H5N2 AIV[1] | 3 series | 3 | 1:256; 1:512[7] | x-OvO* |
| anti H5N3 AIV[1] | 3 series | 3 | 1:512[7] | x-OvO* |
| anti H5N9 AIV[1] | 3 series | 3 | 1:256; 1:512[7] | x-OvO* |

-continued

| List H Samples of chicken sera analysed by BELISA H5 (IBA) using G-7-27-18 mAb. | | | | |
|---|---|---|---|---|
| Sera | Number of chickens/ series | Number of samples | HI titer | Origin |
| Anti-H5-positive (2) | | | | |
| anti H5 laying-type chickens[5] | 69 | 115 | 1:8 ÷ 1:512[6] | IBA*** immunization tests |

[1]SPF chickens were vaccinated with inactivated AIVs of serotype H1-H16 (List C)

[2]Blood was collected on day 63 and/or 77 of life of laying SPF chickens (White Leghorn) (1 or 2 collections from 1 hen).

[3]Blood was collected from free range laying chickens (Rossa 1) on 49, 56, 63, 70 and 77 day of life of animals (3-5 collections from 1 hen).

[4]Blood was collected from free-range meat-type chickens (Rossa 308) on 21, 35, 38, 42 and 49 day of life of animals (1-4 collections from 1 hen).

[5]Free range laying chickens (Rossa 1) were vaccinated with rH5- *E. coli* protein with HA sequence from A/swan/Poland/305-135V08/2006 strain of H5N1 AIV (EpiFluDatabase Accession No. EPI156789). The blood was collected from the animals 1 and/or 2 weeks following administration of the 2nd dose of antigen, on 56 and/or 63 day of life, or on 70 and/or 77 day of life (1 or 2 collections from 1 hen).

[6]determined using H5N2 AIV (x-OvO) as antigen and HIU = 1:8 (IBA)

[7]according to specification (x-OvO)

[8]not determined

*x-OvO Limited (Great Britain), Istituto Zooprofilattico Sperimentale delle Venezie (IZSVe, Italy))

** Department of Poultry Diseases, National Veterinary Research Institute (Pulawy, Poland)

***Institute of Biotechnology and Antibiotics (Warsaw, Poland)

Analysis of H5-negative sera with BELISA H5 allowed for determination of cut-off values for the developed test (mean value % inhibition+2×SD), and therefore interpretation of the results for the tested samples. Values of % inhibition higher than cut-off values mean, that samples are seropositive, and lower—that they are seronegative. The results of samples analysis using BELISA H5 H5 relative to cut-off values are presented in FIG. 20 Data from negative control assays, anti-H1 (H2-H16)-positive sera was presented as a mean value of % inhibition from a given number of independent assays (n) for each sample. The results of the other analyses were presented as mean value of % inhibition from a given number of samples (n) in each serum group.

Figure 20:
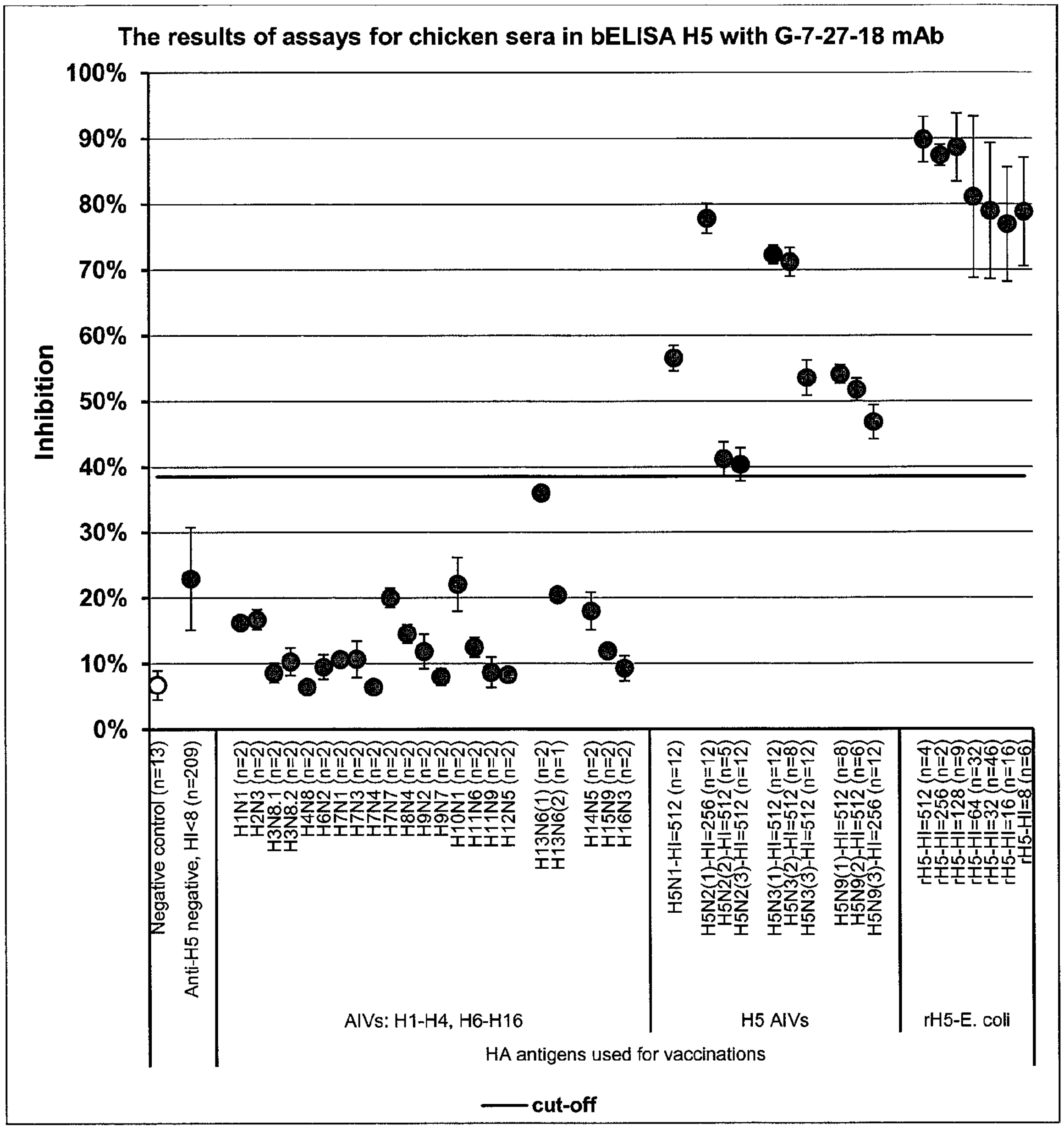
FIG. 20 shows the results of chicken serum assays with the use of blocking ELISA for the detection of antibodies against H5 HA (BELISA H5), which was developed and optimized in IBA. G-7-27-18 mAb was used in BELISA H5 assay. Analysed samples were previously classified as anti-H5-positive or -negative based on the results of HI test. The "cut-off" value was defined based on the results of assays for anti-H5-negative serum samples (mean value % inhibition+2×SD). Data from negative control assays, anti-H1 (H2-H16)-positive sera was presented as a mean value of % inhibition from a given number of independent assays (n) for each sample. The results of the other analyses were presented as mean value of % inhibition from a given number of samples (n) in each serum group. In the Figure, the results of assays for negative control, as well as strong and weak positive control, are marked.

Mean values of % inhibition of negative control, anti-H5-negative sera from non-vaccinated chickens and vaccinated AIVs of serotypes other that H5 (H1-H4, H6-H16) are shown in FIG. 20, below cut-off values. In turn, mean values of % inhibition of anti-H5-positive sera of chickens vaccinated with AIVs of H5 serotype and rH5-*E. Coli* protein are shown above cut-off values. Obtained results suggest, that prototype BELISA H5 test allows distinguishing between chickens vaccinated with H5 HA antigens and anti-H5-negative chickens. Importantly, antisera against AIVs of H1-H4 and H6-H16 serotypes do not cause cross-reactions in the developed test. BELISA H5 test would probably allow also unambiguous diagnostics of animals infected with IVs of H5 serotype, such as H5N1 HPAIV. In case of vaccinations against HPAIV with the use of H5 HA proteins, BELISA H5 test together with the test for detection of antibodies against other IV antigens e.g. neuraminidase, could be used as so-called DIVA test designated for distinguishing infected animals from vaccinated animals.

Characterisation of prototype BELISA H5 was expanded to include an initial identification of the key validation parameters of the diagnostic test. Reproducibility of the assays was determined by performing independent assays for mAbs controls, negative controls (normal chicken serum) and positive controls (antisera against H5N3 and H5N2 AIVs). Analytical (Asp) and diagnostic (Dsp) specificity of the test was determined by calculating the ratio of samples denoted as true negative (TN) among sera from chickens vaccinated with AIV of H1-H4, H6-H16 serotype (Asp) and anti-H5-negative sera from non-vaccinated group of chickens (Dsp). Diagnostic sensitivity (Dse) of BELISA H5 test was determined by calculating the ratio of samples denoted as true positive (TP) among sera from chickens vaccinated with AIVs of H5 serotype (H5N1, H5N2, H5N3 and H5N9) or rH5-*E. Coli* protein. The results for the validation parameters of BELISA H5 are shown in Table 12, below.

More specifically, Table 12 shows the results of initially determined validation parameters of blocking ELISA for the detection of antibodies against H5 HA (BELISA H5) in chicken sera, which was developed and optimized in IBA. G-7-27-18 mAb was used in BELISA H5 assay. Analysed samples were previously classified as anti-H5-positive or -negative based on the results of HI test. Reproducibility of assays was determined by performing independent assays for control samples. Analytical (Asp) and diagnostic (Dsp) specificity of the test was evaluated by calculating the ratio of samples denoted as true negative (TN) among anti-H5-negative sera. Diagnostic sensitivity (Dse) was determined by calculating the ratio of samples denoted as true positive (TP) among anti-H5-positive sera.

TABLE 12

| Sera | Number of | Number of | Result | | |
|---|---|---|---|---|---|
| Reproducibility of assays [$A_{450}$] | samples | assays | Mean | SD | RSD |
| Control G-7-27-18 mAb | 1 | 13 | 1.566 | 0.111 | 7.1% |
| Negative control Normal chicken serum | 1 | 13 | 1.460 | 0.114 | 7.8% |
| Positive control, strong anti-H5N3 AIV (1) | 1 | 12 | 0.439 | 0.044 | 10.0% |

TABLE 12-continued

| | | | | | |
|---|---|---|---|---|---|
| Positive control, weak anti-H5N2 AIV (3) | 1 | 12 | 0.944 | 0.083 | 8.8% |
| Analytical specificity (Asp) | | | TN | FP | Asp TN/(TN + FP) |
| anti-H1(H2-H4, H6-H16) AIV | 22 | 43 | 43 | 0 | 100% |
| Diagnostic specificity (Dsp) | | | TN | FP | Dsp TN/(TN + FP) |
| anti-H5-negative | 209 | 209 | 204 | 5 | 97.6% |
| | | | TP | FN | Dse TP/(TP + FN) |
| Diagnostic sensitivity 1 (Dse 1) | | | | | |
| anti-H5 AIV | 10 | 99 | 97 | 2 | 98.0% |
| Diagnostic sensitivity 2 (Dse 2) | | | | | |
| anti-H5 | 115 | 115 | 114 | 1 | 99.1% |

TN—true negative
FP—false positive
TP—true positive
FN—false negative

The results of assays for control samples, anti-H5 negative and positive samples indicate, that prototype BELISA H5 test is characterized by satisfying reproducibility (RSD: 7.1%-10.0%) and high analytical specificity factors (Asp: 100%), as well as diagnostic specificity and sensitivity (Dsp: 97.6%; Dse 1: 98.0%; Dse 2: 99.1%).

LITERATURE

Cao Z i wsp. The epitope and neutralization mechanism of AVFluIgG01, a broad-reactive human monoclonal antibody against H5N1 influenza virus. PLoS One. 2012; 7:e38126.

Chiu F F i wsp. Immunological study of HA' domain of hemagglutinin of influenza H5N1 virus. Biochem Biophys Res Commun. 2009; 383:27-31.

Corti D i wsp. A neutralizing antibody selected from plasma cells that binds to group 1 and group 2 influenza A hemagglutinins. Science. 2011; 333:850-6.

Dlugolenski D i wsp. Production of H5-specific monoclonal antibodies and the development of a competitive enzyme-linked immunosorbent assay for detection of H5 antibodies in multiple species. Avian Dis. 2010; 54(1 Suppl):644-9.

Du L i wsp. Identification and structural characterization of a broadly neutralizing antibody targeting a novel conserved epitope on the influenza virus H5N1 hemagglutinin. J Virol. 2013; 87:2215-25.

Ekiert D C i wsp. Antibody recognition of a highly conserved influenza virus epitope. Science. 2009; 324:246-51.

Grabowska I i wsp. Electrochemical biosensors for detection of avian influenza virus—current status and future trends. Acta Biochim Pol. 2014; 61:471-8.

Ha Y i wsp. H5 avian and H9 swine influenza virus haemagglutinin structures: possible origin of influenza subtypes. EMBO J. 2002; 21:865-75.

Hvistendahl M. Avian influenza. Enigmatic bird flu strain races across the U.S. Midwest. Science. 2015; 348:741-2.

ICTV, International Committee On Taxonomy Of Viruses, Taxonomy History, ICTV, 2014. [world wide web address: ictvonline.org/virusTaxonomy.asp?taxnode_id=20142704].

Ip H S i wsp. Novel Eurasian highly pathogenic avian influenza A H5 viruses in wild birds, Washington, USA, 2014. Emerg Infect Dis. 2015; 21:886-90.

Jarocka U i wsp. An immunosensor based on antibody binding fragments attached to gold nanoparticles for the detection of peptides derived from avian influenza hemagglutinin H5. Sensors (Basel). 2014; 14:15714-28.

Koh Y T i wsp. Immunological consequences of using three different clinical/laboratory techniques of emulsifying peptide-based vaccines in incomplete Freund's adjuvant. J Transl Med. 2006; 4:42.

Köhler G, Milstein C. Continuous cultures of fused cells secreting antibody of predefined specificity. Nature. 1975; 256:495-7.

Lamb R A, Choppin P W. The gene structure and replication of influenza virus. Annu Rev Biochem. 1983; 52:467-506.

Lapolla A i wsp. Evaluation of IgG glycation levels by matrix-assisted laser desorption/ionization mass spectrometry. Rapid Commun Mass Spectrom. 1997; 11:1342-6.

Lapolla A i wsp. (a) Matrix-assisted laser desorption/ionization mass spectrometry, enzymatic digestion, and molecular modeling in the study of nonenzymatic glycation of IgG. J Am Soc Mass Spectrom. 2000; 11:153-9.

Lapolla A i wsp. (b) The role of mass spectrometry in the study of non-enzymatic protein glycation in diabetes. Mass Spectrom Rev. 2000; 19:279-304.

Lebarbenchon C i wsp. Evaluation of a commercial enzyme-linked immunosorbent assay for detection of antibodies against the H5 subtype of Influenza A virus in waterfowl. Influenza Other Respir Viruses. 2013; 7:1237-40.

Miyagawa E i wsp. Development of a novel rapid immunochromatographic test specific for the H5 influenza virus. J Virol Methods. 2011; 173:213-9.

Oh H L i wsp. An antibody against a novel and conserved epitope in the hemagglutinin 1 subunit neutralizes numerous H5N1 influenza viruses. J Virol. 2010; 84: 8275-8286.

Okuno Y i wsp. A common neutralizing epitope conserved between the hemagglutinins of influenza A virus H1 and H2 strains. J Virol. 1993; 67:2552-8.

Petric M i wsp. Role of the laboratory in diagnosis of influenza during seasonal epidemics and potential pandemics. J Infect Dis. 2006; 194 Suppl 2:S98-110.

Postel A i wsp. Broad spectrum reactivity versus subtype specificity-trade-offs in serodiagnosis of influenza A virus infections by competitive ELISA. J Virol Methods. 2011; 173:49-59.

Prabakaran M i wsp. Development of epitope-blocking ELISA for universal detection of antibodies to human H5N1 influenza viruses. PLoS One. 2009; 4:e4566.

Rowe T i wsp. Detection of antibody to avian influenza A (H5N1) virus in human serum by using a combination of serologic assays. J Clin Microbiol. 1999; 37:937-43.

Sączyńska V. Influenza virus hemagglutinin as a vaccine antigen produced in bacteria. Acta Biochim Pol. 2014; 61:561-72.

Skehel J J, Wiley D C. Receptor binding and membrane fusion in virus entry: the influenza hemagglutinin. Annu Rev Biochem. 2000; 69:531-69.

Steinhauer D A. Role of hemagglutinin cleavage for the pathogenicity of influenza virus. Virology. 1999; 258:1-20.

Stelzer-Braid S i wsp. A commercial ELISA detects high levels of human H5 antibody but cross-reacts with influenza A antibodies. J Clin Virol. 2008; 43:241-3.

Suarez D L. Overview of avian influenza DIVA test strategies. Biologicals. 2005; 33:221-6.

Sui J i wsp. Structural and functional bases for broad-spectrum neutralization of avian and human influenza A viruses. Nat Struct Mol Biol. 2009; 16:265-73.

Szewczyk B i wsp. Introduction to molecular biology of influenza a viruses. Acta Biochim Pol. 2014; 61:397-401.

Verhagen J H i wsp. Infectious disease. How a virus travels the world. Science. 2015 6; 347:616-7.

Wang S F i wsp. Generating and characterizing monoclonal and polyclonal antibodies against avian H5N1 hemagglutinin protein. Biochem Biophys Res Commun. 2009; 382:691-6.

Wilson I A i wsp. Structure of the haemagglutinin membrane glycoprotein of influenza virus at 3 A resolution. Nature. 1981; 289:366-73.

Wu R i wsp. A novel neutralizing antibody against diverse clades of H5N1 influenza virus and its mutants capable of airborne transmission. Antiviral Res. 2014; 106:13-23.

Xu X i wsp. Genetic characterization of the pathogenic influenza A/Goose/Guangdong/1/96 (H5N1) virus: similarity of its hemagglutinin gene to those of H5N1 viruses from the 1997 outbreaks in Hong Kong. Virology. 1999; 261:15-9.

Yang M i wsp. Production and diagnostic application of monoclonal antibodies against influenza virus H5. J Virol Methods. 2009; 162:194-202.

The invention claimed is:

1. A monoclonal antibody against hemagglutinin of an H5 serotype influenza virus or an antigen binding fragment thereof, wherein the antibody or antigen binding fragment thereof binds an epitope of H5 antigen, wherein the monoclonal antibody is selected from the group consisting of:

(i) G-1-31-22 produced by mouse hybridoma cell line G-1-31-22 deposited with the DSMZ under the number DSM ACC3292, (ii) G-2-14-10 produced by mouse hybridoma cell line G-2-14-10 deposited with the DSMZ under the number DSM ACC3293, (iii) G-5-32-5 produced by mouse hybridoma cell line G-5-32-5 deposited with the DSMZ under the number DSM ACC3294, (iv) G-6-42-42 produced by mouse hybridoma cell line G-6-42-42 deposited with the DSMZ under the number DSM ACC3295, (v) G-7-24-17 produced by mouse hybridoma cell line G-7-24-17 deposited with the DSMZ under the number DSM ACC3296, and (vi) G-7-27-18 produced by mouse hybridoma cell line G-7-27-18 deposited with the DSMZ under the number DSM ACC3297.

2. The monoclonal antibody against hemagglutinin of an H5 serotype influenza virus or an antigen binding fragment thereof according to claim 1, wherein the antigen binding fragment thereof is selected from the group consisting of Fab, Fab', F(ab')2, Fv, VH, VL and single-chain antibody molecules consisting of VL and VH domains bound to each other by peptide linker.

3. The monoclonal antibody according to claim 1, wherein the hemagglutinin is from an influenza virus of H5 serotype, selected from the group consisting of H5N1, H5N2, H5N3 and H5N9.

4. The monoclonal antibody according to claim 1, wherein the monoclonal antibody or the antigen binding fragment thereof is conjugated with an analytically detectable label, prodrug, drug, therapeutic agent, peptide, protein, enzyme virus, lipid, or PEG.

5. A mouse hybridoma cell line selected from the group consisting of:

(i) G-1-31-22 deposited with the DSMZ under the number DSM ACC3292, (ii) G-2-14-10 deposited with the DSMZ under the number DSM ACC3293, (iii) G-5-32-5 deposited with the DSMZ under the number DSM ACC3294, (iv) G-6-42-42 deposited with the DSMZ under the number DSM ACC3295, (v) G-7-24-17 deposited with the DSMZ under the number DSM ACC3296, and (vi) G-7-27-18 deposited with the DSMZ under the number DSM ACC3297.

6. A pharmaceutical or diagnostic composition comprising the monoclonal antibody against hemagglutinin of an H5 serotype influenza virus or an antigen binding fragment thereof according to claim 1 and a suitable carrier or label.

7. A method for in vitro diagnosis of an influenza virus H5 serotype infection, comprising contacting a biological sample with the monoclonal antibody against hemagglutinin of an H5 serotype influenza virus or an antigen binding fragment thereof, according to claim 1 and detecting binding of said antibody or an antigen binding fragment thereof with H5 serotype influenza virus or H5 hemagglutinin protein.

8. A diagnostic kit for detection of an influenza virus H5 serotype infection, comprising the monoclonal antibody against hemagglutinin of an H5 serotype influenza virus or an antigen binding fragment thereof according to claim 1, and reagents for detection of said antibody or antigen binding fragment thereof bound with H5 serotype influenza virus or H5 hemagglutinin protein.

9. A diagnostic kit for detection or quantification of an influenza H5 serotype virus in a biological sample, comprising the monoclonal antibody against hemagglutinin of an H5 serotype influenza virus or an antigen binding fragment thereof according to claim 1.

10. A diagnostic kit for detection or quantification of antibodies against H5 serotype influenza virus in a biological sample, comprising the monoclonal antibody against hemagglutinin of an H5 serotype influenza virus or an antigen binding fragment thereof as defined in claim 1.

11. A method of performing a test selected from the group consisting of an immunoenzymatic test, an immunofluorescent test, an immunochemiluminescent test, a radioimmunological test, an immunochromatographic test, an immunodiffusion test, and an immunoprecipitation test, comprising using a kit according to claim 8.

12. A method of performing a test selected from the group consisting of an immunoenzymatic test, an immunofluorescent test, an immunochemiluminescent test, a radioimmunological test, an immunochromatographic test, an immunodiffusion test, and an immunoprecipitation test, comprising using a kit according to claim 9.

13. A method of performing a test selected from the group consisting of an immunoenzymatic test, an immunofluorescent test, an immunochemiluminescent test, a radioimmunological test, an immunochromatographic test, an immunodiffusion test, and an immunoprecipitation test, comprising using a kit according to claim 10.

14. The diagnostic kit according to claim 8, wherein the monoclonal antibody against hemagglutinin of an H5 serotype influenza virus or an antigen binding fragment thereof is purified.

15. The diagnostic kit according to claim 9, wherein the monoclonal antibody against hemagglutinin of an H5 serotype influenza virus or an antigen binding fragment thereof is purified.

16. The diagnostic kit according to claim 10, wherein the monoclonal antibody against hemagglutinin of an H5 serotype influenza virus or an antigen binding fragment thereof is purified.

* * * * *

SEQUENCE LISTING

<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: synthetic

<400> SEQUENCE: 1

Ile Gln His Gln Asp Trp Thr Gly Gly Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic

<400> SEQUENCE: 2

Val Asn Ser Ala Ala Phe Pro Ala Pro Ile Glu Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic

<400> SEQUENCE: 3

Val His Asn Glu Gly Leu Pro Ala Pro Ile Val Arg
1               5                   10

<210> SEQ ID NO 4
<211> LENGTH: 16
<212> TYPE: PRT
<213> ORGANISM: Artificial Sequence
<220> FEATURE:

<223> OTHER INFORMATION: synthetic

<400> SEQUENCE: 4

Glu Pro Gln Val Tyr Val Leu Ala Pro Pro Gln Glu Glu Leu Ser Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetic

<400> SEQUENCE: 5

Ser Val Ser Glu Leu Pro Ile Met His Gln Asp Trp Leu Asn Gly Lys
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: synthetic

<400> SEQUENCE: 6

Phe Ser Trp Phe Val Asp Asp Val Glu Val Asn Thr Ala Thr Thr Lys
1               5                   10                  15

Pro Arg

<210> SEQ ID NO 7
<211> LENGTH: 19
<212> TYPE: PRT
<213> ORGANISM: Artificial Sequence
<220> FEATURE:
<223> OTHER INFORMATION: synthetic

<400> SEQUENCE: 7

Ser Val Ser Glu Leu Pro Ile Met His Gln Asp Trp Leu Asn Gly Lys
1               5                   10                  15

Glu Phe Lys

<210> SEQ ID NO 8
<211> LENGTH: 23
<212> TYPE: PRT
<213> ORGANISM: Artificial Sequence
<220> FEATURE:
<223> OTHER INFORMATION: synthetic

<400> SEQUENCE: 8

Ser Thr Val Ser Leu Thr Cys Met Val Thr Ser Phe Tyr Pro Asp Tyr
1               5                   10                  15

Ile Ala Val Glu Trp Gln Arg
            20

<210> SEQ ID NO 9
<211> LENGTH: 26
<212> TYPE: PRT
<213> ORGANISM: Artificial Sequence
<220> FEATURE:
<223> OTHER INFORMATION: synthetic

<400> SEQUENCE: 9

Asp Thr Leu Thr Ile Ser Gly Thr Pro Glu Val Thr Cys Val Val Val
1               5                   10                  15

-continued

```
Asp Val Gly His Asp Asp Pro Glu Val Lys
            20                  25


<210> SEQ ID NO 10
<211> LENGTH: 17
<212> TYPE: PRT
<213> ORGANISM: Artificial Sequence
<220> FEATURE:
<223> OTHER INFORMATION: synthetic

<400> SEQUENCE: 10

Pro Ala Val Leu Asn Gln Pro Ser Ser Val Ser Gly Ser Leu Gly Gln
1               5                   10                  15

Arg


<210> SEQ ID NO 11
<211> LENGTH: 16
<212> TYPE: PRT
<213> ORGANISM: Artificial Sequence
<220> FEATURE:
<223> OTHER INFORMATION: synthetic

<400> SEQUENCE: 11

Leu Trp Ile Tyr Gly Thr Ser Asp Leu Ala Ser Gly Val Pro Ala Arg
1               5                   10                  15


<210> SEQ ID NO 12
<211> LENGTH: 31
<212> TYPE: PRT
<213> ORGANISM: Artificial Sequence
<220> FEATURE:
<223> OTHER INFORMATION: synthetic

<400> SEQUENCE: 12

Ala Thr Leu Thr Val Asp Ala Ser Ser Ser Thr Ala Tyr Ile Gln Leu
1               5                   10                  15

Ser Ser Leu Ser Ser Glu Asp Ser Ala Val Tyr Phe Cys Ala Arg
            20                  25                  30


<210> SEQ ID NO 13
<211> LENGTH: 6
<212> TYPE: PRT
<213> ORGANISM: Artificial Sequence
<220> FEATURE:
<223> OTHER INFORMATION: synthetic

<400> SEQUENCE: 13

Arg Arg Arg Lys Lys Arg
1               5


<210> SEQ ID NO 14
<211> LENGTH: 6
<212> TYPE: PRT
<213> ORGANISM: Artificial Sequence
<220> FEATURE:
<223> OTHER INFORMATION: synthetic

<400> SEQUENCE: 14

His His His His His His
1               5
```